(12) United States Patent
Kirsch et al.

(10) Patent No.: US 7,029,730 B2
(45) Date of Patent: Apr. 18, 2006

(54) CF$_2$O-BRIDGED, AXIALLY SUBSTITUTED CYCLOHEXANE DERIVATIVES

(75) Inventors: Peer Kirsch, Darmstadt (DE); Andreas Taugerbeck, Darmstadt (DE); Detlef Pauluth, Ober-Ramstadt (DE); Joachim Krause, Dieburg (DE); Kazuaki Tarumi, Seeheim (DE); Georg Lüssem, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/479,621

(22) PCT Filed: May 2, 2002

(86) PCT No.: PCT/EP02/04797

§ 371 (c)(1),
(2), (4) Date: Dec. 4, 2003

(87) PCT Pub. No.: WO02/098832

PCT Pub. Date: Dec. 12, 2002

(65) Prior Publication Data

US 2004/0167361 A1 Aug. 26, 2004

(30) Foreign Application Priority Data

Jun. 5, 2001 (DE) .................. 101 27 218

(51) Int. Cl.
*C09K 19/34* (2006.01)
*C09K 19/30* (2006.01)
*C07C 22/08* (2006.01)
*C07C 23/10* (2006.01)
*C07D 319/06* (2006.01)

(52) U.S. Cl. ............ 428/1.1; 252/299.61; 252/299.63; 549/369; 570/127; 570/129; 570/130; 570/131

(58) Field of Classification Search ................ 428/1.1; 252/299.61, 299.63; 549/369; 570/127, 570/129, 130, 131; 568/74
See application file for complete search history.

(56) References Cited

U.S. PATENT DOCUMENTS

| 6,056,895 A | 5/2000 | Kirsch et al. |
| 6,057,006 A | 5/2000 | Kirsch et al. |
| 6,187,223 B1 | 2/2001 | Andou et al. |
| 6,319,570 B1 | 11/2001 | Andou et al. |
| 6,630,210 B1 * | 10/2003 | Kirsch et al. ............. 428/1.1 |
| 6,780,477 B1 * | 8/2004 | Kirsch et al. ............. 428/1.1 |

FOREIGN PATENT DOCUMENTS

| DE | 19714231 A | 10/1998 |
| DE | 19723275 A | 12/1998 |
| EP | 0844229 A | 5/1998 |
| EP | 0916639 A | 5/1999 |

OTHER PUBLICATIONS

Kirsch, Peer, et al Difluorooxymethylene-bridged liquid crystals. A novel synthesis based on the oxidative alkoxy-difluorodesulfuration of dithianylium salts: Angewandte Chemie, International Edition 2001, 40(8), 1480-1484, Apr. 17, 2001.

* cited by examiner

*Primary Examiner*—Shean C. Wu
(74) *Attorney, Agent, or Firm*—Millen, White, Zelano, Branigan, P.C.

(57) ABSTRACT

The invention relates to CF$_2$O-bridged cyclohexane derivatives, in particular compounds of formula (I), R1-(-A1-Z1-)k1-Q-CF2O-A2-(-Z3-A3-)K3-R2, wherein Q represents group (a); $W^1$, $W^2$ represent —CH$_2$— and/or —O— independendy from each other, $X^1$, $X^2$, $X^3$, $X^4$ represent H, F, —CH$_3$ —CH$_2$F—CH$_2$F and/or —CF$_3$ independently from each other, provided that at least one substituent $X^1$, $X^2$, $X^3$ and/or $X^4$ does not represent H, $Z^2$ represents a simple bond, —CH$_2$—CH$_2$— or —CF$_2$—CF$_2$—, m represents 0 or 1 and $R^1$, $R^2$, $A^1$, $A^2$, $A^3$, $Z^1$, $Z^3$, k1 and k3 have the meaning cited in the description. The invention further relates to liquid crystal substances such as optical and electro-optical display elements.

16 Claims, No Drawings

CF₂O-BRIDGED, AXIALLY SUBSTITUTED CYCLOHEXANE DERIVATIVES

The invention relates to CF$_2$O-bridged, axially substituted cyclohexane derivatives, in particular compounds of the formula I

in which
Q is the

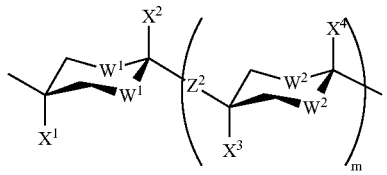

group,

W$^1$ and W$^2$, independently of one another, are —CH$_2$— and/or —O—,

X$^1$, X$^2$, X$^3$ and X$^4$, independently of one another, are H, F, —CH$_3$, —CH$_2$F, —CHF$_2$ and/or —CF$_3$, with the proviso that at least one substituent X$^1$, X$^2$, X$^3$ and/or X$^4$ is not H, Z$^2$ is a single bond, —CH$_2$—CH$_2$— or —CF$_2$—CF$_2$—, m is 0 or 1, R$^1$ and R$^2$, independently of one another, are H, halogen, —CN, —NCS, —SF$_5$ or alkyl having from 1 to 12 carbon atoms, in which, in addition, one or two non-adjacent —CH$_2$— groups may be replaced by —O—, —S—, —CO—, —O—CO—, —CO—O—, —E— and/or —C≡C— and/or in which, in addition, one or more H atoms may be replaced by halogen and/or —CN, E is CR$^4$=CR$^5$ or CHR$^4$—CHR$^5$, R$^4$ and R$^5$ are each, independently of one another, H, alkyl having 1–6 carbon atoms, F, Cl, CF$_3$ or CN, A$^1$, A$^2$ and A$^3$, independently of one another, are
  a) a trans-1,4-cyclohexylene radical, in which, in addition, one or more non-adjacent CH$_2$ groups may be replaced by —O— and/or —S—,
  b) a 1,4-phenylene radical, in which, in addition, one or two CH groups may be replaced by N,
  c) a radical from the group consisting of 1,4-bicyclo[2.2.2]-octylene, piperidine-1,4-diyl, naphthalene-2,6-diyl, decahydronaphthalene-2,6-diyl and 1,2,3,4-tetrahydro-naphthalene-2,6-diyl,
  d) 1,4-cyclohexenylene,
  where the radicals a), b) and d) may be substituted by CN, Cl or F, Z$^1$ and Z$^3$ are each, independently of one another, —CO—O—, —O—CO—, —O—, —CH$_2$—O—, —CF$_2$—O—, —O—CH$_2$—, —O—CF$_2$—, —C$_2$H$_4$—, —CH$_2$—CF$_2$—, —CF$_2$—CH$_2$—, —CF$_2$—CF$_2$—, —CH=CH—, —CF=CH—, —CH=CF—, —CF=CF—, —C≡C— or a single bond, k1 and k3, independently of one another, are 0, 1 or 2.

The invention furthermore relates to liquid-crystalline media and to liquid-crystal and electro-optical display elements which contain the liquid-crystalline media according to the invention.

The compounds according to the invention can be used as components of liquid-crystalline media, in particular for displays based on the principle of the twisted cell, the guest-host effect, the DAP (deformation of aligned phases), ECB (electrically controlled birefringence), CSH (colour super homeotropic), VA (vertically aligned) or IPS (in plane switching) effect or the effect of dynamic scattering. All the substances employed hitherto for this purpose have certain disadvantages, for example inadequate stability to the action of heat, light or electric fields, or unfavourable elastic and/or dielectric properties.

1,4-trans-disubstituted cyclohexane derivatives which additionally have an axial substituent in the 1- and/or 4-position are disclosed in DE 197 14 231 A1, DE 197 23 275 A1 and DE 197 31 712 A1. These compounds, which generally have negative dielectric anisotropy, are quoted as having high thermal stability, which is advantageous for a high voltage holding ratio, and favourable values for the clearing points.

CF$_2$O-bridged liquid-crystalline compounds are disclosed, for example, in DE 195 31 165 A1 and EP 844 229 A1. Owing to their high values for the dielectric anisotropy and comparatively low viscosities, compounds of this type can advantageously be employed in liquid-crystalline media for TFT-LCDs.

Each liquid-crystal display element makes very specific demands on the liquid-crystalline media to be employed with respect to their physical-chemical properties, such as temperature ranges for the mesophases, dielectric anisotropy (Δε), optical anisotropy (Δn), viscosity, threshold voltage (V$_{th}$), stability to electromagnetic and thermal radiation. These properties generally cannot satisfied by individual substances, which is why specially matched mixtures of usually from 10 to 15 liquid-crystalline or mesogenic compounds are used. In order to be able to satisfy the requi-site properties in the most optimum manner possible, it is advantageous for a multiplicity of individual liquid-crystalline or mesogenic compounds having a broad range of desired physical properties to be available. Besides the stated physical-chemical parameters to be optimised, the compounds and thus the mixtures should also have good solubility in liquid-crystal mixtures and high reliability. The term reliability is taken to mean a number of properties without which, in addition to the said parameters, the compounds cannot be used satisfactorily in display elements (P. Kirsch, M. Bremer, Angew. Chemie 112, 2000, 4384–4405). An important factor here is the long-term stability to thermal and/or photochemical decomposition, for example in projection displays having very strong light sources. Further factors are the voltage holding ratio, the specific resistance and the ion density.

The object of the present invention is to provide novel, stable, liquid-crystalline or mesogenic compounds having high reliability which are distinguished, in particular, by very low affinity to ionic impurities and/or by improved solubility in liquid-crystal mixtures.

Further objects of the invention relate to the provision of liquid-crystalline media and optical and electro-optical display elements.

The first-mentioned object is achieved by CF$_2$O-bridged, axially substituted cyclohexane derivatives of the formula I. It has been found that the compounds according to the invention are eminently suitable as components of liquid-crystalline media. They can be used to obtain stable liquid-crystalline media which are particularly suitable for electro-optical LC displays. The compounds according to the invention have improved reliability compared with known CF$_2$O-bridged compounds. Thus, the affinity to ionic impurities is comparatively low. This enables display elements having improved image quality, in particular greater contrast, which are stable in the long term to be obtained.

Furthermore, the compounds according to the invention have improved solubility in liquid-crystalline media, meaning that the compounds can be employed in a broad concentration range.

In addition, the compounds according to the invention have favourable mesophase ranges for use in electro-optical display elements and have advantageous values for the optical anisotropy.

The provision of the compounds according to the invention very generally considerably broadens the range of liquid-crystalline substances which are suitable, from various applicational points of view, for the preparation of liquid-crystalline mixtures.

In addition, the invention relates to a liquid-crystalline medium having two or more liquid-crystalline components, where the medium comprises at least one compound according to the invention. The use of compounds of this type enables the reliability of liquid-crystalline media for use in LC display elements to be increased. In addition, however, it is also possible to add one or more compounds according to the invention to liquid-crystalline media in order specifically to modify the dielectric anisotropy and/or the optical anisotropy and/or the viscosity and/or the mesophase ranges and/or the tilt angle of media of this type.

The compounds according to the invention can be used as components of liquid-crystalline media, in particular for displays based on the principle of the twisted cell, the guest-host effect, the DAP (deformation of aligned phases), ECB (electrically controlled birefringence), CSH (colour super homeotropic), VA (vertically aligned) or IPS (in plane switching) effect or the effect of dynamic scattering.

Furthermore, owing to their transverse dipole moment, the compounds according to the invention can be used in display elements which require a high transverse dipole moment. For example, the compounds according to the invention can in principle thus be employed as components of optically active tilted smectic (ferroelectric) liquid-crystalline media, in particular for displays based on the SSFLCD (surface stabilised ferroelectric liquid crystal display) effect of Clark and Lagerwall, but also on the DHF (distorted helix formation) effect or the PSFLCD (pitch stabilised ferroelectric liquid crystal display) effect, which is also known as the SBF (short pitch bistable ferroelectric) effect. Further applications are MVA (multi-domain vertical alignment) displays, in particular MVA-TFT displays, and PALC displays (plasma-addressed LCDs).

The invention furthermore relates to an optical display element which contains a liquid-crystalline medium according to the invention, and to an electro-optical display element which contains, as dielectric, a liquid-crystalline medium according to the invention. The above-mentioned display elements are preferred here.

Above and below, the groups, substituents and indices Q, $W^1$, $W^2$, $X^1$, $X^2$, $X^3$, $X^4$, $R^1$, $R^2$, E, $Z^1$, $Z^2$, $Z^3$, $A^1$, $A^2$, $A^3$, k1, k3 and m have the meaning indicated for the formula I, unless expressly stated otherwise. If a group, a substituent and/or an index occurs more than once, it may adopt identical or different meanings.

The meaning of the formula I covers all isotopes of the chemical elements bonded in the compounds of the formula I. If compounds of the formula I have one or more chiral centers, the formula I also covers enantiomerically pure and enriched forms in addition to the racemates. In enantiomerically pure or enriched form, the compounds of the formula I are also suitable as chiral dopants and in general for achieving chiral mesophases.

Preferred meanings of groups and substituents of the compounds according to the invention are indicated below.

Preferred meanings of the group Q are shown by the sub-formulae Q1 to Q10:

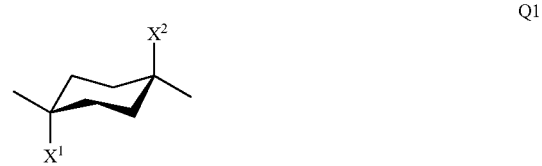

Q1

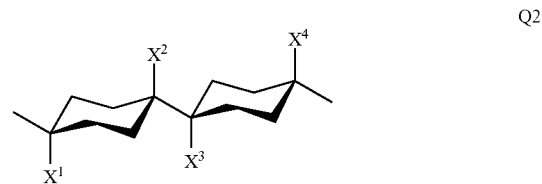

Q2

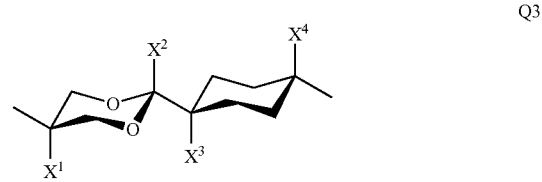

Q3

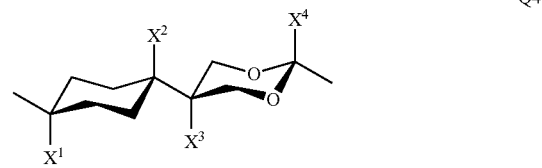

Q4

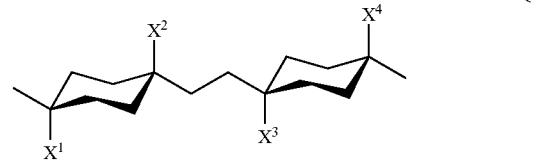

Q5

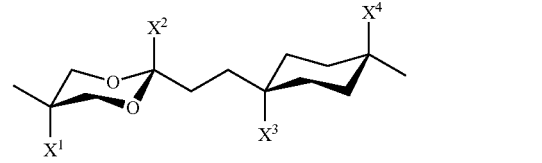

Q6

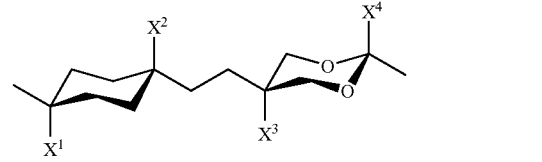

Q7

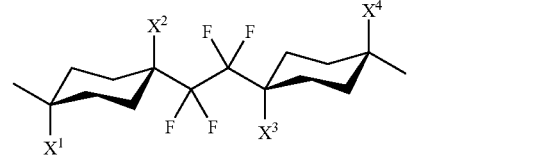

Q8

-continued

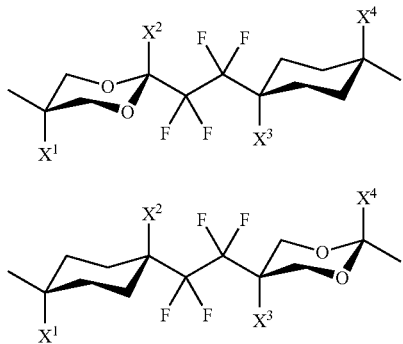
Q9

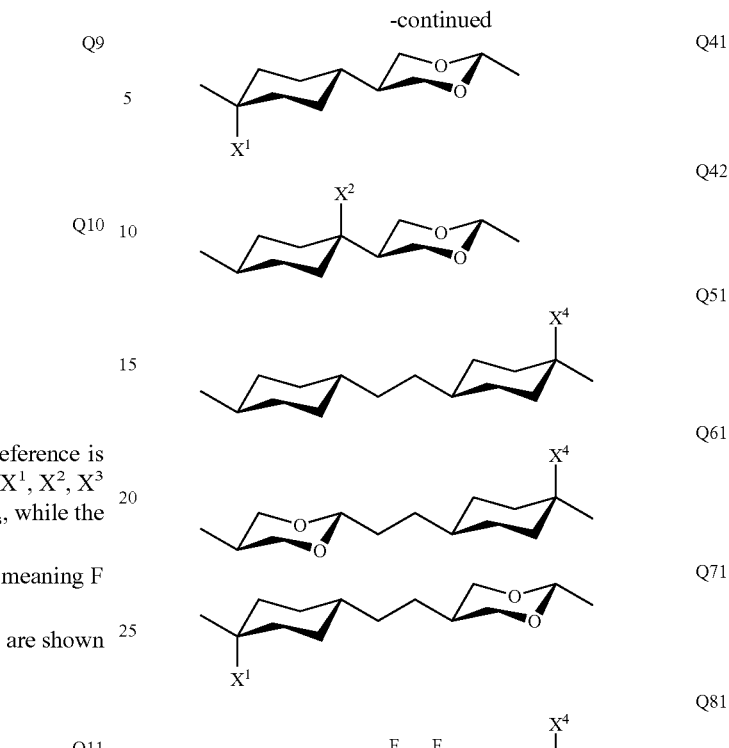
Q41
Q42
Q51
Q61
Q71
Q81

Of the sub-formulae Q1 to Q10, particular preference is given to those in which precisely one substituent $X^1$, $X^2$, $X^3$ or $X^4$ is —F, —CH$_3$, —CH$_2$F, —CHF$_2$ or —CF$_3$, while the other substituents $X^1$, $X^2$, $X^3$ and $X^4$ are H.

If a substituent $X^1$, $X^2$, $X^3$ or $X^4$ is not H, the meaning F and/or —CF$_3$ is preferred.

Particularly preferred meanings of the group Q are shown by the following sub-formulae:

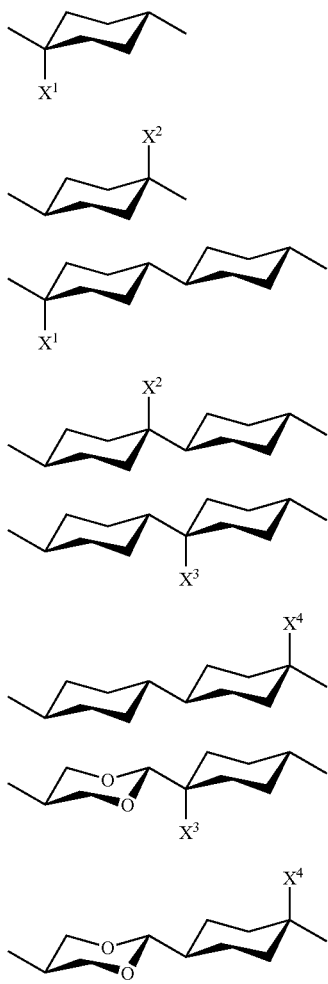
Q11
Q12
Q21
Q22
Q23
Q24
Q31
Q32

The meanings in accordance with the sub-formulae Q12, Q24, Q32, Q51 and Q81 are very particularly preferred.

According to a first preferred embodiment of the invention, k1 and k3 have the value 0, and the compounds according to the invention therefore have the formula Ia:

$$R^1\text{-Q-CF}_2\text{O-A}^2\text{-R}^2 \qquad \text{Ia}$$

In a second embodiment, k1=1 and k3=0, and consequently the compounds according to the invention have the formula Ib:

$$R^1\text{-A}^1\text{-Z}^1\text{-Q-CF}_2\text{O-A}^2\text{-R}^2 \qquad \text{Ib}$$

According to a third embodiment, k1=0 and k3=1, and so the compounds according to the invention have the formula Ic:

$$R^1\text{-Q-CF}_2\text{O-A}^2\text{-Z}^3\text{-A}^3\text{-R}^2 \qquad \text{Ic}$$

The present invention also covers compounds of the following formulae:

$$R^1\text{-A}^1\text{-Z}^1\text{-A}^1\text{-Z}^1\text{-Q-CF}_2\text{O-A}^2\text{-R}^2 \qquad \text{Id}$$

$$R^1\text{-A}^1\text{-Z}^1\text{-Q-CF}_2\text{O-A}^2\text{-Z}^3\text{-A}^3\text{-R}^2 \qquad \text{Ie}$$

$$R^1\text{-Q-CF}_2\text{O-A}^2\text{-Z}^3\text{A}^3\text{-Z}^3\text{-A}^3\text{-R}^2 \qquad \text{If}$$

Particularly preferred meanings of $A^1$, $A^2$ and/or $A^3$ are, independently of one another, 1,4-phenylene, which may be monosubstituted, disubstituted or trisubstituted by F, Cl and/or —CN, trans-1,4-cyclohexylene, 1,4-cyclohexenylene and 1,3-dioxane-2,5-diyl.

The term 1,3-dioxane-2,5-diyl covers each of the two positional isomers

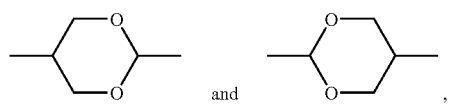 and 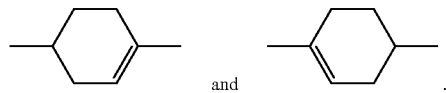,
and the term 1,4-cyclohexenylene covers each of the two positional isomers
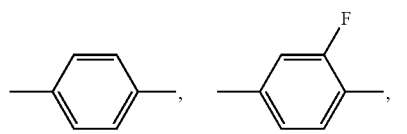 and 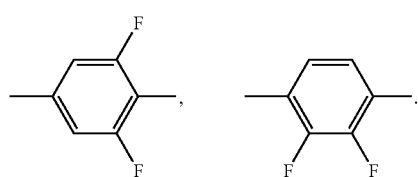.
$A^2$ is very particularly preferably a sub-formula from the following group:
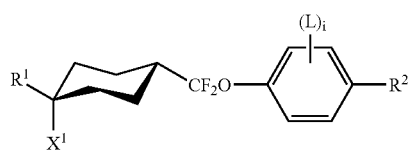, 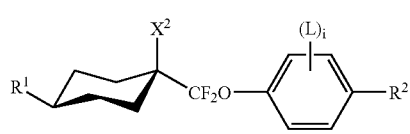,
Particular preference is given to the compounds of the formulae I1 to I14:
I1
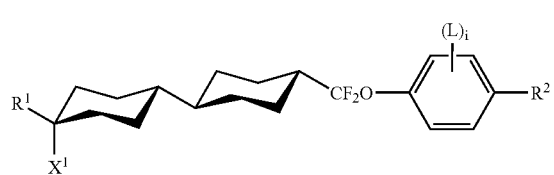
I2
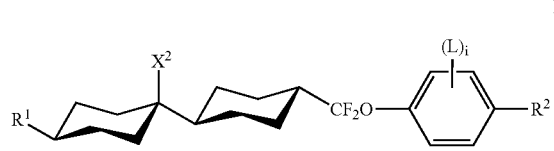
I3
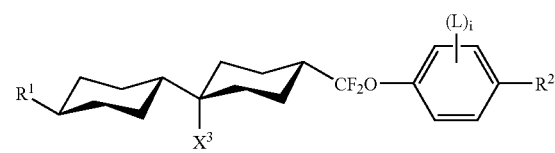
I4
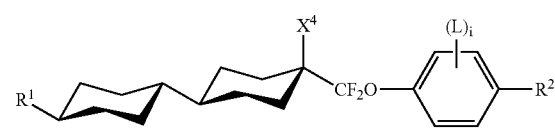
I5
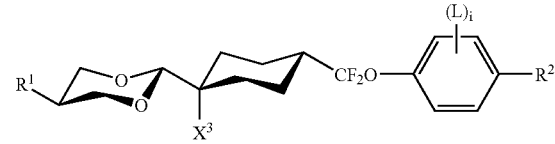
I6
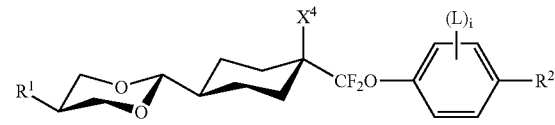
I7
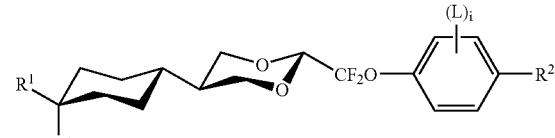
I8
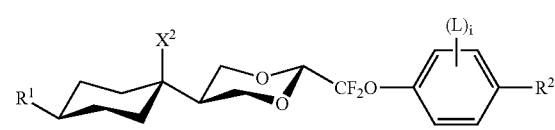
I9
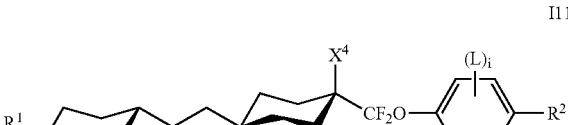
I10
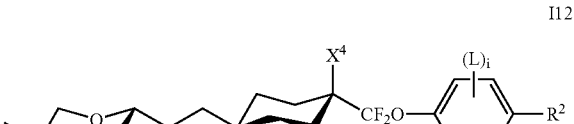
I11
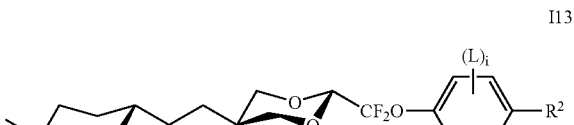
I12
I13

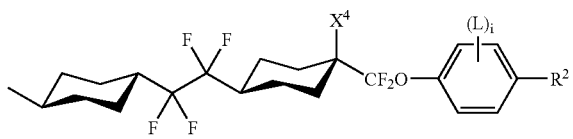

Of these, very particular preference is given to the compounds of the formulae I2, I6 and I8.

Above and below, L is F, Cl and/or —CN, and i is 0, 1, 2, 3 or 4, preferably 0, 1 or 2.

The group

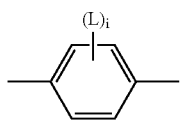

is preferably

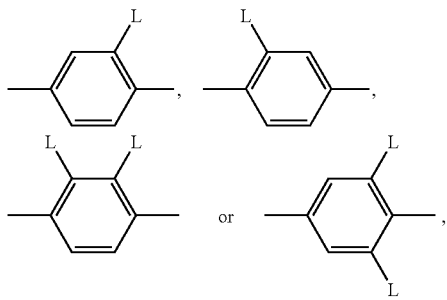

where L is as defined above, in particular is F.

In the case of the meaning alkyl in the groups or substituents indicated above or below, in particular in $R^1$ and/or $R^2$, the alkyl radical may be linear or branched. It preferably has 1, 2, 3, 4, 5 or 6 carbon atoms. It is preferably linear and is therefore particularly methyl, ethyl, propyl, butyl, pentyl and/or hexyl.

$R^1$ and/or $R^2$ are preferably alkyl, alkenyl, alkoxy, alkenyloxy, oxaalkyl, oxaalkenyl, alkylcarbonyloxy or alkyloxycarbonyl.

Besides the above-mentioned meanings in the case of alkyl, $R^1$ and $R^2$ as alkyl may also have 7, 8 or more than 8 carbon atoms and are therefore particularly heptyl, octyl, nonyl, decyl, undecyl or dodecyl.

Further preferred meanings of $R^1$ and/or $R^2$ are alkoxy. The alkoxy radical may be linear or branched. It is preferably linear and has 1, 2, 3, 4, 5, 6, 7 or 8 carbon atoms and is therefore particularly methoxy, ethoxy, propoxy, butoxy, pentoxy, hexoxy, heptoxy or octoxy, furthermore nonoxy, decoxy, undecoxy, dodecoxy, tridecoxy or tetradecoxy.

Furthermore, $R^1$ and/or $R^2$ are preferably oxaalkyl. The radical may be linear or branched. It is preferably linear and is, for example, 2-oxapropyl(=methoxymethyl), 2-(=ethoxymethyl) or 3-oxabutyl(=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl.

If $R^1$ and/or $R^2$ are an alkenyl radical, this may be straight-chain or branched. It is preferably straight-chain and has from 2 to 8 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl or oct-1-, -2-, -3-, -4-, -5-, -6- or −7-enyl.

If $R^1$ and/or $R^2$ is an alkenyloxy radical, this may be straight-chain or branched. It is preferably straight-chain and accordingly is in particular vinyloxy, prop-1- or -2-enyloxy, but-1-, -2- or -3-enyloxy, pent-1-, -2-, -3- or -4-enyloxy, hex-1-, -2-, -3-, -4- or -5-enyloxy, hept-1-, -2-, -3-, -4-, -5- or -6-enyloxy or oct-1-, -2-, -3-, -4-, -5-, -6- or -7-enyloxy.

If $R^1$ and/or $R^2$ are an oxaalkenyl radical, this may be straight-chain or branched. It is preferably straight-chain and is particularly preferably 3-oxabut-1-enyl(=methoxyvinyl), 2-oxabut-3-enyl(=vinyloxymethyl), 4-oxapent-1-enyl (=methoxyprop-1-enyl), 3-oxapent-1-enyl(=ethoxyvinyl), 4-oxapent-2-enyl(=methoxyprop-2-enyl), 2-oxapent-3-enyl (=prop-1-enoxymethyl), 2-oxapent-4-enyl(=prop-2-enoxymethyl), 3-oxapent-4-enyl(=vinyloxyethyl), 3-oxahex-1-enyl, 4-oxahex-1-enyl, 5-oxahex-1-enyl, 4-oxahex-2-enyl, 5-oxahex-2-enyl, 2-oxahex-3-enyl, 5-oxahex-3-enyl, 2-oxahex-4-enyl, 3-oxahex-4-enyl, 2-oxahex-5-enyl, 3-oxahex-5-enyl or 4-oxahex-5-enyl.

If $R^1$ and/or $R^2$ are an alkyl radical in which one $CH_2$ group has been replaced by —O— and one has been replaced by —CO—, these are preferably adjacent. This thus contains a carbonyloxy group (acyloxy group) —CO—O— or an oxycarbonyl group —O—CO—. These are preferably straight-chain and have from 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl) propyl, 3-(ethoxycarbonyl)propyl or 4-(methoxycarbonyl) butyl.

Compounds of the formula I having a branched wing group $R^1$ and/or $R^2$ may occasionally be of importance owing to better solubility in the conventional liquid-crystalline base materials, but in particular as chiral dopants if they are optically active. Smectic compounds of this type are particularly suitable as components of ferroelectric materials.

Branched groups of this type generally contain not more than one chain branch. Preferred chiral branched radicals $R^1$ and/or $R^2$ are 2-butyl(=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 1-methylheptyloxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy.

Preferred achiral branched radicals $R^1$ and/or $R^2$ are isopropyl, isobutyl(=2-methylpropyl), isopentyl(=3-methylbutyl), isopropoxy, 2-methylpropoxy and 3-methylbutoxy.

In the case of the above-mentioned meanings of $R^1$ and $R^2$, in particular as alkyl, alkenyl, alkoxy, alkenyloxy, oxaalkyl, oxaalkenyl, alkylcarbonyloxy or alkyloxycarbonyl, one or more H atoms have preferably been replaced by halogen atoms, preferably by fluorine and/or chlorine, particularly preferably by fluorine. Preferably, 2 or more H atoms have been substituted by fluorine. Particularly preferably, 2 or 3 H atoms in the terminal methyl group in the above-mentioned radicals have been substituted by fluorine, so that the above-mentioned radicals contain a —$CHF_2$ or a —$CF_3$ group. The entire radical $R^1$ and/or $R^2$ can also be perfluorinated.

Particularly preferred fluorinated radicals $R^1$ and $R^2$ as alkyl are —$CHF_2$, —$CF_3$, —$CH_2CHF_2$, —$CH_2CF_3$, —$CF_2CHF_2$, —$CF_2CF_3$, —$CH_2CH_2CHF_2$, —$CH_2CH_2CF_3$, —$CH_2CF_2CHF_2$, —$CH_2CF_2CF_3$, —$CF_2CH_2CHF_2$, —$CF_2CH_2CF_3$, —$CF_2CF_2CHF_2$, —$CF_2CF_2CF_3$, —$C_4F_9$, —$C_5F_{11}$, —$C_6F_{13}$, —$C_7F_{15}$ or —$C_8F_{17}$.

Particularly preferred fluorinated radicals $R^1$ and $R^2$ as alkenyl are —CH=CHF, —CH=$CF_2$, —CF=$CF_2$, —CH=$CHCF_3$, —CH=$CF$—$CF_3$, —CF=$CFCF_3$, —$CH_2$—CH=CHF, —$CH_2$—CH=$CF_2$, —$CF_2$—CH=$CH_2$, —$CF_2$—CF=CHF, —$CF_2$—CH=$CF_2$, —$CF_2$—CF=$CF_2$ or —$CF_2$—CF=$CFCF_3$.

Particularly preferred fluorinated radicals $R^1$ and $R^2$ as alkoxy are —$OCHF_2$, —$OCF_3$, —$OCH_2CHF_2$, —$OCH_2CF_3$, —$OCF_2CHF_2$, —$OCF_2CF_3$, —$OCH_2CH_2CHF_2$, —$OCH_2CH_2CF_3$, —$OCH_2CF_2CHF_2$, —$OCH_2CF_2CF_3$, —$OCF_2CH_2CHF_2$, —$OCF_2CH_2CF_3$, —$OCF_2CF_2CHF_2$, —$OCF_2CF_2CF_3$, —$OC_4F_9$, —$OC_5F_{11}$, —$OC_6F_{13}$, —$OC_7F_{15}$ or —$OC_8F_{17}$.

Particularly preferred fluorinated radicals $R^1$ and $R^2$ as alkenyloxy are —OCH=CHF, —OCH=$CF_2$, —OCF=$CF_2$, —OCH=$CHCF_3$, —OCH=CF—$CF_3$, —OCF=$CFCF_3$, —$OCH_2$—CH=CHF, —$OCH_2$—CH=$CF_2$, —$OCH_2$—CF=$CF_2$, —$OCF_2$—CH=$CH_2$, —$OCF_2$—CH=CHF, —$OCF_2$—CH=$CF_2$, —$OCF_2$—CF=$CF_2$, —$OCH_2$—CH=$CHCF_3$, —$OCF_2$—CH=$CHCH_3$, —$OCF_2$—CH=$CHCF_3$ or —$OCF_2$—CF=$CFCF_3$.

Particularly preferred fluorinated radicals $R^1$ and $R^2$ as oxaalkyl are —$CH_2OCHF_2$, —$CH_2OCF_3$, —$CF_2OCH_3$, —$CF_2OCHF_2$, —$CF_2OCF_3$, —$CH_2OCH_2CHF_2$, —$CH_2OCH_2CF_3$, —$CH_2OCF_2CF_3$, —$CF_2OCH_2CF_3$ or —$CF_2OCF_2CF_3$.

Particularly preferred fluorinated radicals $R^1$ and $R^2$ as oxaalkenyl are —$CH_2$OCH=CHF, —$CH_2$OCH=$CF_2$, —$CH_2$OCF=$CF_2$, —$CF_2$OCH=$CH_2$, —$CF_2$OCH=CHF, —$CF_2$OCH=$CF_2$, —$CF_2$OCF=$CF_2$, —$CH_2$OCH=$CHCF_3$, —$CH_2$OCH=$CFCF_3$, —$CH_2$OCF=$CFCF_3$, —$CF2OCH$=$CHCH_3$, —$CF_2$OCH=$CHCF_3$, —$CF_2$OCH=$FCF_3$ or —$CF_2$OCF=$CFCF_3$.

Of the compounds of the formula I and the sub-formulae, preference is given to those in which at least one of the groups, substituents and/or indices present therein has one of the preferred meanings indicated.

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart. The preparation is carried out here under reaction conditions which are known and suitable for the said reactions. Use can also be made here of synthetic variants which are known per se, but are not mentioned here in greater detail. The starting materials and/or intermediates can also, if necessary, be formed in situ, i.e. they are not isolated from the reaction mixture, but instead immediately reacted further.

The reaction conditions to be observed in the said reactions are known per se to the person skilled in the art. In general, the reaction is carried out at a temperature of from −100 to +50° C. As solvent, use is made of inert polar solvents or mixtures thereof, for example ethers or haloalkanes, such as diethyl ether, tetrahydrofuran or dichloromethane.

The synthesis of compounds according to the invention is illustrated with reference to reaction schemes 1 to 4, in which the individual groups, substituents and indices are as defined above.

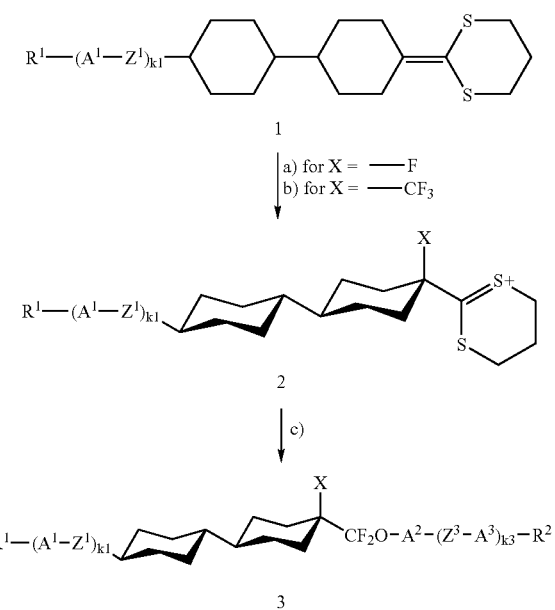

Reaction scheme 1 a) $PhSO_2NFSO_2Ph$ (S. D. Taylor, C. C. Kotoris, G. Hum, Tetrahedron 55, 1999, 12431–12477), $CH_2Cl_2$.

b) S-Trifluoromethyl(2,7-dinitrodibenzothiophenium)triflate (T. Umemoto, S. Ishihara, J. Am. Chem. Soc. 1993, 115, 2156–2164), $CH_2Cl_2$.

c) 1. Phenol derivative, $NEt_3$, −70° C.; 2. $NEt_3$.3HF, −70° C.; 3. $Br_2$, −70° C. to −20° C. (P. Kirsch, M. Bremer, A. Taugerbeck, T. Wallmichrath, Angew. Chem. 113, 2001, 1528–1532)

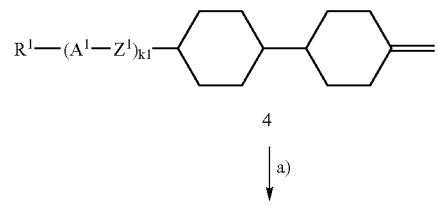

Reaction scheme 2 a)

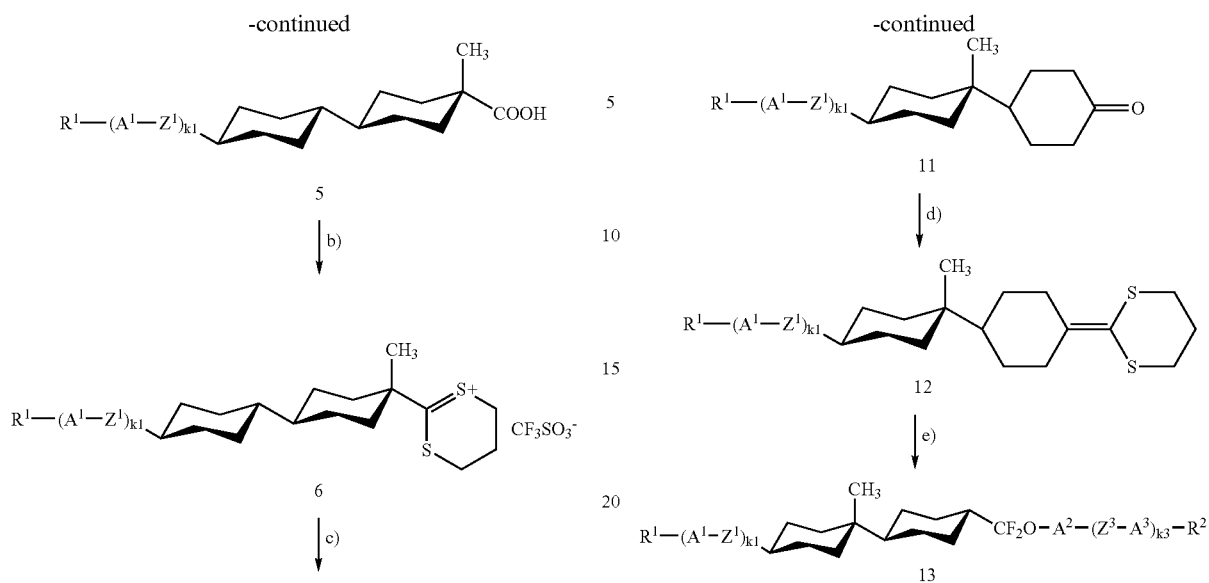

a) H$_2$SO$_4$, H$_2$O, HCOOH (Koch; Haaf, Liebigs Ann. Chem. 1958, 618, 251)

b) 1. Propanedithiol, CF$_3$SO$_3$H; 2. Diethyl ether (P. Kirsch, M. Bremer, A. Taugerbeck, T. Wallmichrath, Angew. Chem. 113, 2001, 1528–1532)

c) 1. Phenol derivative HO-A$^2$-(Z$^3$-A$^3$)$_{k3}$-R$^2$, NEt$_3$, −70° C.; 2. NEt$_3$.3HF, −70° C.; 3. Br$_2$, −70° C. to −20° C.

a) CH$_3$PPh$_3$Br, KOtBu, THF; −10° C.

b) H$_2$SO$_4$, CH$_2$Cl$_2$, phenol; 0° C.

c) H$_2$, cat. Pd/CaCO$_3$, THF.

d) 2-Trimethylsilyl-1,3-dithiane, n-BuLi, THF; −70° C. to 20° C.

e) 1. CF$_3$SO$_3$H, CH$_2$Cl$_2$; −70° C. (30 min), 20° C. (1 h), −70° C.; 2. Phenol derivative, NEt$_3$; 3. NEt$_3$-3HF; 4. Br$_2$; −70° C. to −20° C.

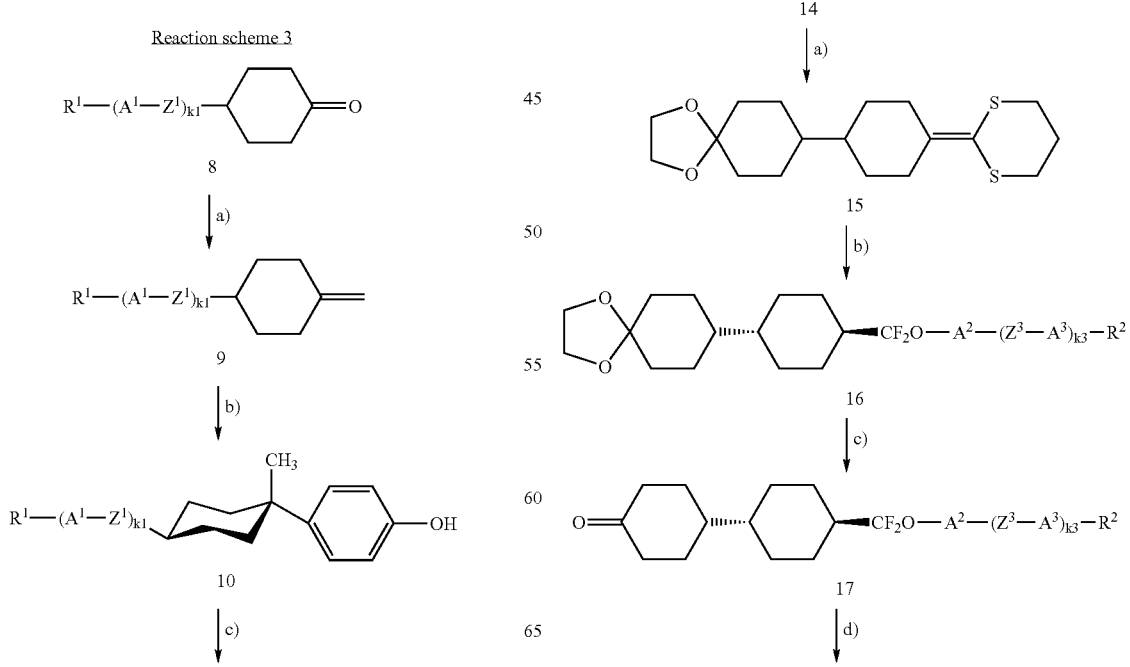

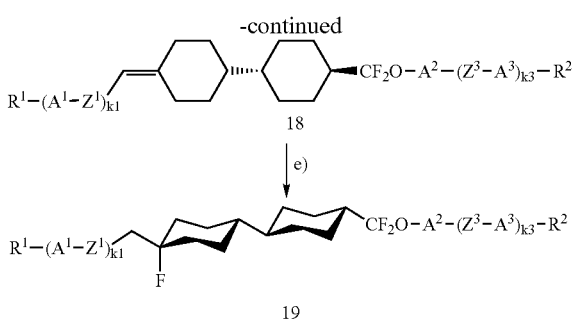

a) 2-Trimethylsilyl-1,3-dithiane, n-BuLi, THF; −70° C. to 20° C.
b) 1. $CF_3SO_3H$, $CH_2Cl_2$; −70° C. (30 min), 20° C. (1 h), −70° C.; 2. Phenol derivative $HO-A^2-(Z^3-A^3)_{k3}-R^2$, $NEt_3$; 3. $NEt_3$-3HF; 4. $Br_2$; −70° C. to −20° C.
c) HCOOH, toluene; 20° C.
d) $R^1$—$(A^1-Z^1)_{k1}$-$PPh_3Br$, KOtBu, THF; −10° C.
e) 70% HF/pyridine, $CH_2Cl_2$; 0° C., 18 h.

Compounds according to the invention in which m=1 and $Z^2$ is —$CH_2$—$CH_2$— or —$CF_2$—$CF_2$— can likewise be prepared in accordance with reaction schemes 1 to 4 using the correspondingly $Z^2$-bridged starting compounds, whose preparation is itself known or can be carried out using correspondingly processes which are familiar to the person skilled in the art. The following formulae show examples of suitable starting compounds of this type:

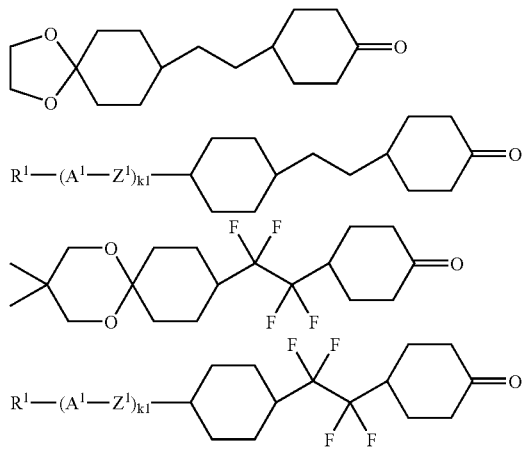

Further possible syntheses of compounds according to the invention are indicated below.

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols are known or can be prepared analogously to known processes.

Suitable reactive derivatives of the said carboxylic acids are in particular the acid halides, especially the chlorides and bromides, furthermore the anhydrides, azides or esters, in particular alkyl esters having 1–4 carbon atoms in the alkyl group.

Suitable reactive derivatives of the said alcohols are, in particular, the corresponding metal alkoxides, preferably of an alkali metal, such as Na or K.

The esterification is advantageously carried out in the presence of an inert solvent. Highly suitable solvents are, in particular, ethers, such as diethyl ether, di-n-butyl ether, THF, dioxane and anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Waterimmiscible solvents may advantageously be used at the same time for azeotropic removal by distillation of the water formed during the esterification. An excess of an organic base, for example pyridine, quinoline or triethylamine, may occasionally also be used as solvent for the esterification. The esterification may also be carried out in the absence of a solvent, for example by simple heating of the components in the presence of sodium acetate. The reaction temperature is usually between −50° C. and +250° C., preferably between −20° C. and +80° C. At these temperatures, the esterification reactions are generally complete after from 15 minutes to 48 hours.

In detail, the reaction conditions for the esterification depend substantially on the nature of the starting materials used. Thus, a free carboxylic acid is generally reacted with a free alcohol in the presence of a strong acid, for example a mineral acid, such as hydrochloric acid or sulfuric acid. A preferred reaction procedure is the reaction of an acid anhydride or in particular an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises firstly converting the alcohol into the sodium alkoxide or potassium alkoxide, for example by treatment with ethanolic sodium hydroxide solution or potassium hydroxide solution, isolating this alkoxide, and reacting it with an acid anhydride or in particular an acid chloride.

In a further process for the preparation of the compounds of the formula I in which $Z^1$ or $Z^3$ is —CH=CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are the salts thereof, in particular Pd(II) acetate, with organic phosphorus(III) compounds, such as, for example, triarylphosphines. The process can be carried out in the presence or absence of an inert solvent at temperatures between about 0° C. and 150° C., preferably between 20° C. and 100° C.; suitable solvents are, for example, nitriles, such as acetonitrile, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

In this way, stilbene derivatives, for example, can be prepared. The stilbenes can furthermore be prepared by reaction of a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

For the coupling of aromatic compounds, it is furthermore possible to react aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ or $Z^3$ is —C≡C— can also be prepared by the Fritsch-buttenberg-Wiechell rearrangement (Ann. 279, 319, 1984), in which 1,1-diaryl-2-haloethylenes are rearranged to give diarylacetylenes in the presence of strong bases.

Tolans of the formula I can also be prepared by brominating the corresponding stilbenes, followed by dehydrohalogenation. Use can be made here of variants of this reaction which are known per se, but are not mentioned here in greater detail.

Ethers of the formula I are obtainable by etherification of corresponding hydroxyl compounds, preferably corresponding phenols, where the hydroxyl compound is advantageously firstly converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

In order to prepare the laterally substituted fluorine or chlorine compounds of the formula I, corresponding aniline derivatives can be reacted with sodium nitrite and either with tetrafluoroboric acid (in order to introduce an F atom) or with copper(I) chloride (in order to introduce a Cl atom) to give the diazonium salts, which are then thermally decomposed at temperatures of 100–140° C.

The linking of an aromatic ring to a non-aromatic ring or of two non-aromatic rings is preferably obtained by condensation of an organolithium or organomagnesium compound with a ketone if an aliphatic group $Z^1$ or $Z^3$ is intended to be present between the rings.

The organometallic compounds are prepared, for example, by metal-halogen exchange (for example in accordance with Org. React. 6, 339–366 (1951)) between the corresponding halogen compound and an organolithium compound, preferably tert-butyllithium or lithium naphthalenide, or by reaction with magnesium turnings.

The linking of two aromatic rings is preferably carried out by Friedel-Crafts alkylation or acylation by reacting the corresponding aromatic compounds with Lewis acid catalysis. Suitable Lewis acids are, for example, $SnCl_4$, $ZnCl_2$, $AlCl_3$ and $TiCl_4$.

Furthermore, the linking of two aromaticnrings can be carried out by the Ullmann reaction (for example Synthesis 1974, 9) between aryl iodides and copper iodide, but preferably between an arylcopper compound and an aryl iodide, or by the Gomberg-Bachmann reaction between an aryldiazonium salt and the corresponding aromatic compound (for example Org. React. 2, 224 (1944)).

The tolans of the formula I are prepared, for example, by reaction of the corresponding aryl halides with an acetylide in a basic solvent with transition-metal catalysis; palladium catalysts can preferably be used here, in particular a mixture of bis(triphenylphosphine)palladium(II) chloride and copper iodide in piperidine as solvent.

In addition, the compounds of the formula I can be prepared by reducing a compound which conforms to the formula I, but contains one or more reducible groups and/or C—C bonds in place of H atoms.

Suitable reducible groups are preferably carbonyl groups, in particular keto groups, furthermore, for example, free or esterified hydroxyl groups or aromatically bound halogen atoms. Preferred starting materials for the reduction are compounds conforming to the formula I, but which contain a cyclohexene ring or cyclohexanone ring instead of a cyclohexane ring and/or contain a —$CH_2CH_2$— group instead of a —CH═CH— group and/or contain a —CO— group instead of a —$CH_2$— group and/or contain a free or functionally (for example in the form of its p-toluenesulfonate) modified OH group instead of an H atom.

The reduction can be carried out, for example, by catalytic hydrogenation at temperatures between about 0° C. and about 200° C. and pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which can be employed in the form of oxides (for example $PtO_2$ or PdO), on a support (for example Pd on carbon, calcium carbonate or strontium carbonate) or in finely divided form.

Ketones can also be reduced to the corresponding compounds of the formula I containing alkyl groups and/or —$CH_2CH_2$— bridges by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.).

Furthermore, reductions with complex hydrides are possible. For example, arylsulfonyloxy groups can be removed reductively using $LiAlH_4$, in particular p-toluenesulfonyloxymethyl groups can be reduced to methyl groups, advantageously in an inert solvent, such as diethyl ether or THF, at temperatures between about 0 and 100° C. Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention.

These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-di-cyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae 1, 2, 3, 4 and 5:

R'-L-E-R"      1

R'-L-COO-E-R"  2

R'-L-OOC-E-R"  3

R'-L-CH$_2$CH$_2$-E-R"  4

R'-L-C≡C-E-R"  5

In the formulae 1, 2, 3, 4 and 5, L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R" are each, independently of one another, alkyl, alkenyl, alkoxy, alkoxyalkyl, alkenyloxy or alkanoyloxy having up to 8 carbon atoms, —F, —Cl, —CN, —NCS or —(O)$_i$CH$_{3-(k+l)}$F$_k$Cl$_l$, where i is 0 or 1 and k and l are 1, 2 or 3.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is known as group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are referred to by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

Besides the preferred compounds of groups A, B and C, other compounds of the formulae 1, 2, 3, 4 and 5 having other variants of the proposed substituents are also customary all these substances are obtainable by methods which are known from the literature or analogously thereto.

Besides the compounds of the formula I according to the invention, the media according to the invention preferably comprise one or more compounds selected from group A and/or group B and/or group C. The proportions by weight of the compounds from these groups in the media according to the invention are preferably

| group A: | from 0 to 90%, preferably from 20 to 90%, in particular from 30 to 90% |
|---|---|
| group B: | from 0 to 80%, preferably from 10 to 80%, in particular from 10 to 65% |
| group C: | from 0 to 80%, preferably from 5 to 80%, in particular from 5 to 50%, | the sum of the proportions by weight of the group A and/or B and/or C compounds present in the respective media according to the invention preferably being 5%–90% and in particular from 10% to 90%.

The media according to the invention preferably comprise from 1 to 40%, particularly preferably from 5 to 30%, of the compounds according to the invention. Preference is furthermore given to media comprising more than 40%, in particular from 45 to 90%, of compounds according to the invention. The media preferably comprise three, four or five compounds according to the invention.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The individual compounds added are employed in concentrations of from 0.01 to 6%, preferably from 0.1 to 3%. However, the concentration figures for the other constituents of the liquid-crystal mixtures, i.e. of the liquid-crystalline or mesogenic compounds, are indicated without taking into account the concentration of these additives.

The following examples are intended to explain the invention without limiting it. Above and below, percentages are per cent by weight all temperatures are given in degrees Celsius.

"Conventional work-up" means that water is added if desired, the mixture is extracted with methylene chloride, diethyl ether or toluene, the phases are separated, the organic phase is dried and evaporated, and the product is purified by distillation under reduced pressure or crystallisation and/or chromatography.

The following abbreviations are used above and below:

| | |
|---|---|
| DAST | diethylaminosulfur trifluoride |
| DMF | dimethylformamide |
| KOtBu | potassium tertiary-butoxide |
| n-BuLi | n-butyllithium |
| THF | tetrahydrofuran |

WORKING EXAMPLES

1. Synthesis of compound 22

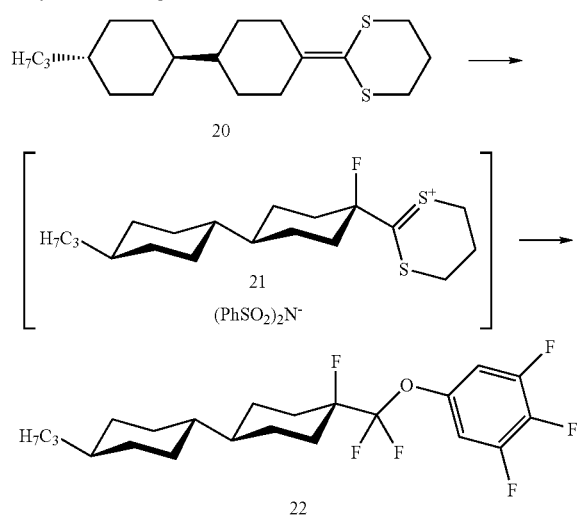

50 mmol of solid PhSO$_2$NFSO$_2$Ph (S. D. Taylor, C. C. Kotoris, G. Hum, Tetrahedron 55, 1999, 12431–12477) are added in portions with ice-cooling to a solution of 50 mmol of the ketene dithioketal 20 (obtainable, for example, as described by P. Kirsch, M. Bremer, A. Taugerbeck, T. Wallmichrath, Angew. Chem. 113, 2001, 1528–1532) in 400 ml of CH$_2$Cl$_2$. The mixture is stirred at about 20° C. for a further 30 minutes and cooled to –70° C., and firstly a solution of 75 mmol of 3,4,5-trifluorophenol and 100 mmol of triethylamine in 100 ml of CH$_2$Cl$_2$ is added. 250 mmol of triethylamine tris(hydrofluoride) are then added, and, after a further 5 minutes, 250 mmol of bromine are added dropwise. The mixture is stirred at –700° C. for a further 1 hour, then allowed to warm to –20° C. and poured onto ice. The aqueous work-up is carried out in the conventional manner. The product is chromatographed (n-heptane; silica gel) and recrystallised a number of times from n-heptane at –20° C.: Δ∈=14.6, Δn=0.087.

2. Synthesis of compound 28

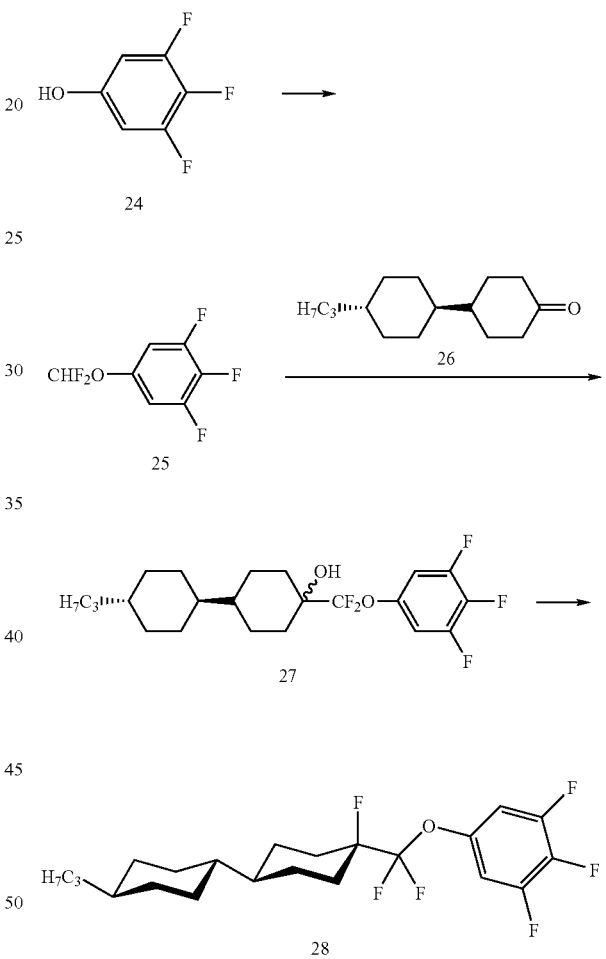

100 mmol of KOtBu are added to a solution of 100 mmol of 3,4,5-trifluorophenol in 400 ml of THF at –20° C. in an autoclave. 400 mmol of CHClF$_2$ are subsequently condensed in, and the mixture is stirred at about 20° C. for 18 hours. The mixture is subjected to aqueous work-up, and the intermediate 25 is purified by distillation.

Firstly, KOtBu is added in small portions at –20° C. to a solution of 50 mmol of the intermediate 25 in 300 ml of DMF. After 15 minutes, 80 mmol of 4-(4-propylcyclohexyl) cyclohexanone 26 are added. The mixture is stirred at about 20° C. for 18 hours. The mixture is subjected to aqueous work-up, and the intermediate 27 is chromatographed on silica gel using heptane/ethyl acetate 4:1.

6 mmol of DAST are added dropwise at −80° C. to a solution of 5 mmol of the intermediate 27 in 30 ml of dichloromethane. The mixture is allowed to warm to 0° C. over the course of 2 hours, subjected to aqueous work-up, chromatographed (SiO$_2$; heptane) and crystallised three times from heptane.

3. Synthesis of compound 33

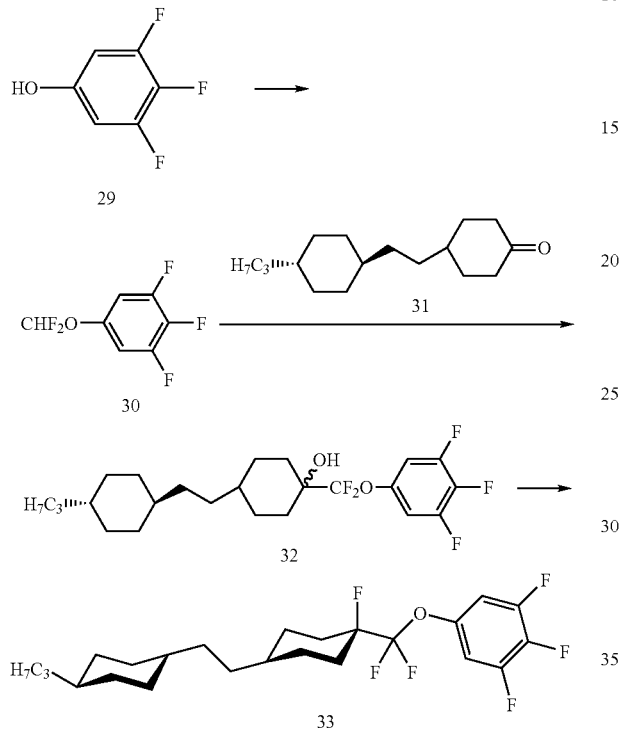

Compound 33 according to the invention can be prepared analogously to the previous working example using 80 mmol of 4-(2-(4-propylcyclohexyl)ethylene)cyclohexanone of the formula 31 instead of 4-(4-propylcyclohexyl)cyclohexanone.

In the same way, compound 34 is obtainable using 4-(2-(4-propylcyclohexyl)tetrafluoroethylene)cyclohexanone.

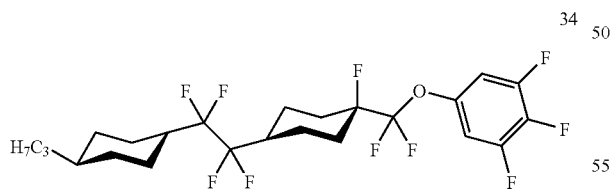

Compounds of the following formulae are obtained analogously to the previous examples:

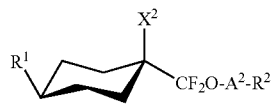

| | $R^1$ | $X^2$ | -$A^2$-$R^2$ |
|---|---|---|---|
| (50) | —$C_3H_7$ | —F | ⟨⟩—F |
| (51) | —$C_5H_{11}$ | —F | ⟨⟩—F |
| (52) | CH=CH$_2$ | —F | ⟨⟩—F |
| (53) | —$C_3H_7$ | —F | ⟨⟩—CH$_3$ |
| (54) | —$C_5H_{11}$ | —F | ⟨⟩—CH$_3$ |
| (55) | CH=CH$_2$ | —F | ⟨⟩—CH$_3$ |
| (56) | —$C_3H_7$ | —F | ⟨⟩—CF$_3$ |
| (57) | —$C_5H_{11}$ | —F | ⟨⟩—CF$_3$ |
| (58) | CH=CH$_2$ | —F | ⟨⟩—CF$_3$ |
| (59) | —$C_3H_7$ | —F | ⟨⟩—OCH$_3$ |
| (60) | —$C_5H_{11}$ | —F | ⟨⟩—OCH$_3$ |
| (61) | CH=CH$_2$ | —F | ⟨⟩—OCH$_3$ |
| (62) | —$C_3H_7$ | —F | ⟨⟩—OCHF$_2$ |
| (63) | —$C_5H_{11}$ | —F | ⟨⟩—OCHF$_2$ |
| (64) | CH=CH$_2$ | —F | ⟨⟩—OCHF$_2$ |

| | R¹ | X² | -A²-R² |
|---|---|---|---|
| (65) | —C₃H₇ | —F |  -OCF₃ |
| (66) | —C₅H₁₁ | —F | 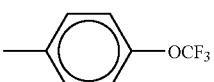 -OCF₃ |
| (67) | CH=CH₂ | —F |  -OCF₃ |
| (68) | —C₃H₇ | —F |  F, F |
| (69) | —C₅H₁₁ | —F | 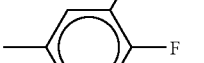 F, F |
| (70) | CH=CH₂ | —F | 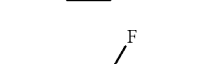 F, F |
| (71) | —C₃H₇ | —F |  F, CH₃ |
| (72) | —C₅H₁₁ | —F | 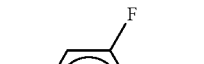 F, CH₃ |
| (73) | CH=CH₂ | —F |  F, CH₃ |
| (74) | —C₃H₇ | —F | 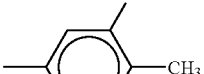 F, CF₃ |
| (75) | —C₅H₁₁ | —F |  F, CF₃ |
| (76) | CH=CH₂ | —F | 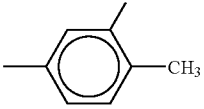 F, CF₃ |
| | R¹ | X² | -A²-R² |
|---|---|---|---|
| (77) | —C₃H₇ | —F | 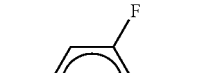 F, OCH₃ |
| (78) | —C₅H₁₁ | —F | 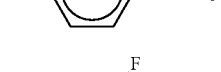 F, OCH₃ |
| (79) | CH=CH₂ | —F | 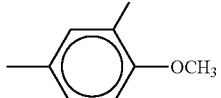 F, OCH₃ |
| (80) | —C₃H₇ | —F | 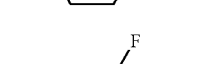 F, OCF₃ |
| (81) | —C₅H₁₁ | —F | 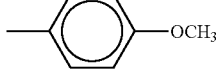 F, OCF₃ |
| (82) | CH=CH₂ | —F | 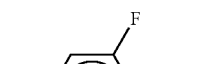 F, OCF₃ |
| (83) | —C₃H₇ | —F | 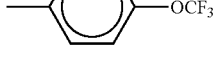 F, F, F |
| (84) | —C₅H₁₁ | —F | 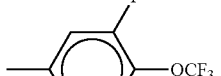 F, F, F |
| (85) | CH=CH₂ | —F |  F, F, F |
| (86) | —C₃H₇ | —F | 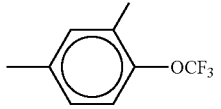 F, CH₃, F |

-continued
|  | R¹ | X² | -A²-R² |
|---|---|---|---|
| (87) | —C₅H₁₁ | —F | 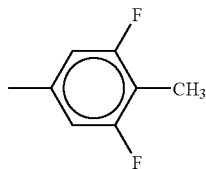 |
| (88) | CH=CH₂ | —F | 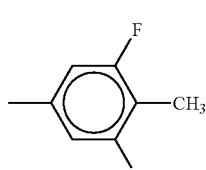 |
| (89) | —C₃H₇ | —F | 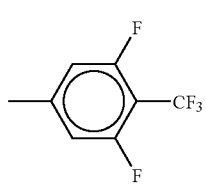 |
| (90) | —C₅H₇ | —F | 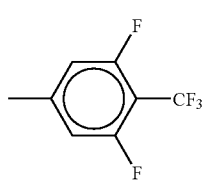 |
| (91) | CH=CH₂ | —F | 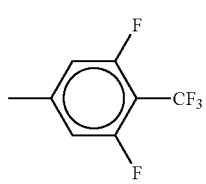 |
| (92) | —C₃H₇ | —F | 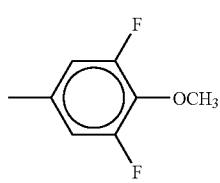 |
| (93) | —C₅H₁₁ | —F | 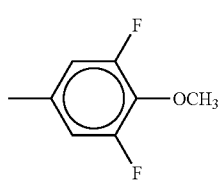 |
| (94) | CH=CH₂ | —F | 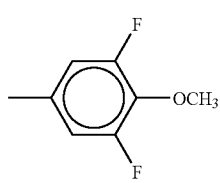 |
-continued
|  | R¹ | X² | -A²-R² |
|---|---|---|---|
| (95) | —C₃H₇ | —F | 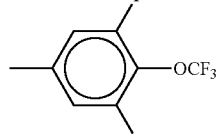 |
| (96) | —C₅H₁₁ | —F | 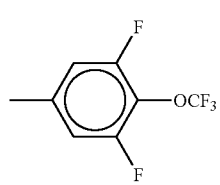 |
| (97) | CH=CH₂ | —F | 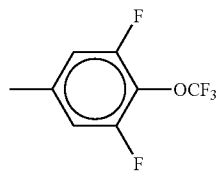 |
| (98) | —C₃H₇ | —F | 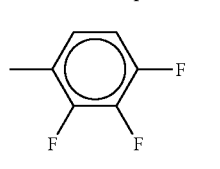 |
| (99) | —C₅H₁₁ | —F | 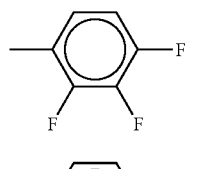 |
| (100) | CH=CH₂ | —F | 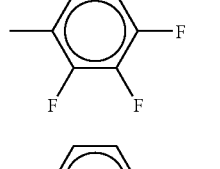 |
| (101) | —C₃H₇ | —F | 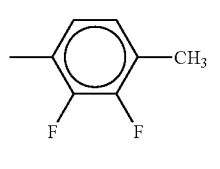 |
| (102) | —C₅H₁₁ | —F | 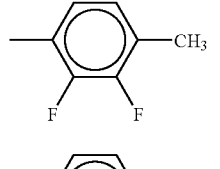 |
| (103) | CH=CH₂ | —F | 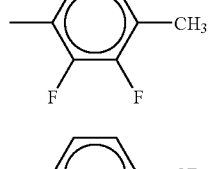 |
| (104) | —C₃H₇ | —F | 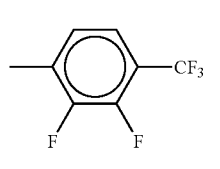 |

-continued
| | R¹ | X² | -A²-R² |
|---|---|---|---|
| (105) | —C₅H₁₁ | —F | 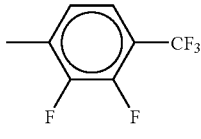 |
| (106) | CH=CH₂ | —F | 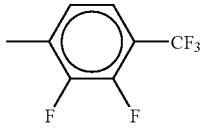 |
| (107) | —C₃H₇ | —F | 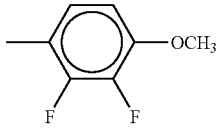 |
| (108) | —C₅H₁₁ | —F | 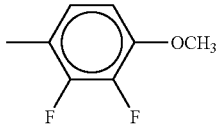 |
| (109) | CH=CH₂ | —F | 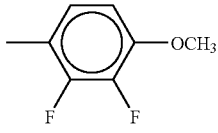 |
| (110) | —C₃H₇ | —F | 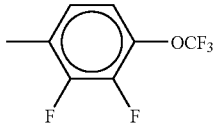 |
| (111) | —C₅H₁₁ | —F | 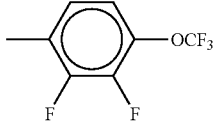 |
| (112) | CH=CH₂ | —F | 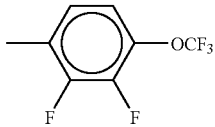 |
| (113) | —C₃H₇ | —CH₃ | 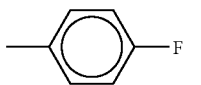 |
| (114) | —C₅H₁₁ | —CH₃ | 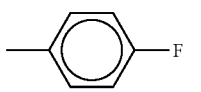 |
| (115) | CH=CH₂ | —CH₃ | 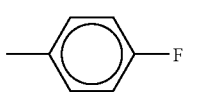 |
| (116) | —C₃H₇ | —CH₃ | 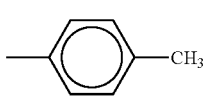 |
-continued
| | R¹ | X² | -A²-R² |
|---|---|---|---|
| (117) | —C₅H₁₁ | —CH₃ |  |
| (118) | CH=CH₂ | —CH₃ | 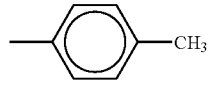 |
| (119) | —C₃H₇ | —CH₃ | 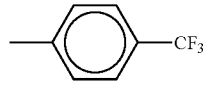 |
| (120) | —C₅H₁₁ | —CH₃ | 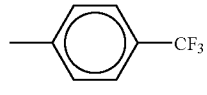 |
| (121) | CH=CH₂ | —CH₃ |  |
| (122) | —C₃H₇ | —CH₃ |  |
| (123) | —C₅H₁₁ | —CH₃ |  |
| (124) | CH=CH₂ | —CH₃ |  |
| (125) | —C₃H₇ | —CH₃ |  |
| (126) | —C₃H₇ | —CH₃ |  |
| (127) | CH=CH₂ | —CH₃ | 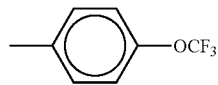 |
| (128) | —C₃H₇ | —CH₃ | 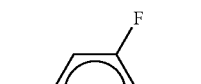 |
| (129) | —C₅H₁₁ | —CH₃ |  |
| (130) | CH=CH₂ | —CH₃ | 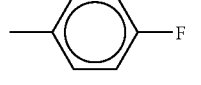 |

-continued
| | R¹ | X² | -A²-R² |
|---|---|---|---|
| (131) | —C₃H₇ | —CH₃ | 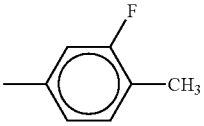 |
| (132) | —C₅H₁₁ | —CH₃ | 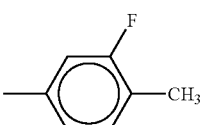 |
| (133) | CH=CH₂ | —CH₃ | 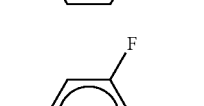 |
| (134) | —C₃H₇ | —CH₃ | 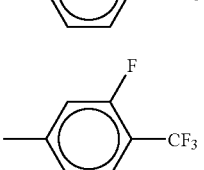 |
| (135) | —C₅H₁₁ | —CH₃ | 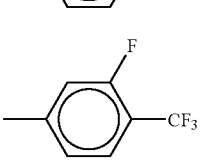 |
| (136) | CH=CH₂ | —CH₃ | 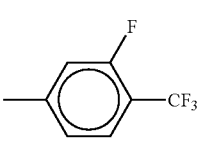 |
| (137) | —C₃H₇ | —CH₃ | 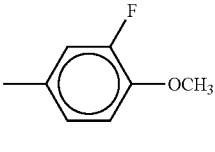 |
| (138) | —C₅H₁₁ | —CH₃ | 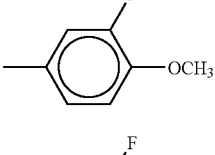 |
| (139) | CH=CH₂ | —CH₃ | 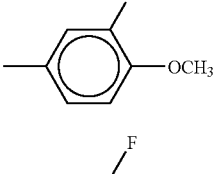 |
| (140) | —C₃H₇ | —CH₃ | 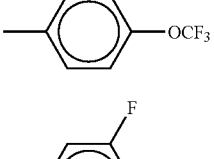 |
| (141) | —C₅H₁₁ | —CH₃ | 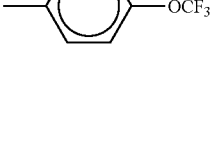 |
-continued
| | R¹ | X² | -A²-R² |
|---|---|---|---|
| (142) | CH=CH₂ | —CH₃ | 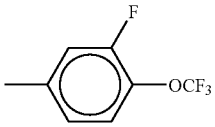 |
| (143) | —C₃H₇ | —CH₃ | 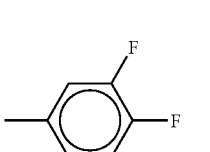 |
| (144) | —C₅H₁₁ | —CH₃ | 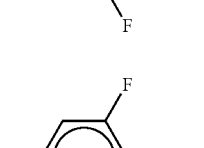 |
| (145) | CH=CH₂ | —CH₃ | 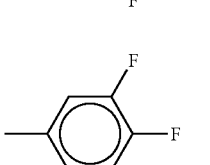 |
| (146) | —C₃H₇ | —CH₃ | 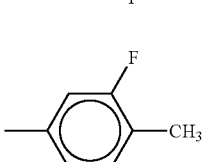 |
| (147) | —C₅H₁₁ | —CH₃ | 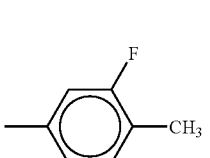 |
| (148) | CH=CH₂ | —CH₃ | 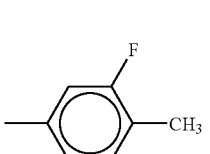 |
| (149) | —C₃H₇ | —CH₃ | 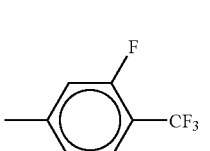 |

|  | R¹ | X² | -A²-R² |
|---|---|---|---|
| (150) | —C₅H₁₁ | —CH₃ | 2,6-difluoro-4-(CF₃)phenyl |
| (151) | CH=CH₂ | —CH₃ | 2,6-difluoro-4-(CF₃)phenyl |
| (152) | —C₃H₇ | —CH₃ | 2,6-difluoro-4-(OCH₃)phenyl |
| (153) | —C₅H₁₁ | —CH₃ | 2,6-difluoro-4-(OCH₃)phenyl |
| (154) | CH=CH₂ | —CH₃ | 2,6-difluoro-4-(OCH₃)phenyl |
| (155) | —C₃H₇ | —CH₃ | 2,6-difluoro-4-(OCF₃)phenyl |
| (156) | —C₅H₁₁ | —CH₃ | 2,6-difluoro-4-(OCF₃)phenyl |
| (157) | CH=CH₂ | —CH₃ | 2,6-difluoro-4-(OCF₃)phenyl |
| (158) | —C₃H₇ | —CH₃ | 2,3,4-trifluorophenyl |
| (159) | —C₅H₁₁ | —CH₃ | 2,3,4-trifluorophenyl |
| (160) | CH=CH₂ | —CH₃ | 2,3,4-trifluorophenyl |
| (161) | —C₃H₇ | —CH₃ | 2,3-difluoro-4-(CH₃)phenyl |
| (162) | —C₅H₁₁ | —CH₃ | 2,3-difluoro-4-(CH₃)phenyl |
| (163) | CH=CH₂ | —CH₃ | 2,3-difluoro-4-(CH₃)phenyl |
| (164) | —C₃H₇ | —CH₃ | 2,3-difluoro-4-(CF₃)phenyl |
| (165) | —C₅H₁₁ | —CH₃ | 2,3-difluoro-4-(CF₃)phenyl |
| (166) | CH=CH₂ | —CH₃ | 2,3-difluoro-4-(CF₃)phenyl |
| (167) | —C₃H₇ | —CH₃ | 2,3-difluoro-4-(OCH₃)phenyl |
| (168) | —C₅H₁₁ | —CH₃ | 2,3-difluoro-4-(OCH₃)phenyl |

-continued
| | R¹ | X² | -A²-R² |
|---|---|---|---|
| (169) | CH=CH₂ | —CH₃ | 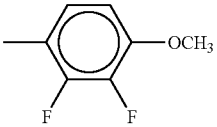 |
| (170) | —C₃H₇ | —CH₃ | 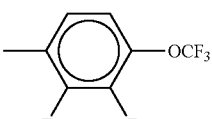 |
| (171) | —C₅H₁₁ | —CH₃ | 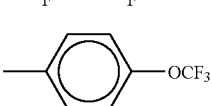 |
| (172) | CH=CH₂ | —CH₃ | 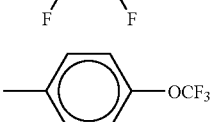 |
| (173) | —C₃H₇ | —CF₃ | 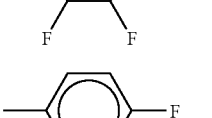 |
| (174) | —C₅H₁₁ | —CF₃ | 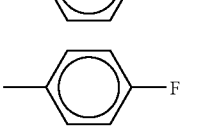 |
| (175) | CH=CH₂ | —CF₃ | 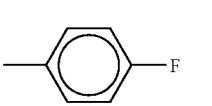 |
| (176) | —C₃H₇ | —CF₃ | 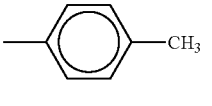 |
| (177) | —C₅H₁₁ | —CF₃ |  |
| (178) | CH=CH₂ | —CF₃ |  |
| (179) | —C₃H₇ | —CF₃ | 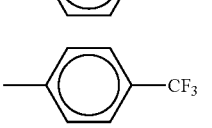 |
| (180) | —C₅H₁₁ | —CF₃ | 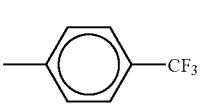 |
| (181) | CH=CH₂ | —CF₃ | 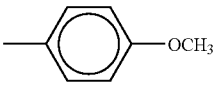 |
| (182) | —C₃H₇ | —CF₃ |  |
-continued
| | R¹ | X² | -A²-R² |
|---|---|---|---|
| (183) | —C₅H₁₁ | —CF₃ | 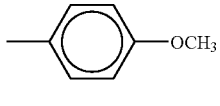 |
| (184) | CH=CH₂ | —CF₃ | 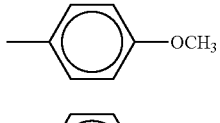 |
| (185) | —C₃H₇ | —CF₃ |  |
| (186) | —C₅H₁₁ | —CF₃ | 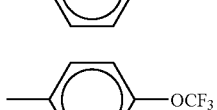 |
| (187) | CH=CH₂ | —CF₃ | 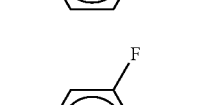 |
| (188) | —C₃H₇ | —CF₃ | 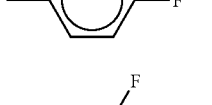 |
| (189) | —C₅H₁₁ | —CF₃ | 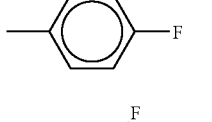 |
| (190) | CH=CH₂ | —CF₃ | 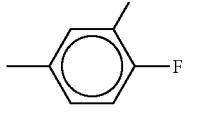 |
| (191) | —C₃H₇ | —CF₃ | 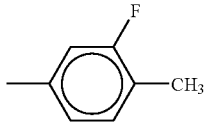 |
| (192) | —C₅H₁₁ | —CF₃ | 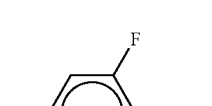 |
| (193) | CH=CH₂ | —CF₃ | 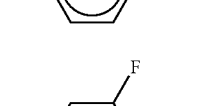 |
| (194) | —C₃H₇ | —CF₃ | 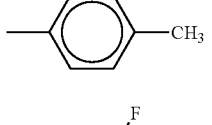 |

-continued

| | R¹ | X² | -A²-R² |
|---|---|---|---|
| (195) | —C₅H₁₁ | —CF₃ | 2-F, 4-CF₃ phenyl |
| (196) | CH=CH₂ | —CF₃ | 2-F, 4-CF₃ phenyl |
| (197) | —C₃H₇ | —CF₃ | 2-F, 4-OCH₃ phenyl |
| (198) | —C₅H₁₁ | —CF₃ | 2-F, 4-OCH₃ phenyl |
| (199) | CH=CH₂ | —CF₃ | 2-F, 4-OCH₃ phenyl |
| (200) | —C₃H₇ | —CF₃ | 2-F, 4-OCF₃ phenyl |
| (201) | —C₅H₁₁ | —CF₃ | 2-F, 4-OCF₃ phenyl |
| (202) | CH=CH₂ | —CF₃ | 2-F, 4-OCF₃ phenyl |
| (203) | —C₃H₇ | —CF₃ | 3,4,5-triF phenyl |
| (204) | —C₅H₁₁ | —CF₃ | 3,4,5-triF phenyl |
| (205) | CH=CH₂ | —CF₃ | 3,4,5-triF phenyl |
| (206) | —C₃H₇ | —CF₃ | 3,5-diF, 4-CH₃ phenyl |
| (207) | —C₅H₁₁ | —CF₃ | 3,5-diF, 4-CH₃ phenyl |
| (208) | CH=CH₂ | —CF₃ | 3,5-diF, 4-CH₃ phenyl |
| (209) | —C₃H₇ | —CF₃ | 3,5-diF, 4-CF₃ phenyl |
| (210) | —C₅H₁₁ | —CF₃ | 3,5-diF, 4-CF₃ phenyl |
| (211) | CH=CH₂ | —CF₃ | 3,5-diF, 4-CF₃ phenyl |
| (212) | —C₃H₇ | —CF₃ | 3,5-diF, 4-OCH₃ phenyl |

-continued

| | R¹ | X² | -A²-R² |
|---|---|---|---|
| (213) | —C₅H₁₁ | —CF₃ | 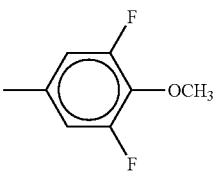 2,6-difluoro-4-OCH₃ phenyl |
| (214) | CH=CH₂ | —CF₃ | 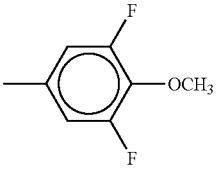 2,6-difluoro-4-OCH₃ phenyl |
| (215) | —C₃H₇ | —CF₃ | 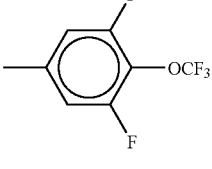 2,6-difluoro-4-OCF₃ phenyl |
| (216) | —C₅H₁₁ | —CF₃ | 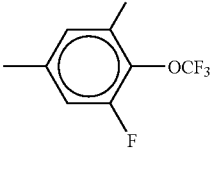 2,6-difluoro-4-OCF₃ phenyl |
| (217) | CH=CH₂ | —CF₃ | 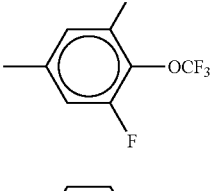 2,6-difluoro-4-OCF₃ phenyl |
| (218) | —C₃H₇ | —CF₃ | 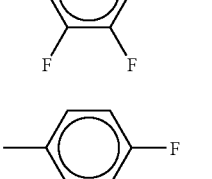 2,3,4-trifluoro phenyl |
| (219) | —C₅H₁₁ | —CF₃ | 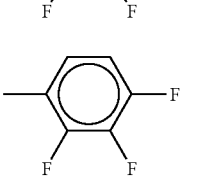 2,3,4-trifluoro phenyl |
| (220) | CH=CH₂ | —CF₃ | 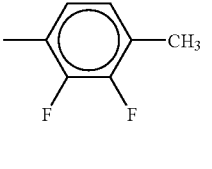 2,3,4-trifluoro phenyl |
| (221) | —C₃H₇ | —CF₃ |  2,3-difluoro-4-CH₃ phenyl |

-continued

| | R¹ | X² | -A²-R² |
|---|---|---|---|
| (222) | —C₅H₁₁ | —CF₃ | 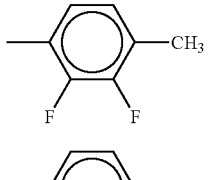 2,3-difluoro-4-CH₃ phenyl |
| (223) | CH=CH₂ | —CF₃ | 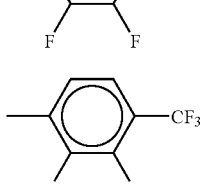 2,3-difluoro-4-CH₃ phenyl |
| (224) | —C₃H₇ | —CF₃ | 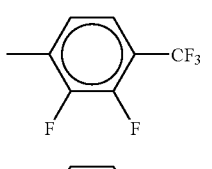 2,3-difluoro-4-CF₃ phenyl |
| (225) | —C₅H₁₁ | —CF₃ | 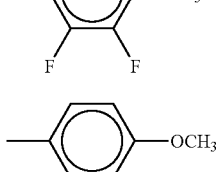 2,3-difluoro-4-CF₃ phenyl |
| (226) | CH=CH₂ | —CF₃ | 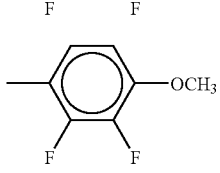 2,3-difluoro-4-CF₃ phenyl |
| (227) | —C₃H₇ | —CF₃ | 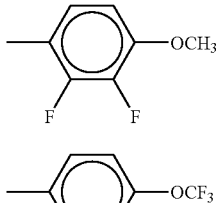 2,3-difluoro-4-OCH₃ phenyl |
| (228) | —C₅H₁₁ | —CF₃ | 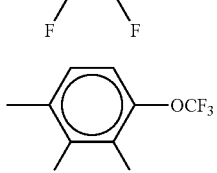 2,3-difluoro-4-OCH₃ phenyl |
| (229) | CH=CH₂ | —CF₃ | 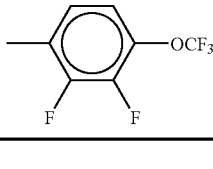 2,3-difluoro-4-OCH₃ phenyl |
| (230) | —C₃H₇ | —CF₃ |  2,3-difluoro-4-OCF₃ phenyl |
| (231) | —C₅H₁₁ | —CF₃ | 2,3-difluoro-4-OCF₃ phenyl |
| (232) | CH=CH₂ | —CF₃ | 2,3-difluoro-4-OCF₃ phenyl |

Furthermore, compounds of the formulae shown below are obtained analogously to the previous examples:

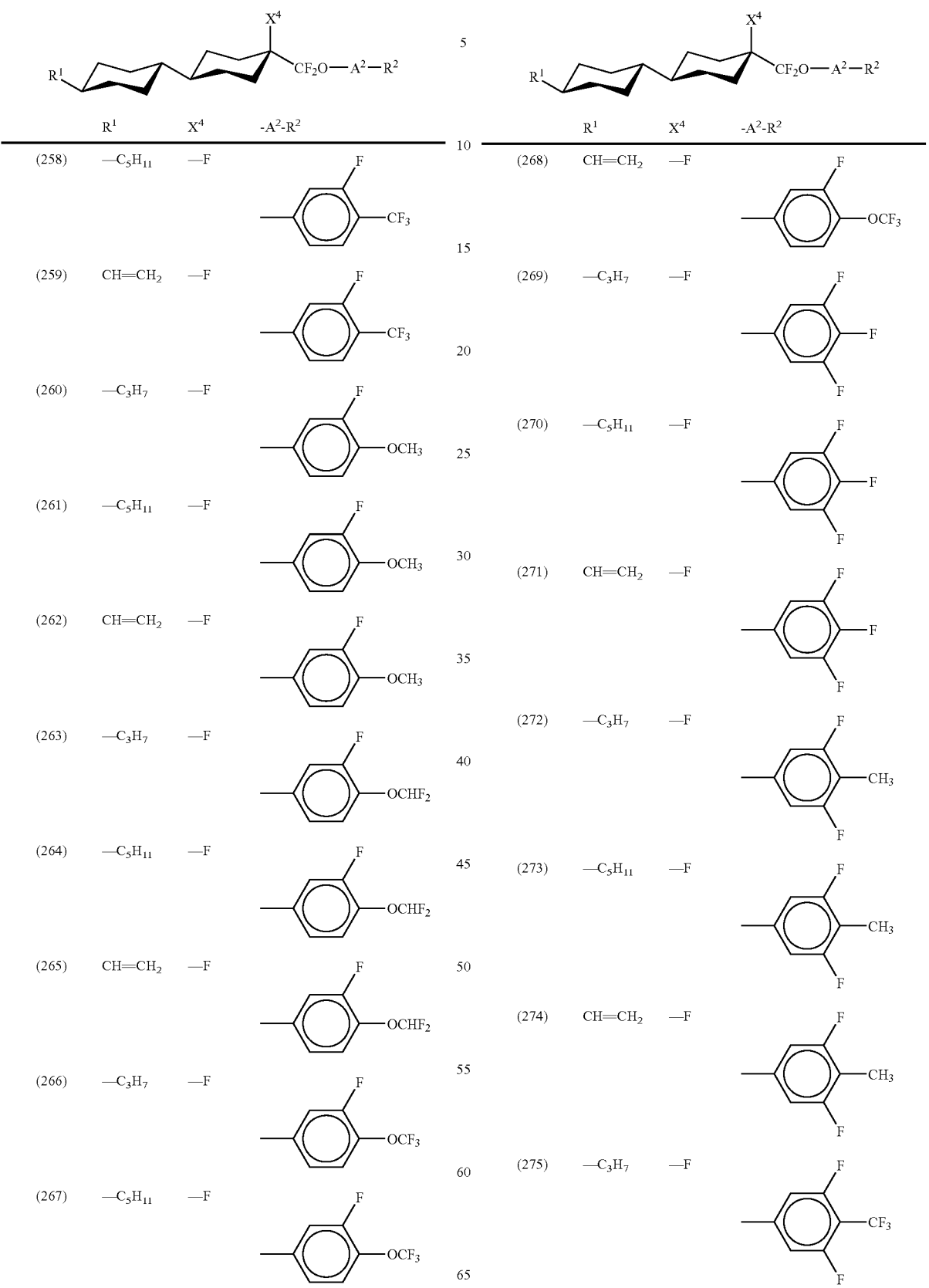

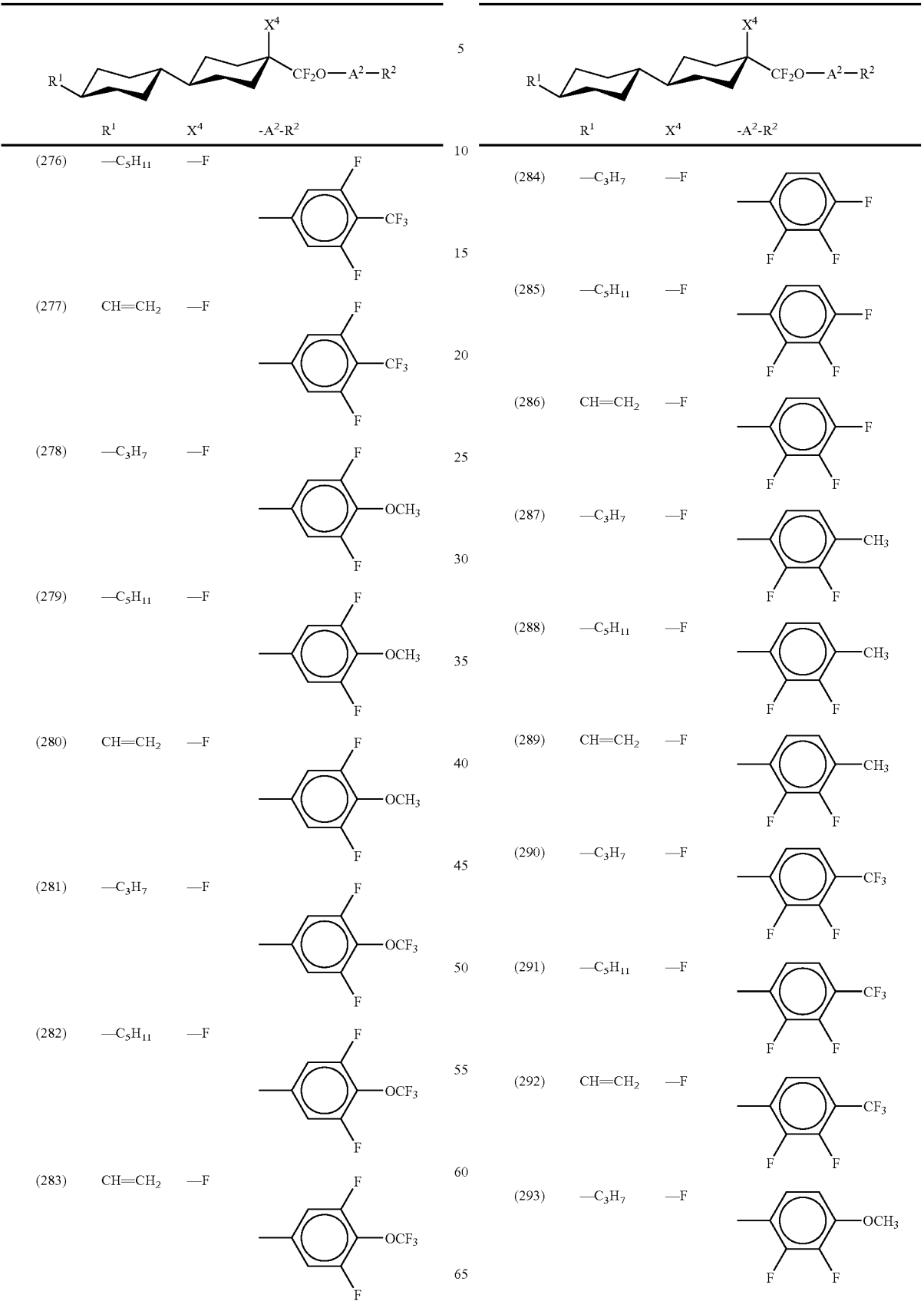

-continued
| | R¹ | X⁴ | -A²-R² |
|---|---|---|---|
| (294) | —C₅H₁₁ | —F |  |
| (295) | CH=CH₂ | —F | 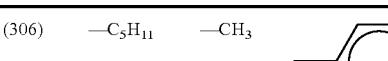 |
| (296) | —C₃H₇ | —F | 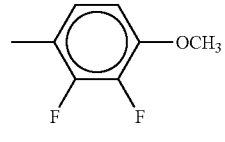 |
| (297) | —C₅H₁₁ | —F | 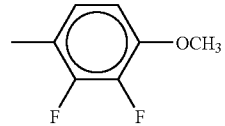 |
| (298) | CH=CH₂ | —F | 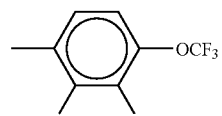 |
| (299) | —C₃H₇ | —CH₃ | 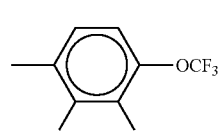 |
| (300) | —C₅H₁₁ | —CH₃ | |
| (301) | CH=CH₂ | —CH₃ | |
| (302) | —C₃H₇ | —CH₃ | |
| (303) | —C₅H₁₁ | —CH₃ | |
| (304) | CH=CH₂ | —CH₃ | |
| (305) | —C₃H₇ | —CH₃ | |
-continued
| | R¹ | X⁴ | -A²-R² |
|---|---|---|---|
| (306) | —C₅H₁₁ | —CH₃ | 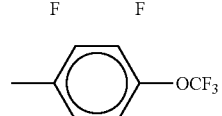 |
| (307) | CH=CH₂ | —CH₃ | |
| (308) | —C₃H₇ | —CH₃ | 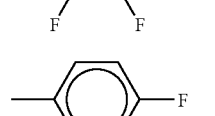 |
| (309) | —C₅H₁₁ | —CH₃ | |
| (310) | CH=CH₂ | —CH₃ | |
| (311) | —C₃H₇ | —CH₃ | 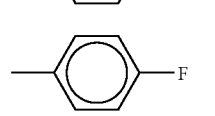 |
| (312) | —C₅H₁₁ | —CH₃ | |
| (313) | CH=CH₂ | —CH₃ | |
| (314) | —C₃H₇ | —CH₃ | 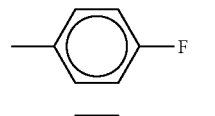 |
| (315) | —C₅H₁₁ | —CH₃ | 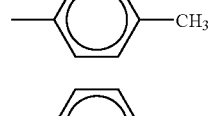 |
| (316) | CH=CH₂ | —CH₃ | 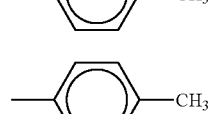 |
| (317) | —C₃H₇ | —CH₃ | 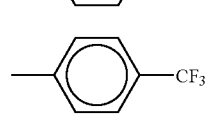 |

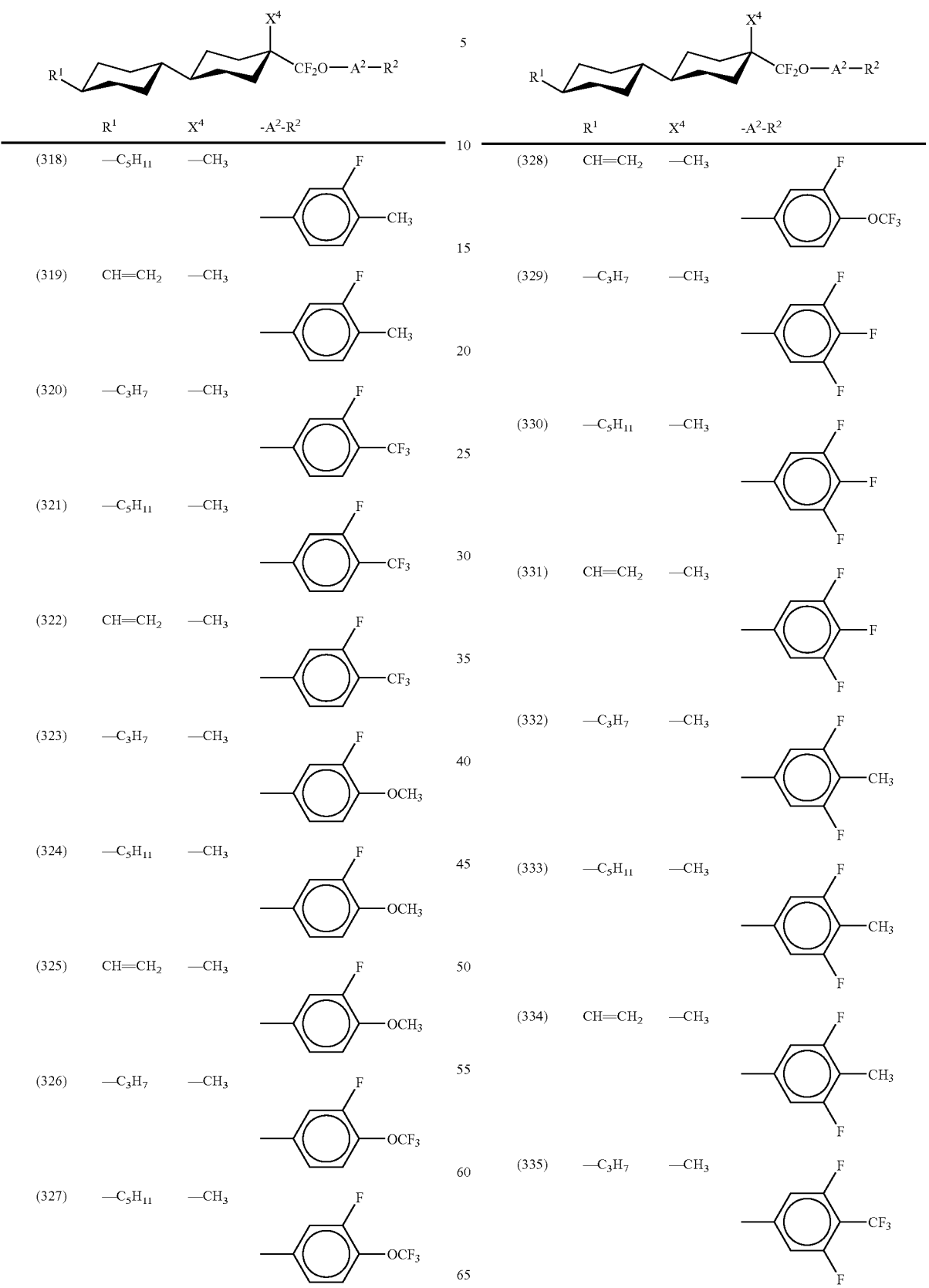

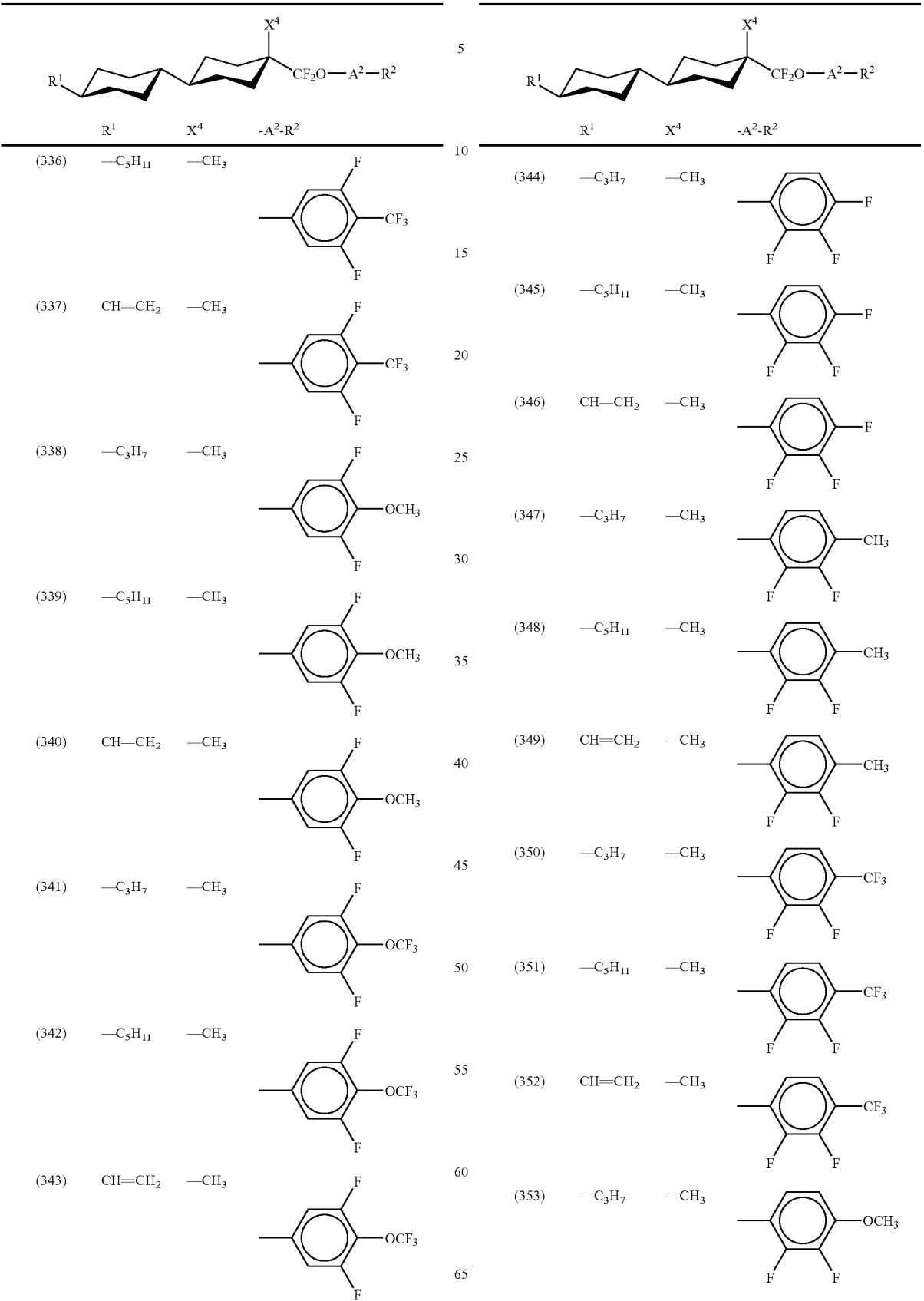

-continued

R¹-[cyclohexyl]-[cyclohexyl](X⁴)-CF₂O-A²-R²

| | R¹ | X⁴ | -A²-R² |
|---|---|---|---|
| (354) | —C₅H₁₁ | —CH₃ | 4-OCH₃-2,3-difluorophenyl |
| (355) | CH=CH₂ | —CH₃ | 4-OCH₃-2,3-difluorophenyl |
| (356) | —C₃H₇ | —CH₃ | 4-OCF₃-2,3-difluorophenyl |
| (357) | —C₅H₁₁ | —CH₃ | 4-OCF₃-2,3-difluorophenyl |
| (358) | CH=CH₂ | —CH₃ | 4-OCF₃-2,3-difluorophenyl |
| (359) | —C₃H₇ | —CF₃ | 4-F-phenyl |
| (360) | —C₅H₁₁ | —CF₃ | 4-F-phenyl |
| (361) | CH=CH₂ | —CF₃ | 4-F-phenyl |
| (362) | —C₃H₇ | —CF₃ | 4-CH₃-phenyl |
| (363) | —C₅H₁₁ | —CF₃ | 4-CH₃-phenyl |
| (364) | CH=CH₂ | —CF₃ | 4-CH₃-phenyl |
| (365) | —C₃H₇ | —CF₃ | 4-CF₃-phenyl |
| (366) | —C₅H₁₁ | —CF₃ | 4-CF₃-phenyl |
| (367) | CH=CH₂ | —CF₃ | 4-CF₃-phenyl |
| (368) | —C₃H₇ | —CF₃ | 4-OCH₃-phenyl |
| (369) | —C₅H₁₁ | —CF₃ | 4-OCH₃-phenyl |
| (370) | CH=CH₂ | —CF₃ | 4-OCH₃-phenyl |
| (371) | —C₃H₇ | —CF₃ | 4-OCF₃-phenyl |
| (372) | —C₅H₁₁ | —CF₃ | 4-OCF₃-phenyl |
| (373) | CH=CH₂ | —CF₃ | 4-OCF₃-phenyl |
| (374) | —C₃H₇ | —CF₃ | 3,4-difluorophenyl |
| (375) | —C₅H₁₁ | —CF₃ | 3,4-difluorophenyl |
| (376) | CH=CH₂ | —CF₃ | 3,4-difluorophenyl |
| (377) | —C₃H₇ | —CF₃ | 3-F-4-CH₃-phenyl |

-continued

![structure: R¹-cyclohexyl-cyclohexyl(X⁴)(CF₂O-A²-R²)]

| | R¹ | X⁴ | -A²-R² |
|---|---|---|---|
| (378) | —C₅H₁₁ | —CF₃ | 2-F, 3-CH₃ phenyl |
| (379) | CH=CH₂ | —CF₃ | 2-F, 3-CH₃ phenyl |
| (380) | —C₃H₇ | —CF₃ | 2-F, 3-CF₃ phenyl |
| (381) | —C₅H₁₁ | —CF₃ | 2-F, 3-CF₃ phenyl |
| (382) | CH=CH₂ | —CF₃ | 2-F, 3-CF₃ phenyl |
| (383) | —C₃H₇ | —CF₃ | 2-F, 3-OCH₃ phenyl |
| (384) | —C₅H₁₁ | —CF₃ | 2-F, 3-OCH₃ phenyl |
| (385) | CH=CH₂ | —CF₃ | 2-F, 3-OCH₃ phenyl |
| (386) | —C₃H₇ | —CF₃ | 2-F, 3-OCF₃ phenyl |
| (387) | —C₅H₁₁ | —CF₃ | 2-F, 3-OCF₃ phenyl |

-continued

![structure: R¹-cyclohexyl-cyclohexyl(X⁴)(CF₂O-A²-R²)]

| | R¹ | X⁴ | -A²-R² |
|---|---|---|---|
| (388) | CH=CH₂ | —CF₃ | 2-F, 3-OCF₃ phenyl |
| (389) | —C₃H₇ | —CF₃ | 2,3,5-trifluorophenyl |
| (390) | —C₅H₁₁ | —CF₃ | 2,3,5-trifluorophenyl |
| (391) | CH=CH₂ | —CF₃ | 2,3,5-trifluorophenyl |
| (392) | —C₃H₇ | —CF₃ | 2,3-F, 4-CH₃ phenyl |
| (393) | —C₅H₁₁ | —CF₃ | 2,3-F, 4-CH₃ phenyl |
| (394) | CH=CH₂ | —CF₃ | 2,3-F, 4-CH₃ phenyl |
| (395) | —C₃H₇ | —CF₃ | 2,3-F, 4-CF₃ phenyl |

-continued

-CF₂O-A²-R²)

| | R¹ | X⁴ | -A²-R² |
|---|---|---|---|
| (396) | —C₅H₁₁ | —CF₃ | 2,5-F₂-3-CF₃-phenyl |
| (397) | CH=CH₂ | —CF₃ | 2,5-F₂-3-CF₃-phenyl |
| (398) | —C₃H₇ | —CF₃ | 2,5-F₂-4-OCH₃-phenyl |
| (399) | —C₅H₁₁ | —CF₃ | 2,5-F₂-4-OCH₃-phenyl |
| (400) | CH=CH₂ | —CF₃ | 2,5-F₂-4-OCH₃-phenyl |
| (401) | —C₃H₇ | —CF₃ | 2,5-F₂-4-OCF₃-phenyl |
| (402) | —C₅H₁₁ | —CF₃ | 2,5-F₂-4-OCF₃-phenyl |
| (403) | CH=CH₂ | —CF₃ | 2,5-F₂-4-OCF₃-phenyl |

-continued

-CF₂O-A²-R²)

| | R¹ | X⁴ | -A²-R² |
|---|---|---|---|
| (404) | —C₃H₇ | —CF₃ | 2,3,4-F₃-phenyl |
| (405) | —C₅H₁₁ | —CF₃ | 2,3,4-F₃-phenyl |
| (406) | CH=CH₂ | —CF₃ | 2,3,4-F₃-phenyl |
| (407) | —C₃H₇ | —CF₃ | 2,3-F₂-4-CH₃-phenyl |
| (408) | —C₅H₁₁ | —CF₃ | 2,3-F₂-4-CH₃-phenyl |
| (409) | CH=CH₂ | —CF₃ | 2,3-F₂-4-CH₃-phenyl |
| (410) | —C₃H₇ | —CF₃ | 2,3-F₂-4-CF₃-phenyl |
| (411) | —C₅H₁₁ | —CF₃ | 2,3-F₂-4-CF₃-phenyl |
| (412) | CH=CH₂ | —CF₃ | 2,3-F₂-4-CF₃-phenyl |
| (413) | —C₃H₇ | —CF₃ | 2,3-F₂-4-OCH₃-phenyl |

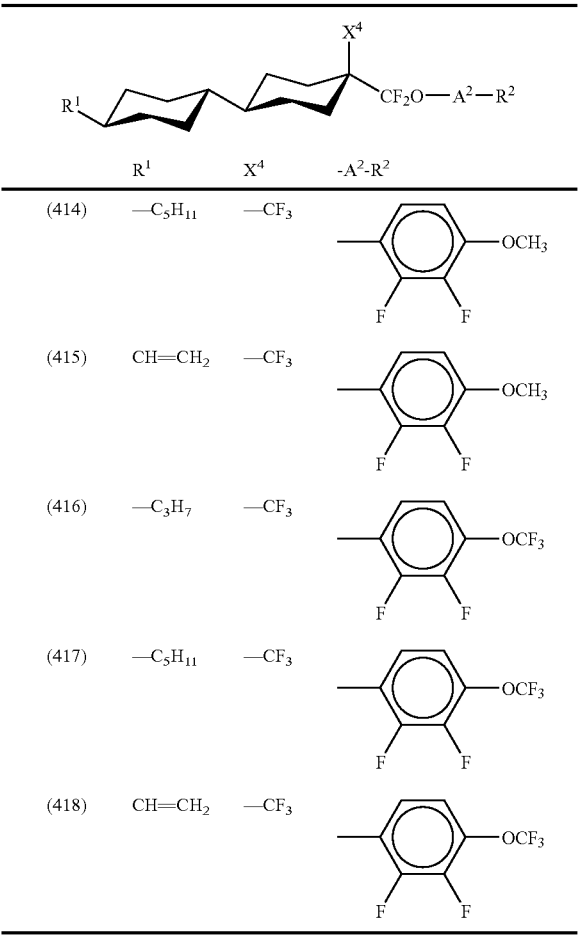
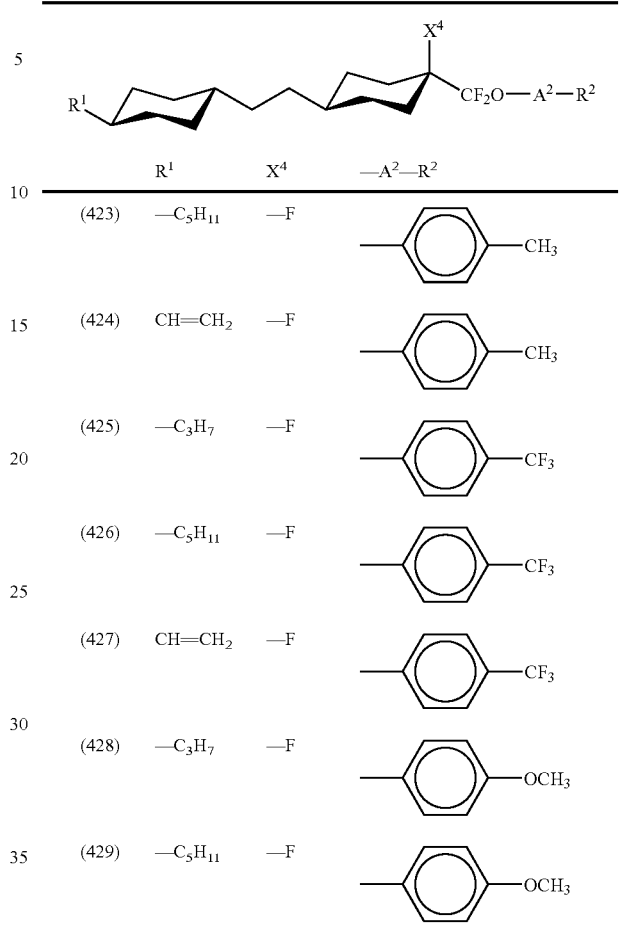
Furthermore, compounds of the formulae shown below are obtained analogously to the previous examples:

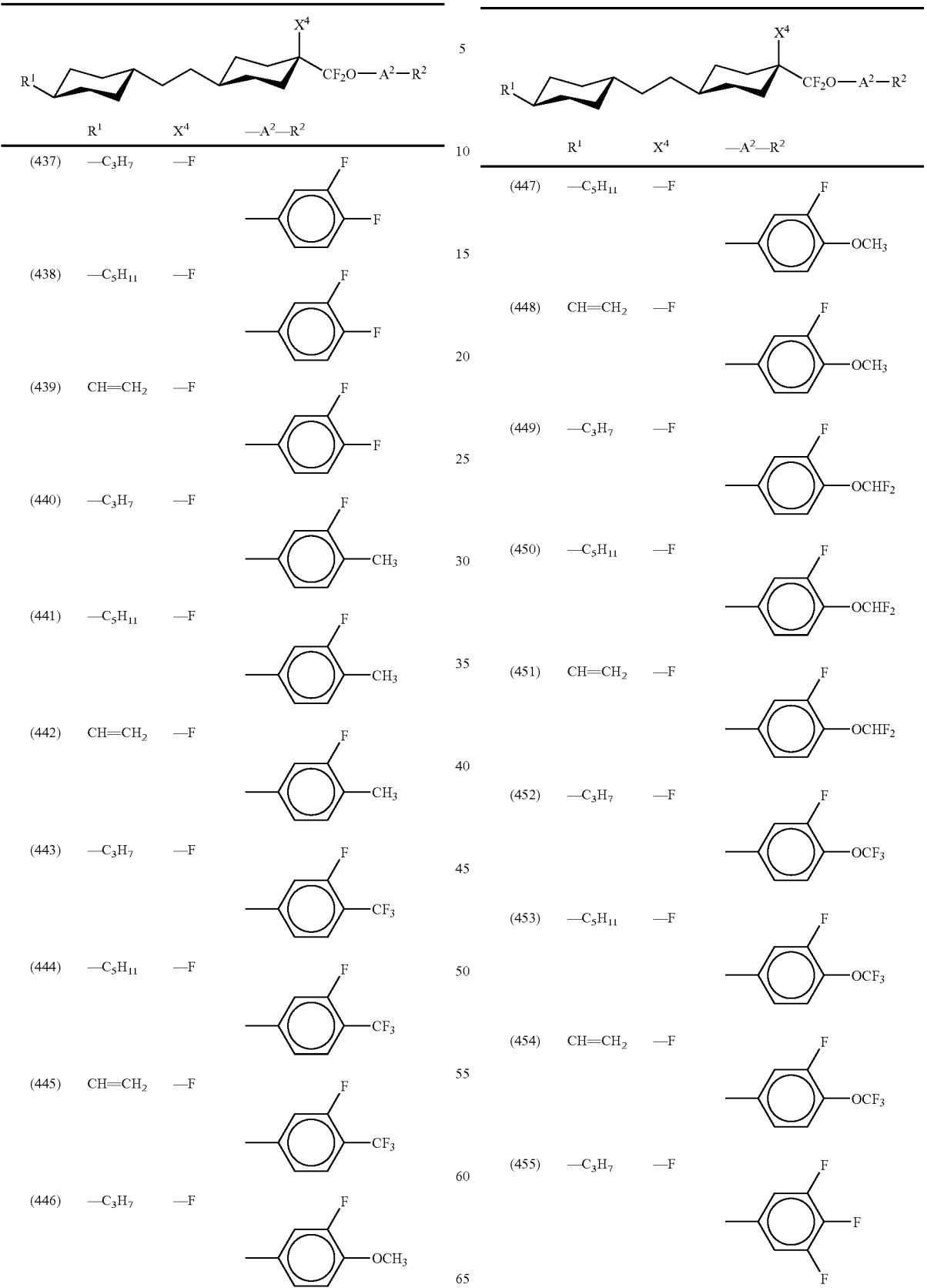

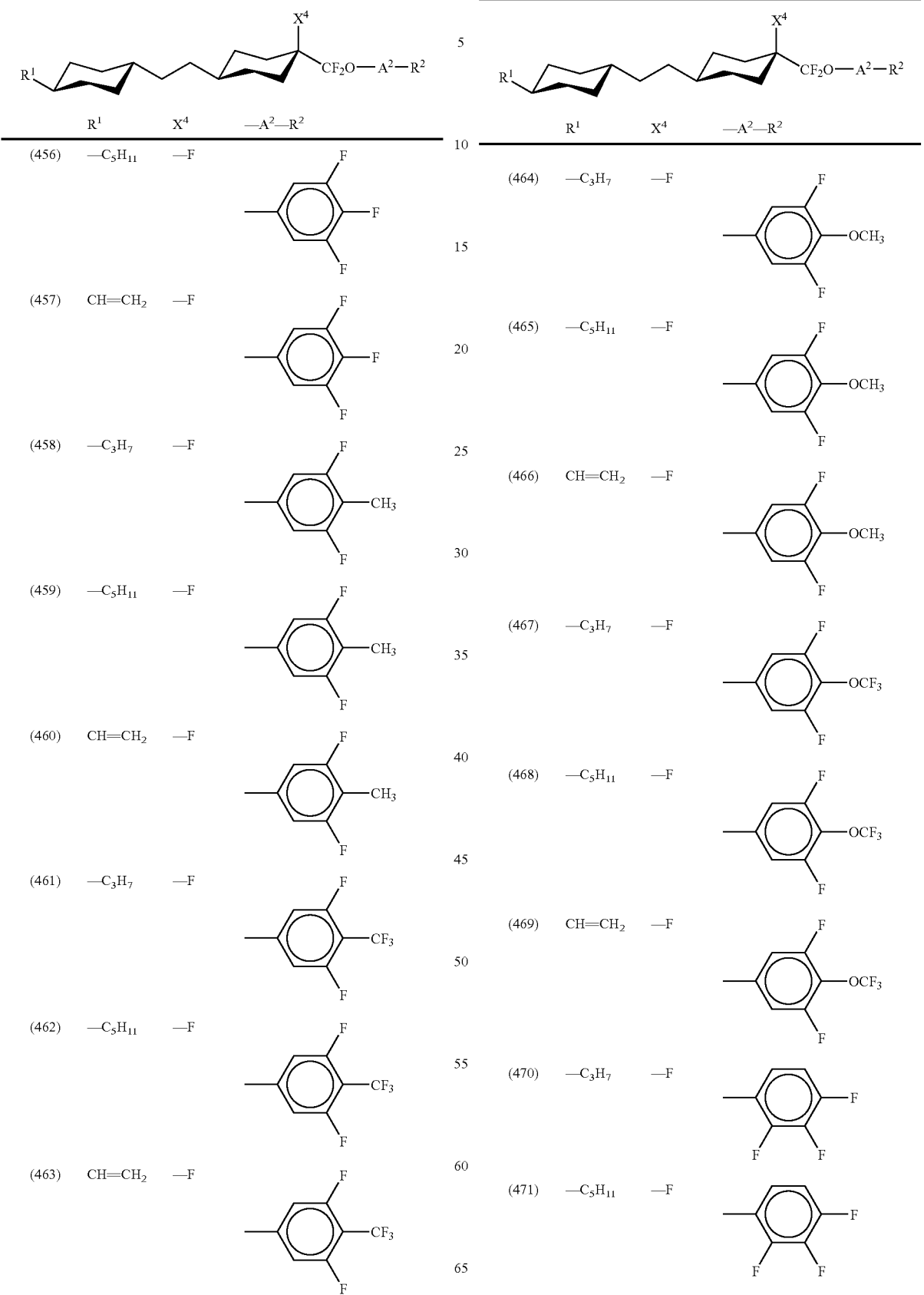

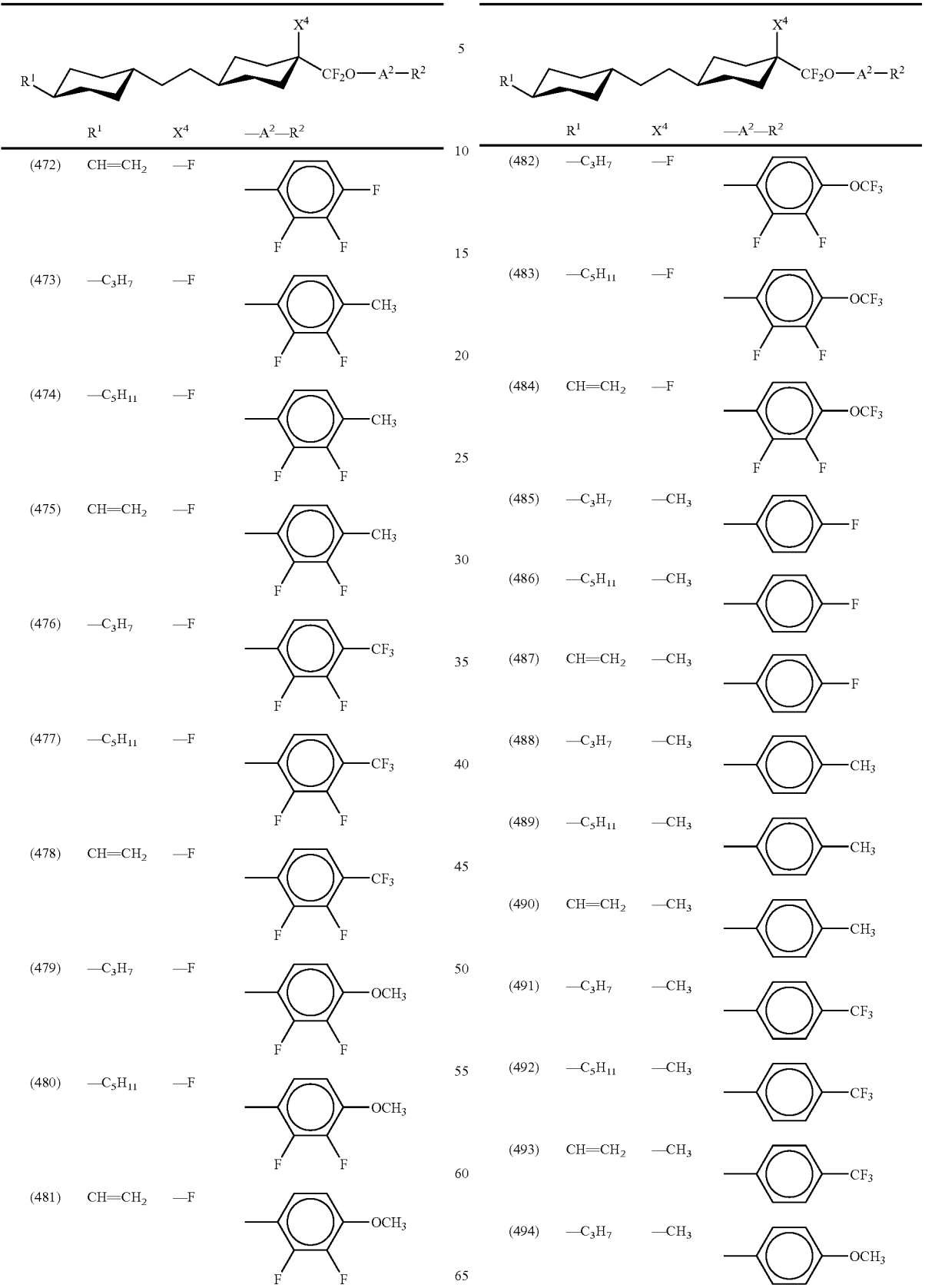

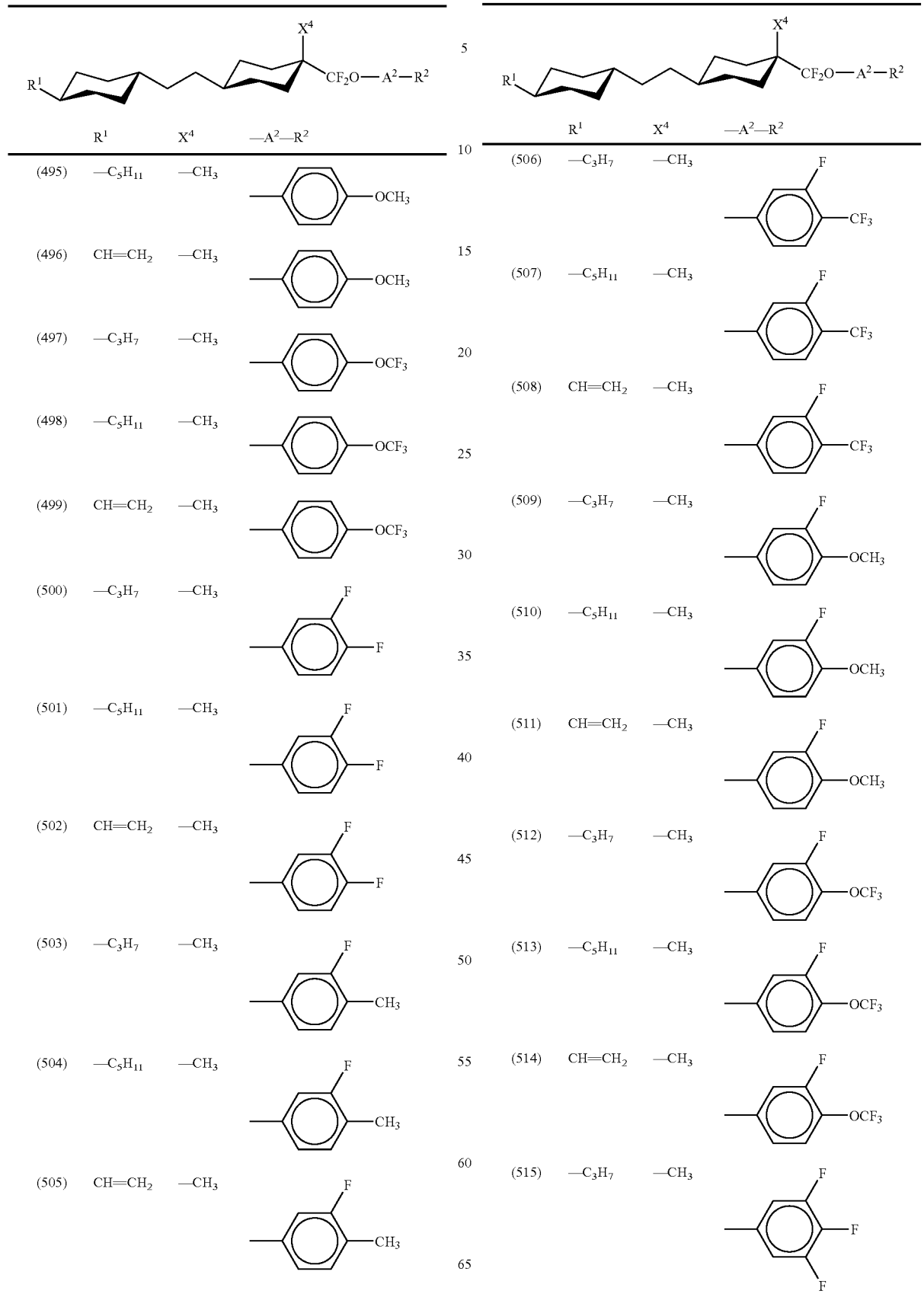

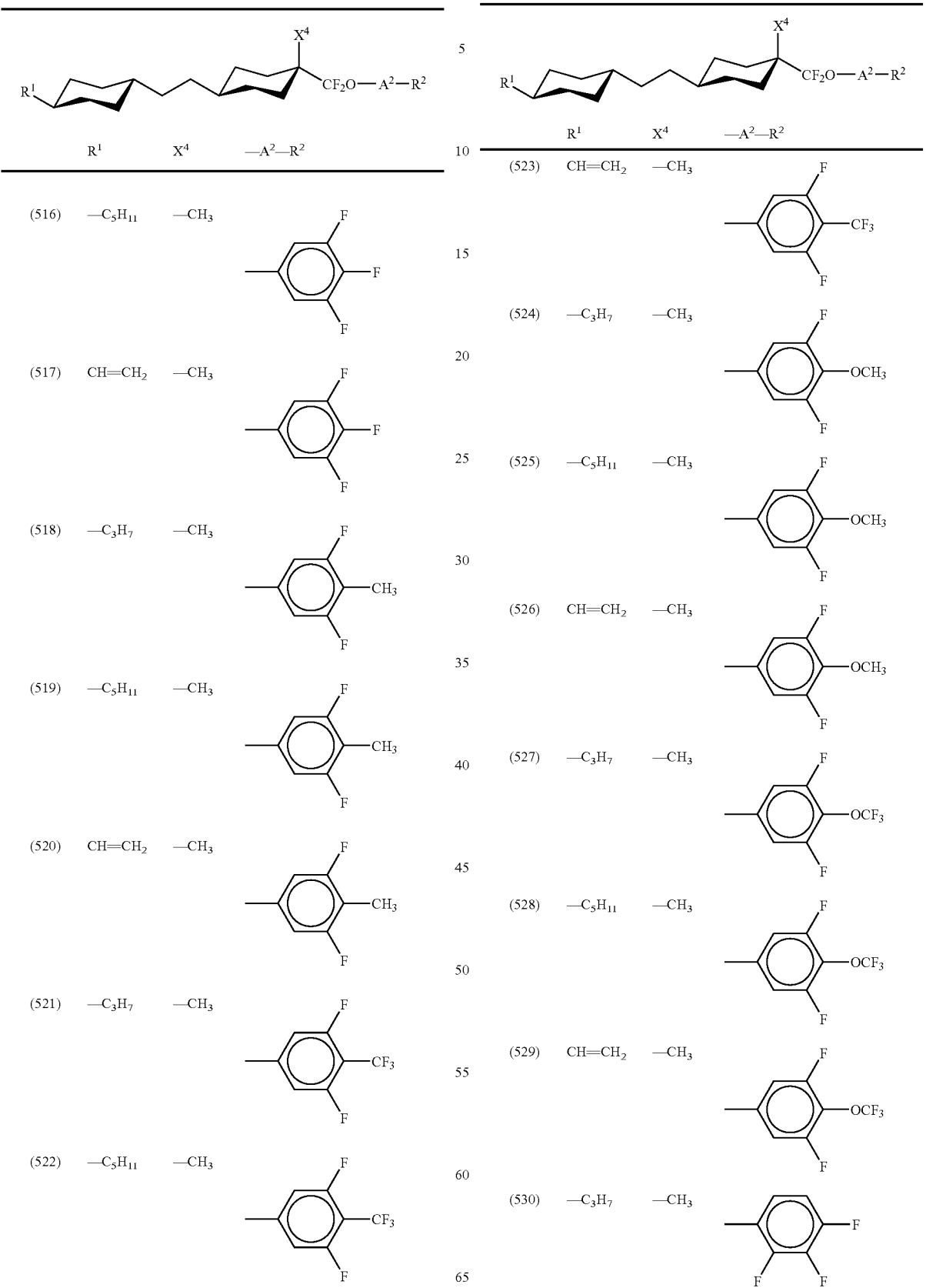

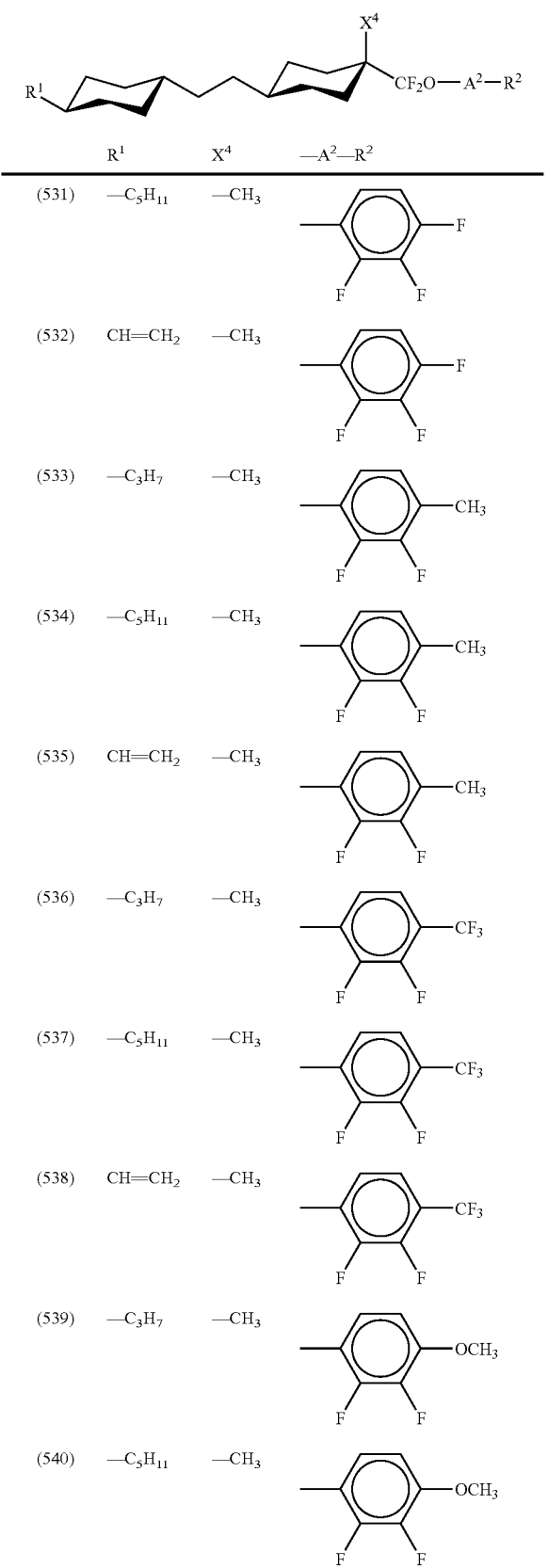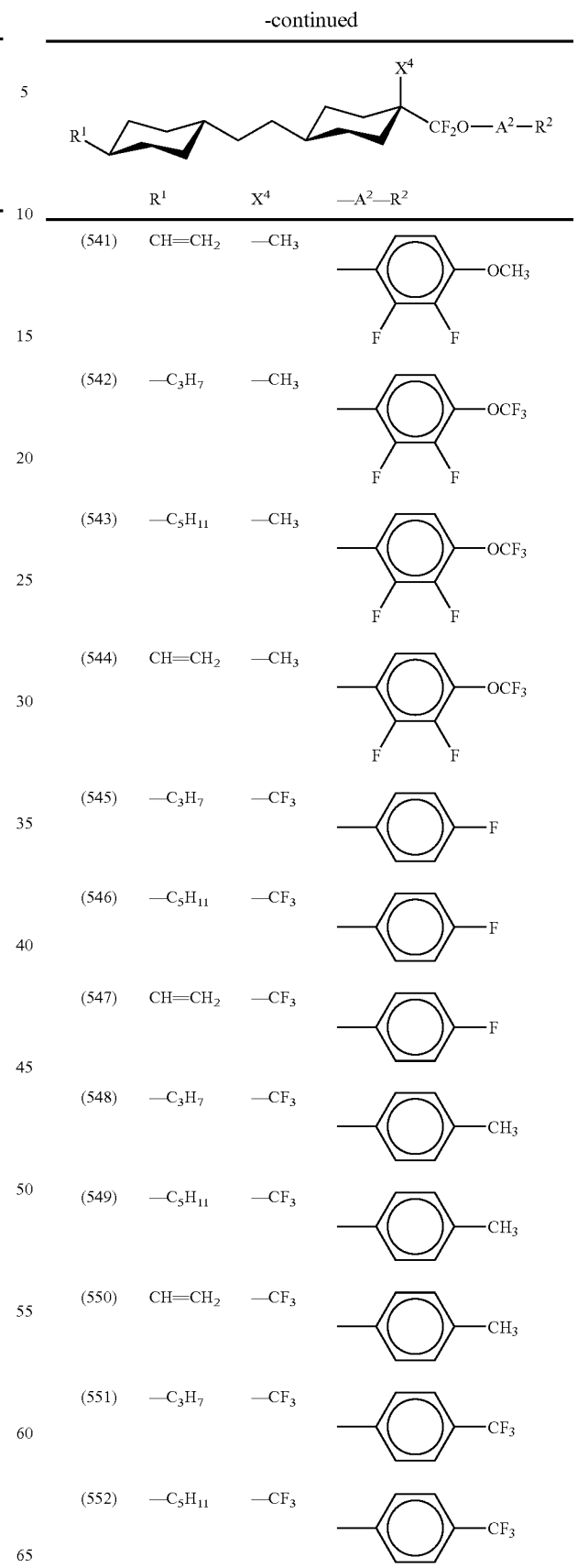

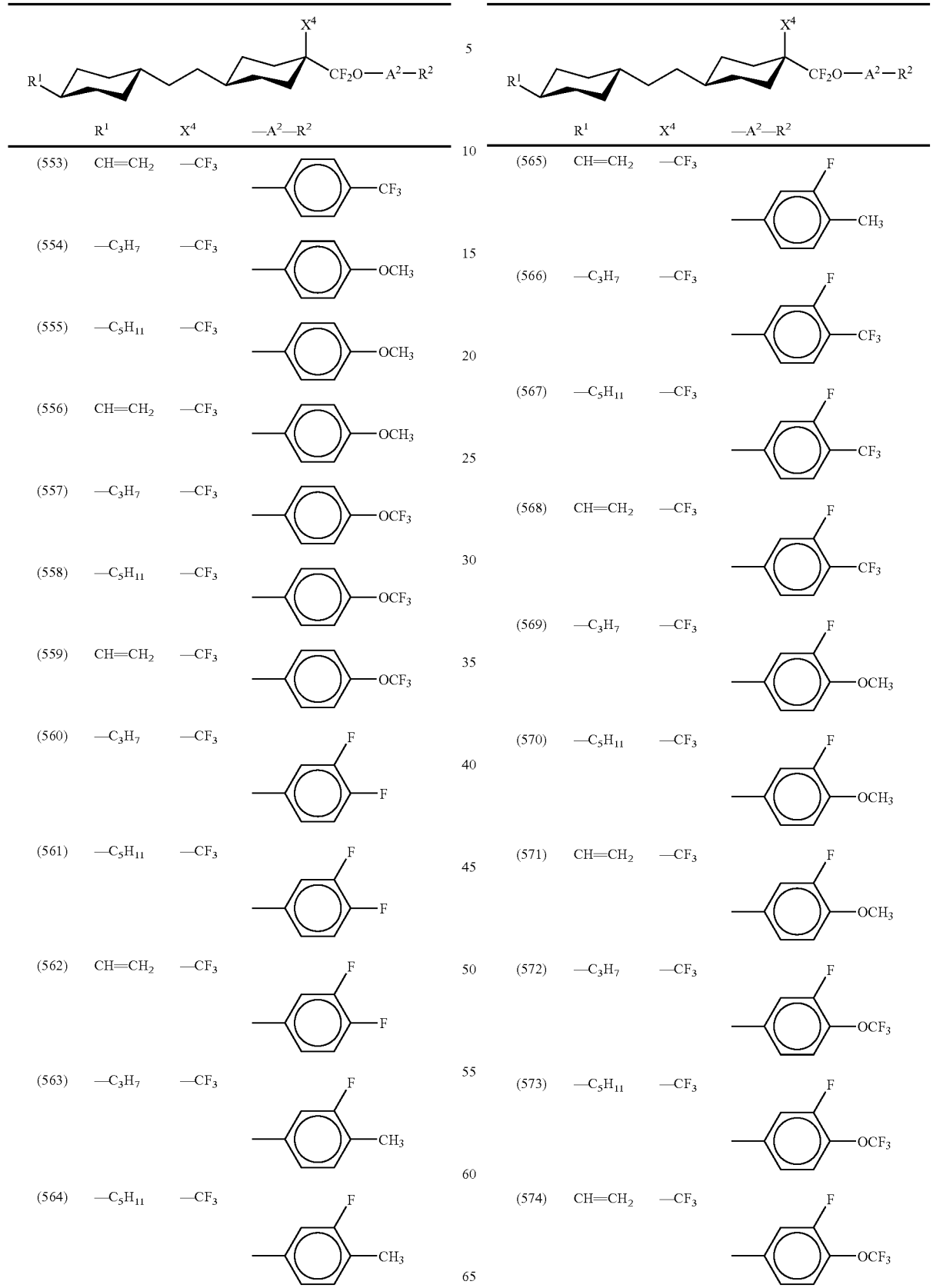

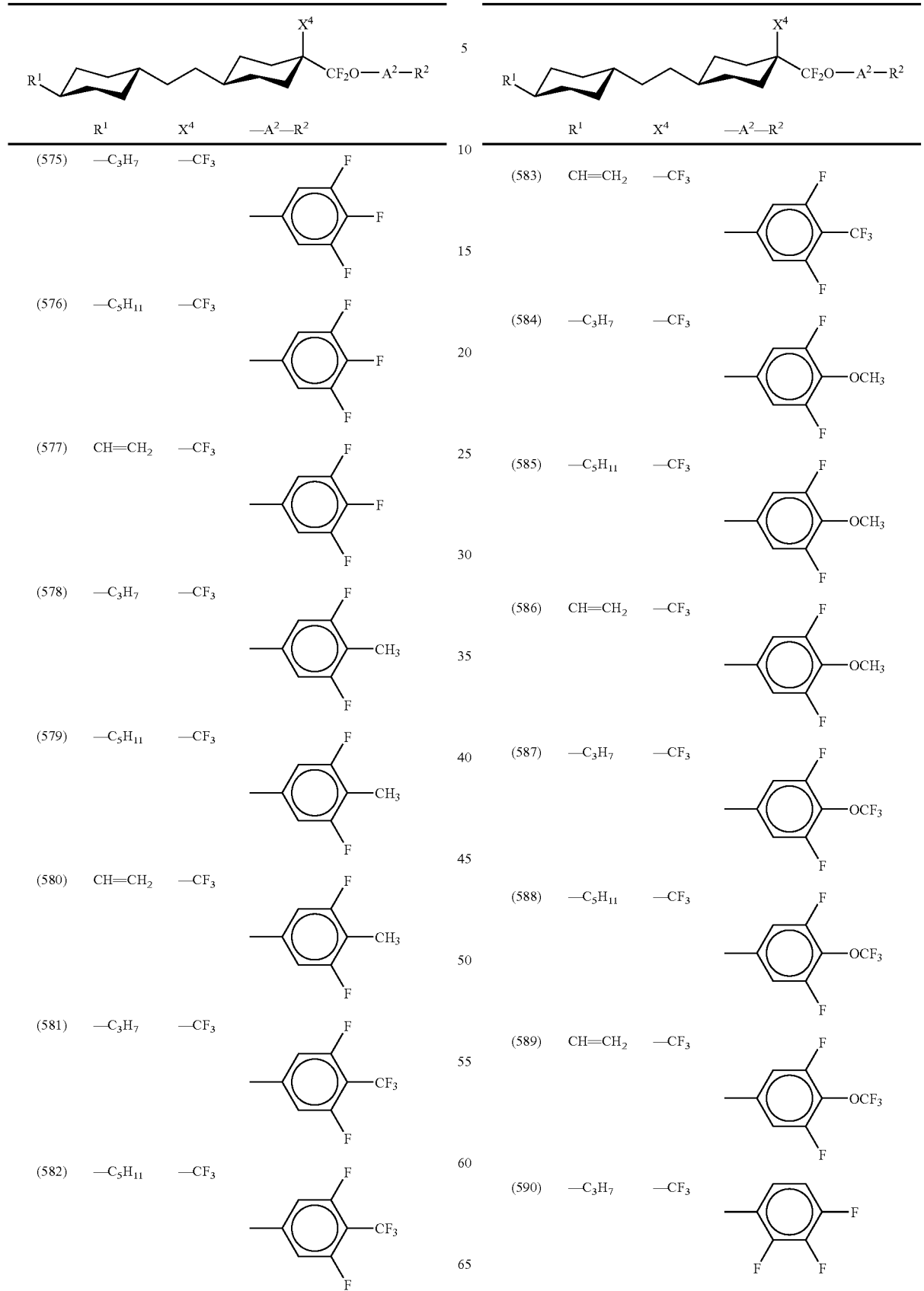

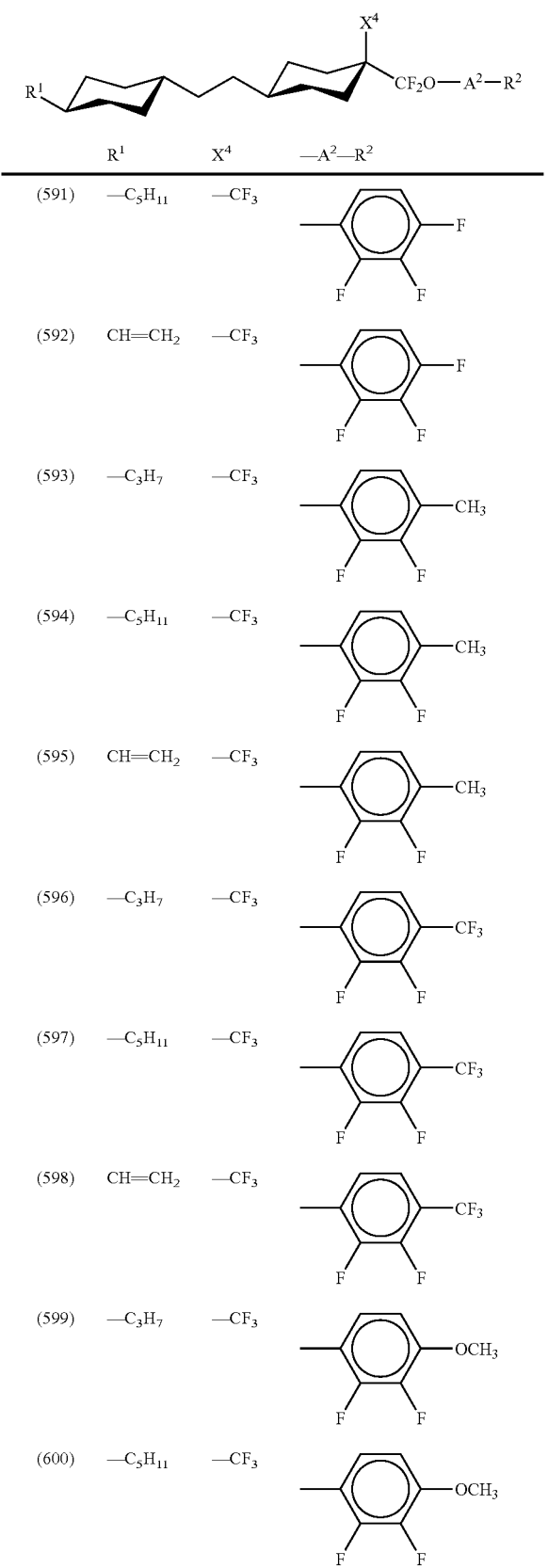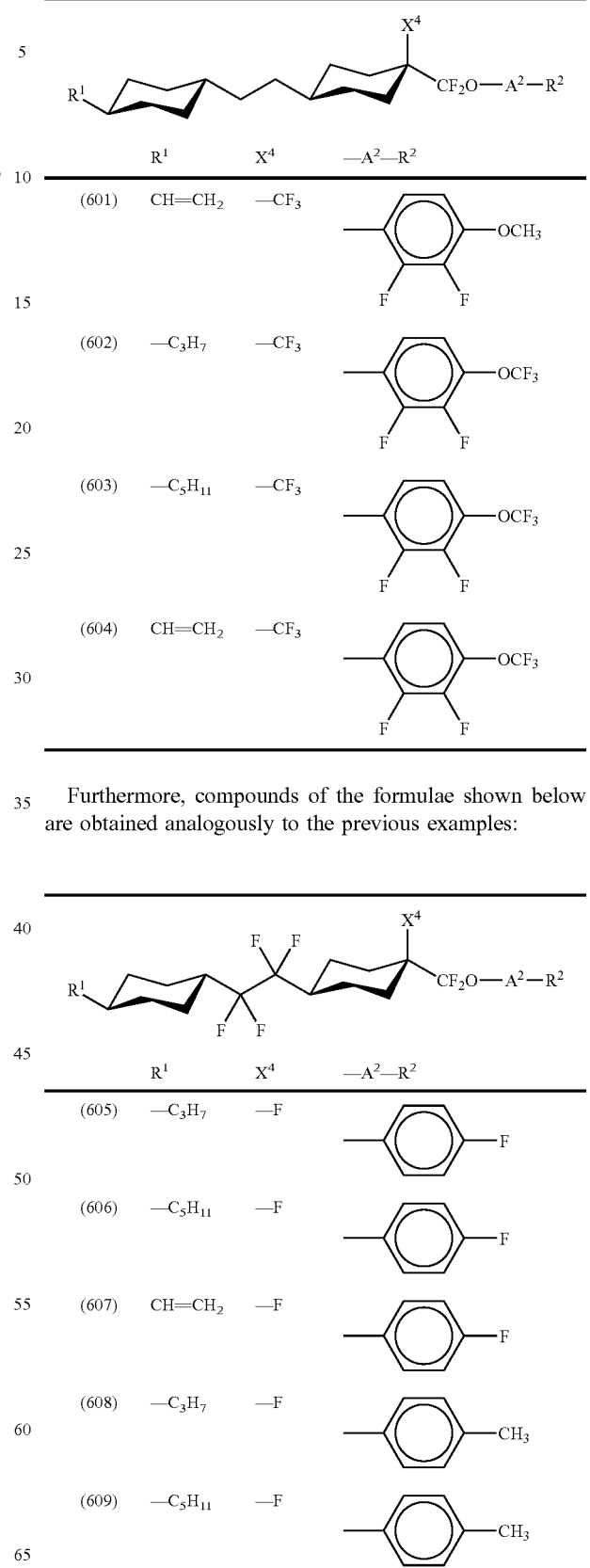
Furthermore, compounds of the formulae shown below are obtained analogously to the previous examples:

-continued
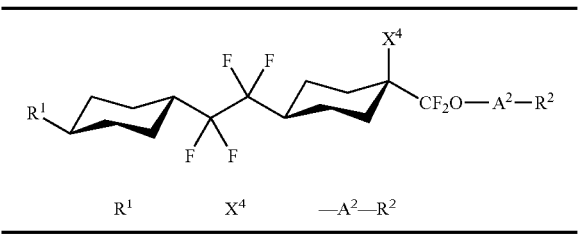
| | R¹ | X⁴ | —A²—R² |
|---|---|---|---|
| (610) | CH=CH₂ | —F |  |
| (611) | —C₃H₇ | —F | 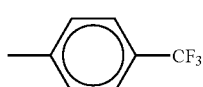 |
| (612) | —C₅H₁₁ | —F |  |
| (613) | CH=CH₂ | —F | 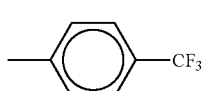 |
| (614) | —C₃H₇ | —F | 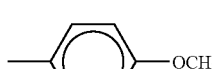 |
| (615) | —C₅H₁₁ | —F | 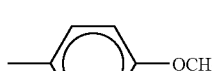 |
| (616) | CH=CH₂ | —F | 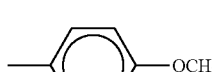 |
| (617) | —C₃H₇ | —F | 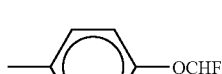 |
| (618) | —C₅H₁₁ | —F |  |
| (619) | CH=CH₂ | —F |  |
| (620) | —C₃H₇ | —F |  |
| (621) | —C₅H₁₁ | —F |  |
| (622) | CH=CH₂ | —F |  |
-continued
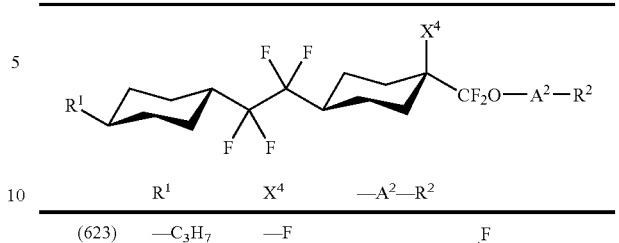
| | R¹ | X⁴ | —A²—R² |
|---|---|---|---|
| (623) | —C₃H₇ | —F | 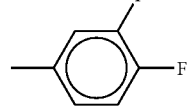 |
| (624) | —C₅H₁₁ | —F | 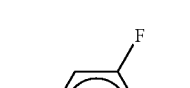 |
| (625) | CH=CH₂ | —F | 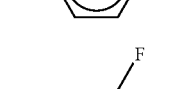 |
| (626) | —C₃H₇ | —F | 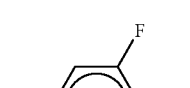 |
| (627) | —C₅H₁₁ | —F | 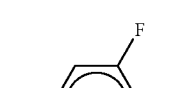 |
| (628) | CH=CH₂ | —F | 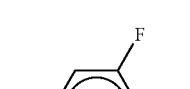 |
| (629) | —C₃H₇ | —F | 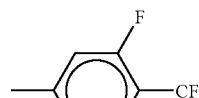 |
| (630) | —C₅H₁₁ | —F | 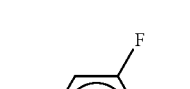 |
| (631) | CH=CH₂ | —F | 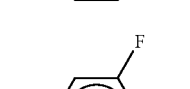 |
| (632) | —C₃H₇ | —F | 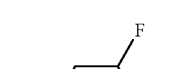 |

-continued
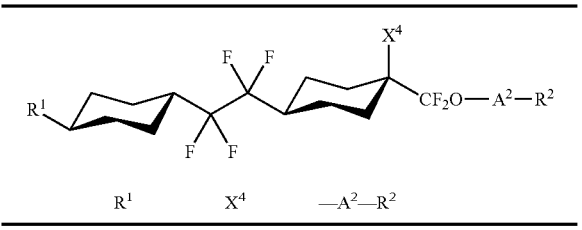
| | R¹ | X⁴ | —A²—R² |
|---|---|---|---|
| (633) | —C₅H₁₁ | —F | 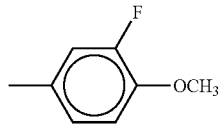 |
| (634) | CH=CH₂ | —F | 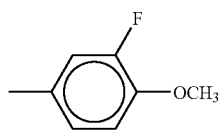 |
| (635) | —C₃H₇ | —F | 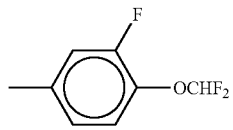 |
| (636) | —C₅H₁₁ | —F | 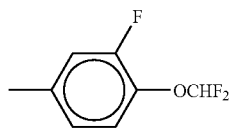 |
| (637) | CH=CH₂ | —F | 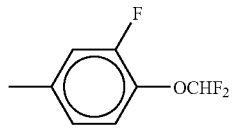 |
| (638) | —C₃H₇ | —F | 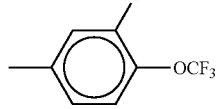 |
| (639) | —C₅H₁₁ | —F | 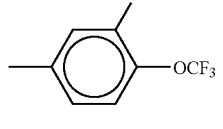 |
| (640) | CH=CH₂ | —F | 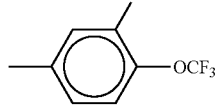 |
| (641) | —C₃H₇ | —F | 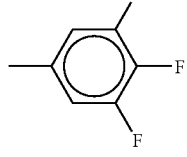 |
-continued
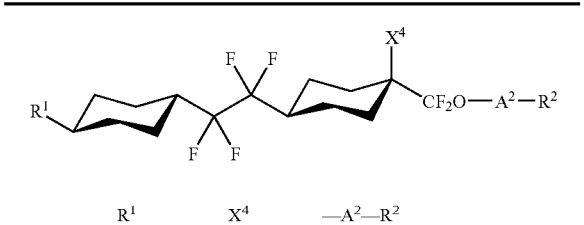
| | R¹ | X⁴ | —A²—R² |
|---|---|---|---|
| (642) | —C₅H₁₁ | —F | 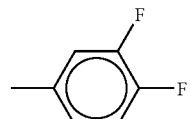 |
| (643) | CH=CH₂ | —F | 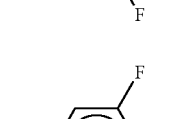 |
| (644) | —C₃H₇ | —F | 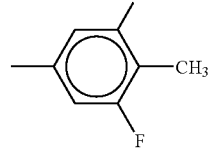 |
| (645) | —C₅H₁₁ | —F | 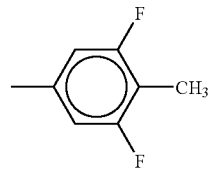 |
| (646) | CH=CH₂ | —F | 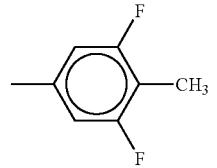 |
| (647) | —C₃H₇ | —F | 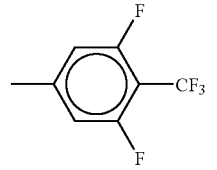 |
| (648) | —C₅H₁₁ | —F | 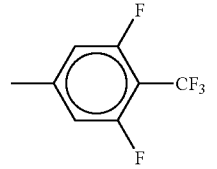 |

-continued
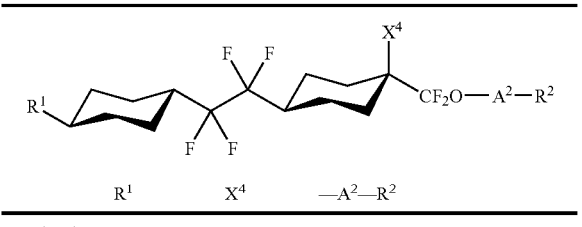
| | R¹ | X⁴ | —A²—R² |
|---|---|---|---|
| (649) | CH=CH₂ | —F | 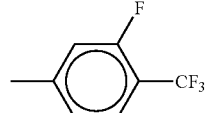 |
| (650) | —C₃H₇ | —F | 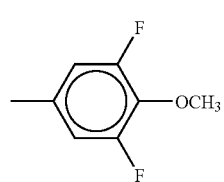 |
| (651) | —C₅H₁₁ | —F | 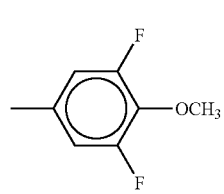 |
| (652) | CH=CH₂ | —F | 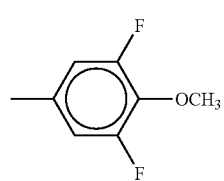 |
| (653) | —C₃H₇ | —F | 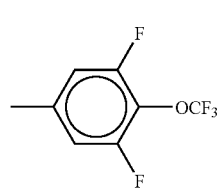 |
| (654) | —C₅H₁₁ | —F | 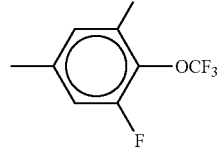 |
| (655) | CH=CH₂ | —F | 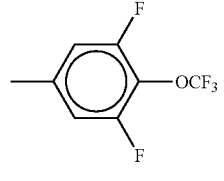 |
| (656) | —C₃H₇ | —F | 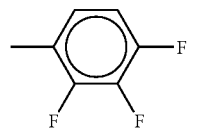 |
-continued
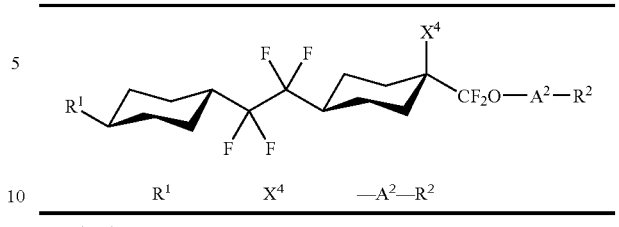
| | R¹ | X⁴ | —A²—R² |
|---|---|---|---|
| (657) | —C₅H₁₁ | —F | 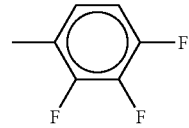 |
| (658) | CH=CH₂ | —F | 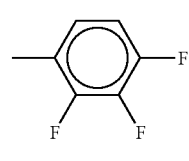 |
| (659) | —C₃H₇ | —F | 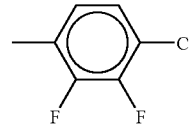 |
| (660) | —C₅H₁₁ | —F | 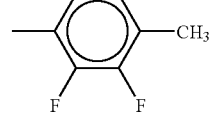 |
| (661) | CH=CH₂ | —F | 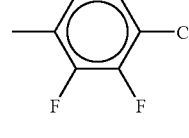 |
| (662) | —C₃H₇ | —F | 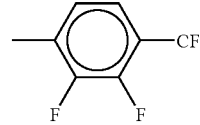 |
| (663) | —C₅H₁₁ | —F | 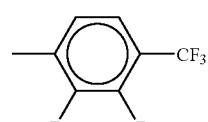 |
| (664) | CH=CH₂ | —F | 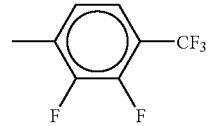 |
| (665) | —C₃H₇ | —F | 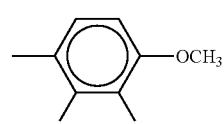 |
| (666) | —C₅H₁₁ | —F | 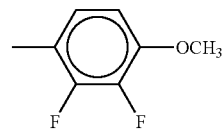 |

-continued

![structure: R1-cyclohexyl-CF2-CF2-cyclohexyl(X4)-CF2O-A2-R2]

| | R¹ | X⁴ | —A²—R² |
|---|---|---|---|
| (667) | CH=CH₂ | —F | phenyl-OCH₃ with 2,3-diF |
| (668) | —C₃H₇ | —F | phenyl-OCF₃ with 2,3-diF |
| (669) | —C₅H₁₁ | —F | phenyl-OCF₃ with 2,3-diF |
| (670) | CH=CH₂ | —F | phenyl-OCF₃ with 2,3-diF |
| (671) | —C₃H₇ | —CH₃ | phenyl-F |
| (672) | —C₅H₁₁ | —CH₃ | phenyl-F |
| (673) | CH=CH₂ | —CH₃ | phenyl-F |
| (674) | —C₃H₇ | —CH₃ | phenyl-CH₃ |
| (675) | —C₅H₁₁ | —CH₃ | phenyl-CH₃ |
| (676) | CH=CH₂ | —CH₃ | phenyl-CH₃ |
| (677) | —C₃H₇ | —CH₃ | phenyl-CF₃ |
| (678) | —C₅H₁₁ | —CH₃ | phenyl-CF₃ |
| (679) | CH=CH₂ | —CH₃ | phenyl-CF₃ |
| (680) | —C₃H₇ | —CH₃ | phenyl-OCH₃ |
| (681) | —C₅H₁₁ | —CH₃ | phenyl-OCH₃ |
| (682) | CH=CH₂ | —CH₃ | phenyl-OCH₃ |
| (683) | —C₃H₇ | —CH₃ | phenyl-OCF₃ |
| (684) | —C₅H₁₁ | —CH₃ | phenyl-OCF₃ |
| (685) | CH=CH₂ | —CH₃ | phenyl-OCF₃ |
| (686) | —C₃H₇ | —CH₃ | phenyl-3,4-diF |
| (687) | —C₅H₁₁ | —CH₃ | phenyl-3,4-diF |
| (688) | CH=CH₂ | —CH₃ | phenyl-3,4-diF |
| (689) | —C₃H₇ | —CH₃ | phenyl-3-F-4-CH₃ |
| (690) | —C₅H₁₁ | —CH₃ | phenyl-3-F-4-CH₃ |

-continued
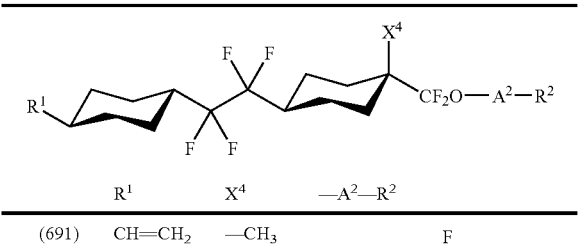
| | R¹ | X⁴ | —A²—R² |
|---|---|---|---|
| (691) | CH=CH₂ | —CH₃ | 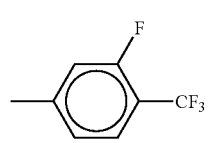 |
| (692) | —C₃H₇ | —CH₃ | 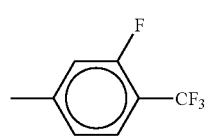 |
| (693) | —C₅H₁₁ | —CH₃ | 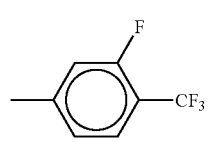 |
| (694) | CH=CH₂ | —CH₃ | 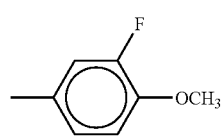 |
| (695) | —C₃H₇ | —CH₃ | 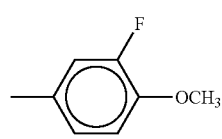 |
| (696) | —C₅H₁₁ | —CH₃ | 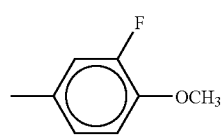 |
| (697) | CH=CH₂ | —CH₃ | 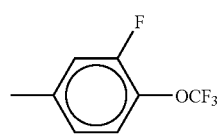 |
| (698) | —C₃H₇ | —CH₃ | 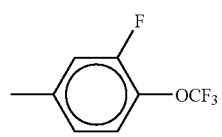 |
| (699) | —C₅H₁₁ | —CH₃ | 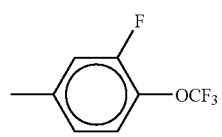 |
| (700) | CH=CH₂ | —CH₃ | 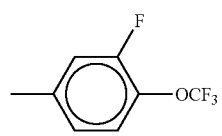 |
-continued
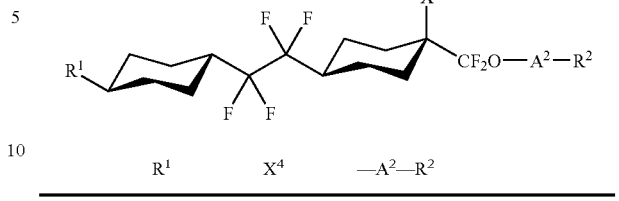
| | R¹ | X⁴ | —A²—R² |
|---|---|---|---|
| (701) | —C₃H₇ | —CH₃ | 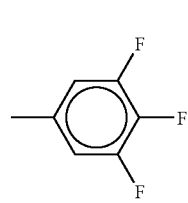 |
| (702) | —C₅H₁₁ | —CH₃ | 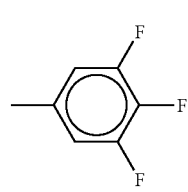 |
| (703) | CH=CH₂ | —CH₃ | 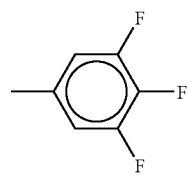 |
| (704) | —C₃H₇ | —CH₃ | 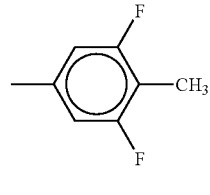 |
| (705) | —C₅H₁₁ | —CH₃ | 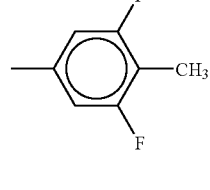 |
| (706) | CH=CH₂ | —CH₃ | 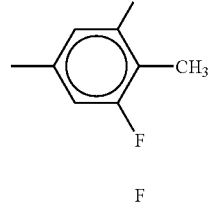 |
| (707) | —C₃H₇ | —CH₃ | 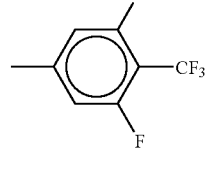 |

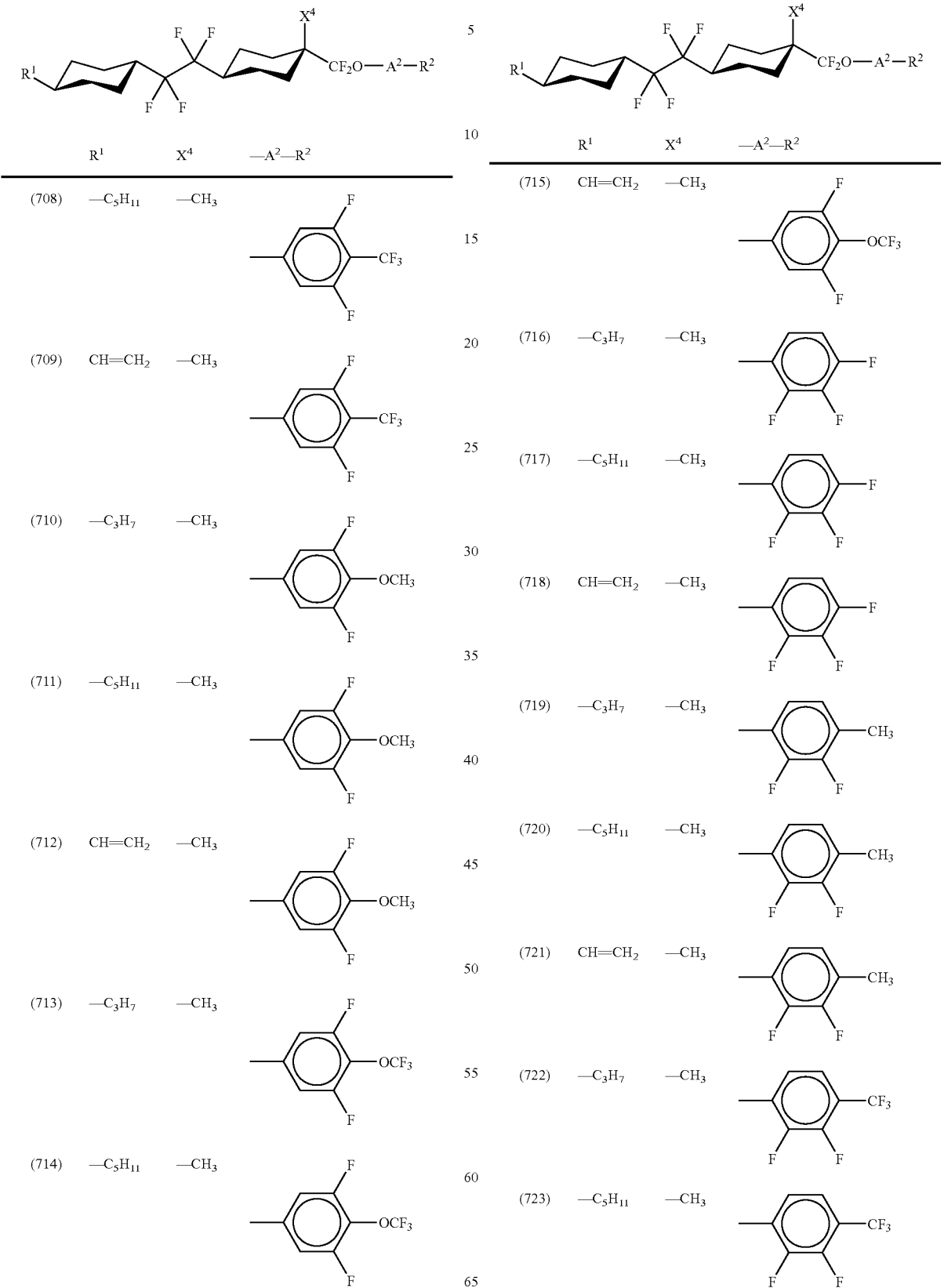

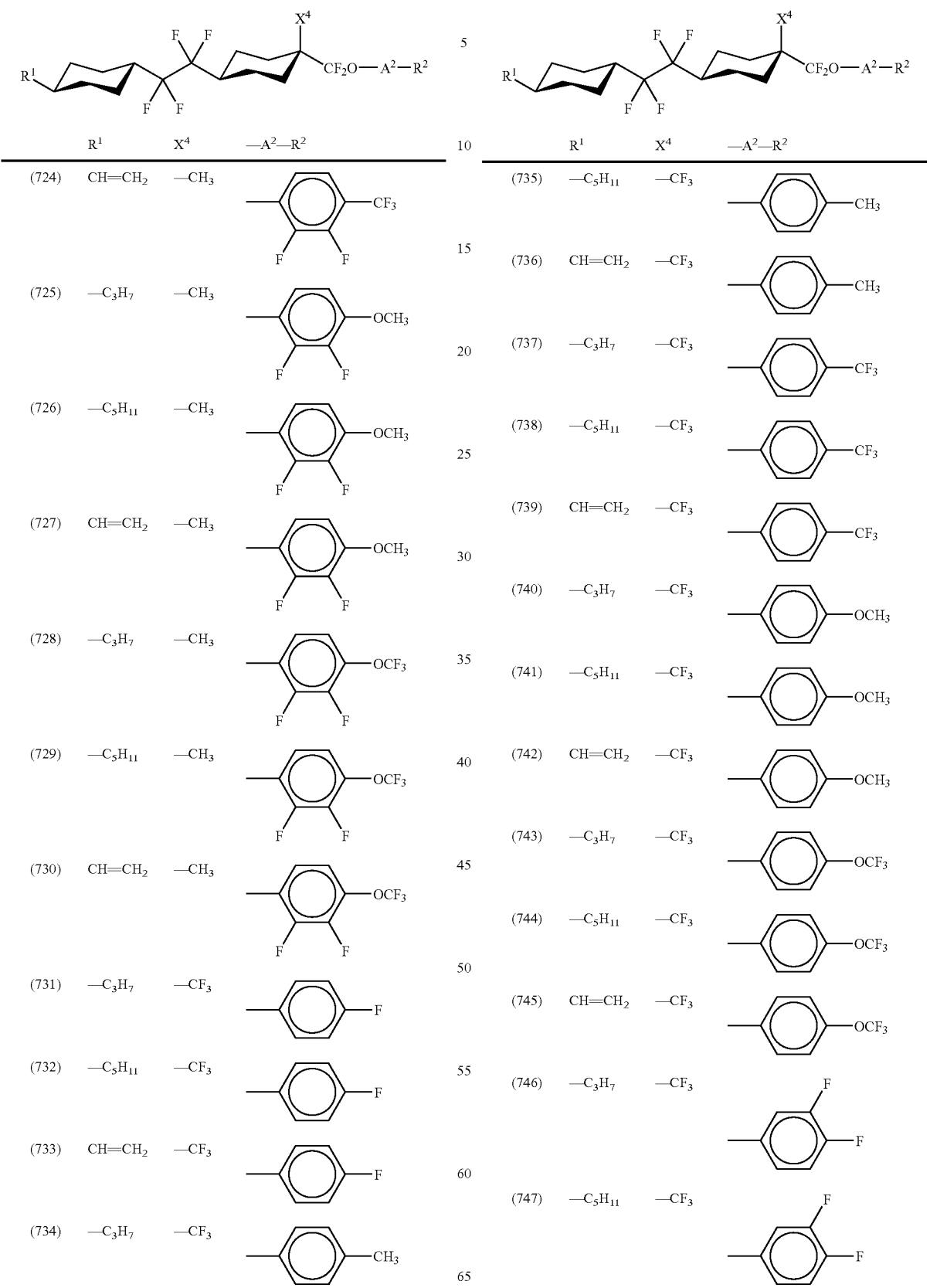

-continued
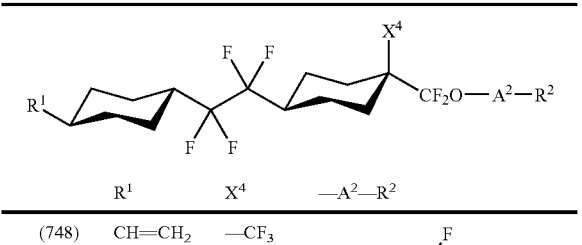
| | R¹ | X⁴ | —A²—R² |
|---|---|---|---|
| (748) | CH=CH₂ | —CF₃ |  |
| (749) | —C₃H₇ | —CF₃ | 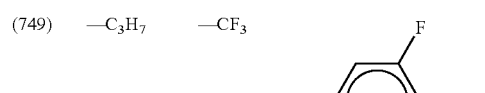 |
| (750) | —C₅H₁₁ | —CF₃ | 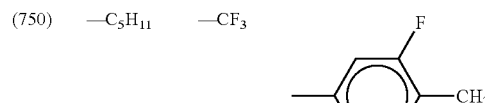 |
| (751) | CH=CH₂ | —CF₃ | 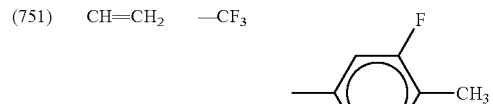 |
| (752) | —C₃H₇ | —CF₃ | 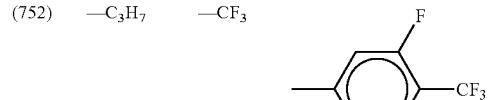 |
| (753) | —C₅H₁₁ | —CF₃ | 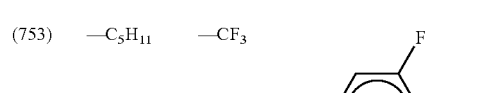 |
| (754) | CH=CH₂ | —CF₃ | 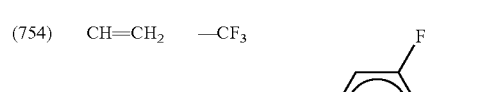 |
| (755) | —C₃H₇ | —CF₃ | 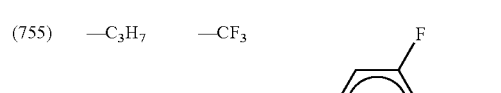 |
| (756) | —C₅H₁₁ | —CF₃ | 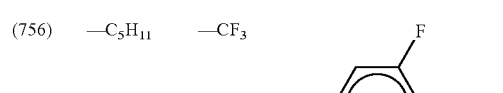 |
| (757) | CH=CH₂ | —CF₃ | 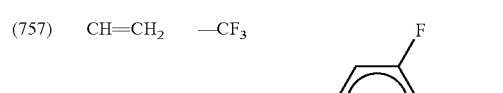 |
-continued
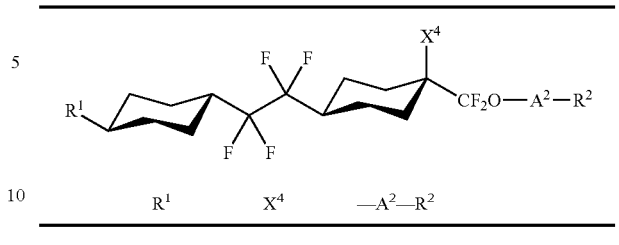
| | R¹ | X⁴ | —A²—R² |
|---|---|---|---|
| (758) | —C₃H₇ | —CF₃ | 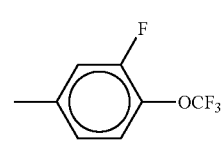 |
| (759) | —C₅H₁₁ | —CF₃ | 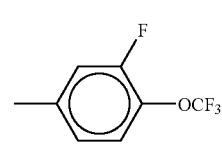 |
| (760) | CH=CH₂ | —CF₃ | 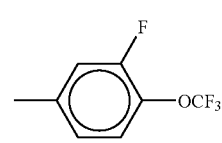 |
| (761) | —C₃H₇ | —CF₃ | 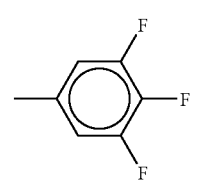 |
| (762) | —C₅H₁₁ | —CF₃ | 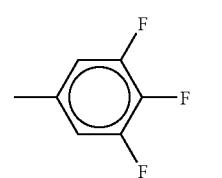 |
| (763) | CH=CH₂ | —CF₃ | 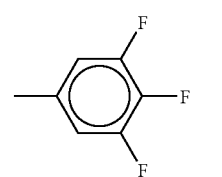 |
| (764) | —C₃H₇ | —CF₃ | 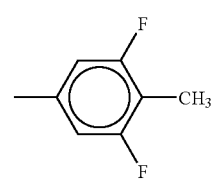 |
| (765) | —C₅H₁₁ | —CF₃ | 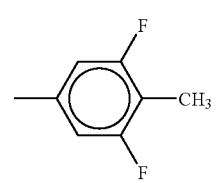 |

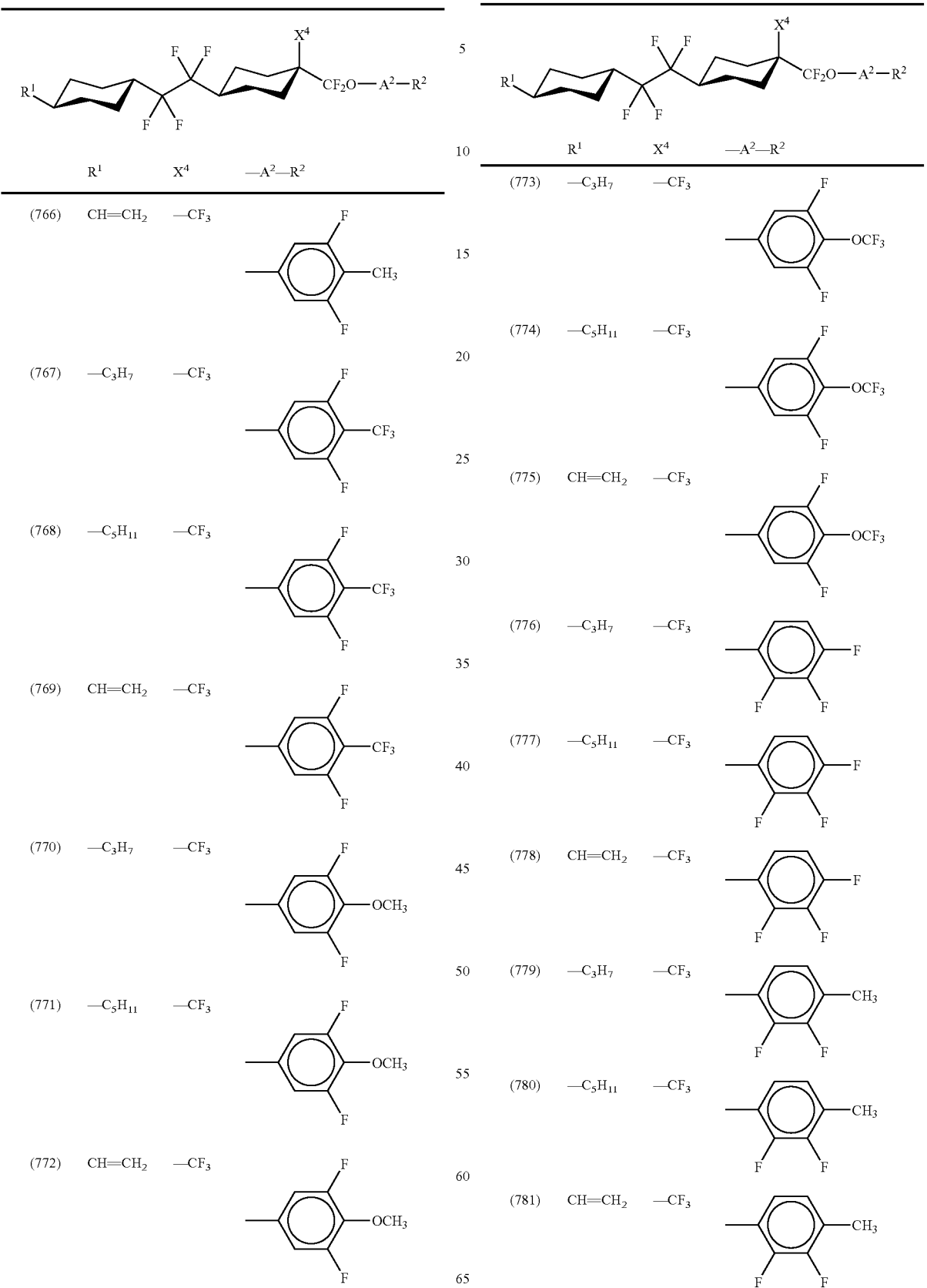

-continued
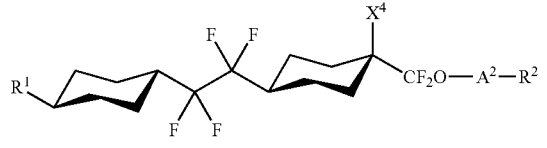
| | R¹ | X⁴ | —A²—R² |
|---|---|---|---|
| (782) | —C₃H₇ | —CF₃ | 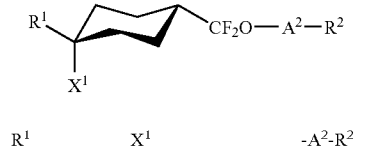 |
| (783) | —C₅H₁₁ | —CF₃ | 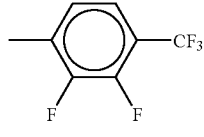 |
| (784) | CH=CH₂ | —CF₃ |  |
| (785) | —C₃H₇ | —CF₃ | 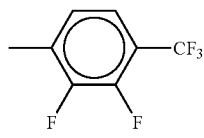 |
| (786) | —C₅H₁₁ | —CF₃ |  |
| (787) | CH=CH₂ | —CF₃ | 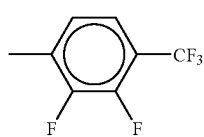 |
| (788) | —C₃H₇ | —CF₃ | 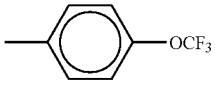 |
| (789) | —C₅H₁₁ | —CF₃ | 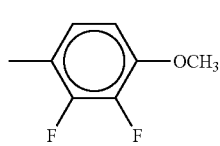 |
| (790) | CH=CH₂ | —CF₃ | 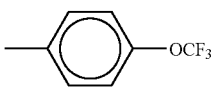 |
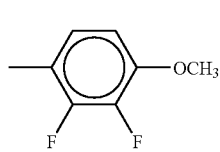
| | R¹ | X¹ | -A²-R² |
|---|---|---|---|
| (791) | —C₃H₇ | —F | 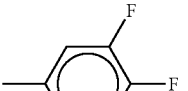 |
| (792) | C₅H₁₁ | —F | 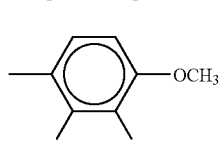 |
| (793) | —C₃H₇ | —F | 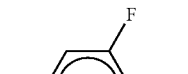 |
| (794) | C₅H₁₁ | —F | 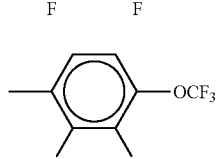 |
| (795) | —C₃H₇ | —F | 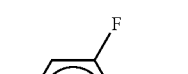 |
| (796) | C₅H₁₁ | —F | 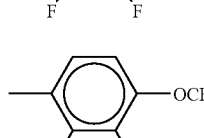 |
| (797) | —C₃H₇ | —F | 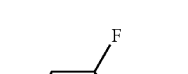 |
| (798) | C₅H₁₁ | —F | 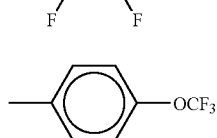 |
| (799) | —C₃H₇ | —F | 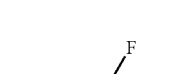 |
| (800) | C₅H₁₁ | —F | 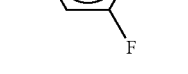 |
Furthermore, compounds of the formulae shown below are obtained analogously to the previous examples:

-continued
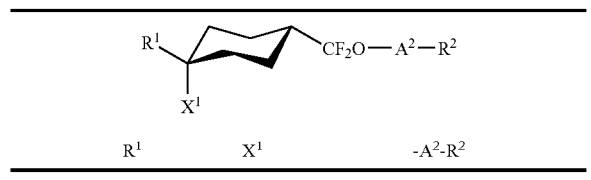
| | R¹ | X¹ | -A²-R² |
|---|---|---|---|
| (801) | —C₃H₇ | —F | 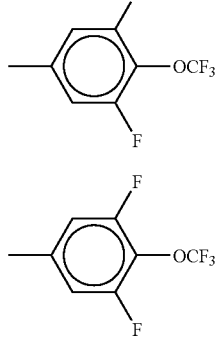 |
| (802) | C₅H₁₁ | —F | |
| (803) | —C₃H₇ | —F | 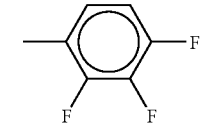 |
| (804) | C₅H₁₁ | —F | 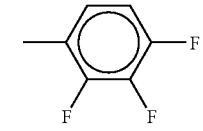 |
| (805) | —C₃H₇ | —F | 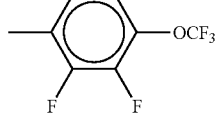 |
| (806) | C₅H₁₁ | —F | 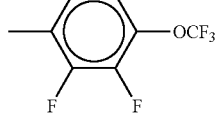 |
| (807) | —C₃H₇ | —CH₃ |  |
| (808) | C₅H₁₁ | —CH₃ |  |
| (809) | —C₃H₇ | —CH₃ |  |
| (810) | C₅H₁₁ | —CH₃ | 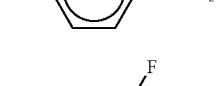 |
| (811) | —C₃H₇ | —CH₃ | 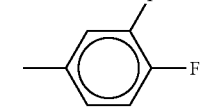 |
-continued
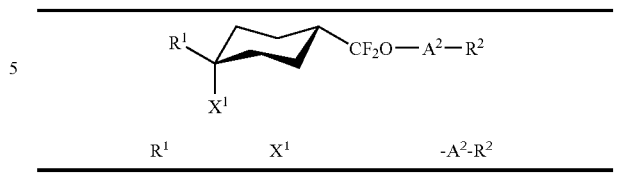
| | R¹ | X¹ | -A²-R² |
|---|---|---|---|
| (812) | C₅H₁₁ | —CH₃ | 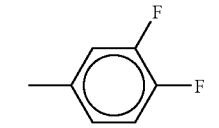 |
| (813) | —C₃H₇ | —CH₃ | 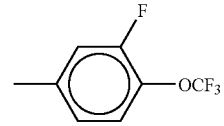 |
| (814) | C₅H₁₁ | —CH₃ | 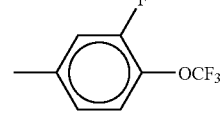 |
| (815) | —C₃H₇ | —CH₃ | 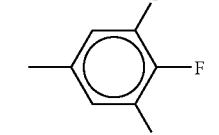 |
| (816) | C₅H₁₁ | —CH₃ | 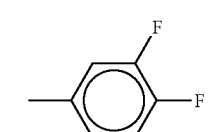 |
| (817) | —C₃H₇ | —CH₃ | 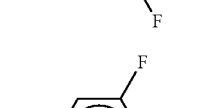 |
| (818) | C₅H₁₁ | —CH₃ | 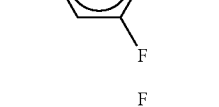 |
| (819) | —C₃H₇ | —CH₃ | 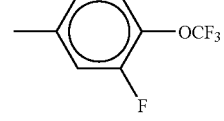 |
| (820) | C₅H₁₁ | —CH₃ | 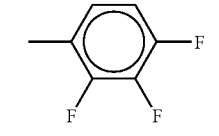 |

-continued
| | R¹ | X¹ | -A²-R² |
|---|---|---|---|
| (821) | —C₃H₇ | —CH₃ |  |
| (822) | C₅H₁₁ | —CH₃ | 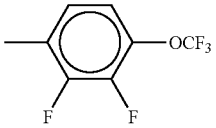 |
| (823) | —C₃H₇ | —CF₃ | 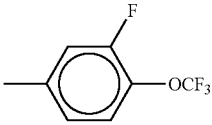 |
| (824) | C₅H₁₁ | —CF₃ | 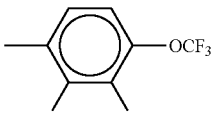 |
| (825) | —C₃H₇ | —CF₃ | 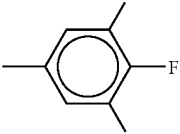 |
| (826) | C₅H₁₁ | —CF₃ |  |
| (827) | —C₃H₇ | —CF₃ | 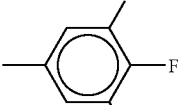 |
| (828) | C₅H₁₁ | —CF₃ |  |
| (829) | —C₃H₇ | —CF₃ | 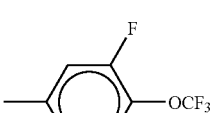 |
-continued
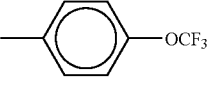
| | R¹ | X¹ | -A²-R² |
|---|---|---|---|
| (830) | C₅H₁₁ | —CF₃ | 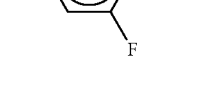 |
| (831) | —C₃H₇ | —CF₃ | 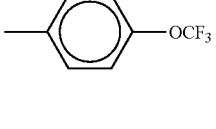 |
| (832) | C₅H₁₁ | —CF₃ | 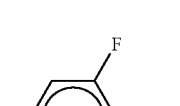 |
| (833) | —C₃H₇ | —CF₃ | 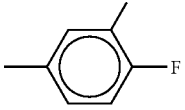 |
| (834) | C₅H₁₁ | —CF₃ | 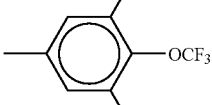 |
| (835) | —C₃H₇ | —CF₃ | 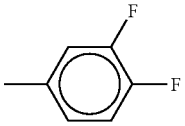 |
| (836) | C₅H₁₁ | —CF₃ | 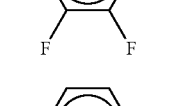 |
| (837) | —C₃H₇ | —CF₃ | 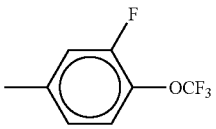 |

-continued
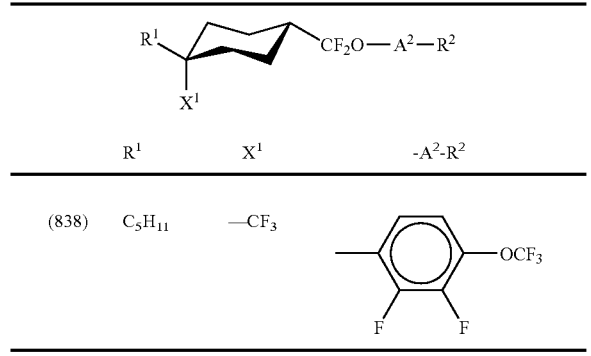
| | R¹ | X¹ | -A²-R² |
|---|---|---|---|
| (838) | C₅H₁₁ | —CF₃ | |
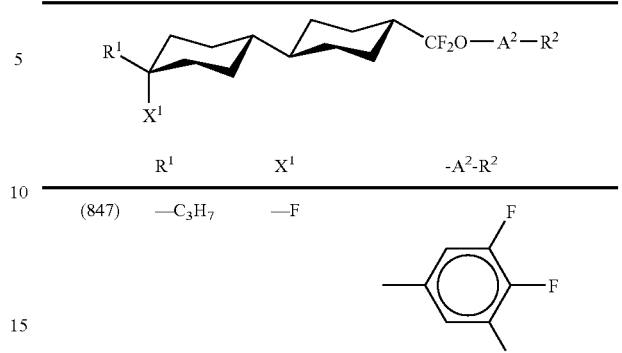
| | R¹ | X¹ | -A²-R² |
|---|---|---|---|
| (847) | —C₃H₇ | —F | |
| (848) | C₅H₁₁ | —F | |
| (849) | —C₃H₇ | —F | |
| (850) | C₅H₁₁ | —F | |
| (851) | —C₃H₇ | —F | |
| (852) | C₅H₁₁ | —F | |
| (853) | —C₃H₇ | —F | |
| (854) | C₅H₁₁ | —F | |
| (855) | —C₃H₇ | —CH₃ | |
Furthermore, compounds of the formulae shown below are obtained analogously to the previous examples:
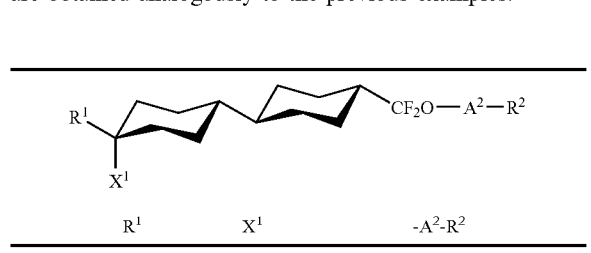
| | R¹ | X¹ | -A²-R² |
|---|---|---|---|
| (839) | —C₃H₇ | —F | |
| (840) | C₅H₁₁ | —F | |
| (841) | —C₃H₇ | —F | |
| (842) | C₅H₁₁ | —F | |
| (843) | —C₃H₇ | —F | |
| (844) | C₅H₁₁ | —F | |
| (845) | —C₃H₇ | —F | |
| (846) | C₅H₁₁ | —F | |

-continued

| | R¹ | X¹ | -A²-R² |
|---|---|---|---|
| (856) | C₅H₁₁ | —CH₃ | 4-F-phenyl |
| (857) | —C₃H₇ | —CH₃ | 4-OCF₃-phenyl |
| (858) | C₅H₁₁ | —CH₃ | 4-OCF₃-phenyl |
| (859) | —C₃H₇ | —CH₃ | 3,4-di-F-phenyl |
| (860) | C₅H₁₁ | —CH₃ | 3,4-di-F-phenyl |
| (861) | —C₃H₇ | —CH₃ | 3-F-4-OCF₃-phenyl |
| (862) | C₅H₁₁ | —CH₃ | 3-F-4-OCF₃-phenyl |
| (863) | —C₃H₇ | —CH₃ | 3,4,5-tri-F-phenyl |
| (864) | C₅H₁₁ | —CH₃ | 3,4,5-tri-F-phenyl |
| (865) | —C₃H₇ | —CH₃ | 3,5-di-F-4-OCF₃-phenyl |

-continued

| | R¹ | X¹ | -A²-R² |
|---|---|---|---|
| (866) | C₅H₁₁ | —CH₃ | 3,5-di-F-4-OCF₃-phenyl |
| (867) | —C₃H₇ | —CH₃ | 2,3,4-tri-F-phenyl |
| (868) | C₅H₁₁ | —CH₃ | 2,3,4-tri-F-phenyl |
| (869) | —C₃H₇ | —CH₃ | 2,3-di-F-4-OCF₃-phenyl |
| (870) | C₅H₁₁ | —CH₃ | 2,3-di-F-4-OCF₃-phenyl |
| (871) | —C₃H₇ | —CF₃ | 4-F-phenyl |
| (872) | C₅H₁₁ | —CF₃ | 4-F-phenyl |
| (873) | —C₃H₇ | —CF₃ | 4-OCF₃-phenyl |
| (874) | C₅H₁₁ | —CF₃ | 4-OCF₃-phenyl |
| (875) | —C₃H₇ | —CF₃ | 3,4-di-F-phenyl |
| (876) | C₅H₁₁ | —CF₃ | 3,4-di-F-phenyl |

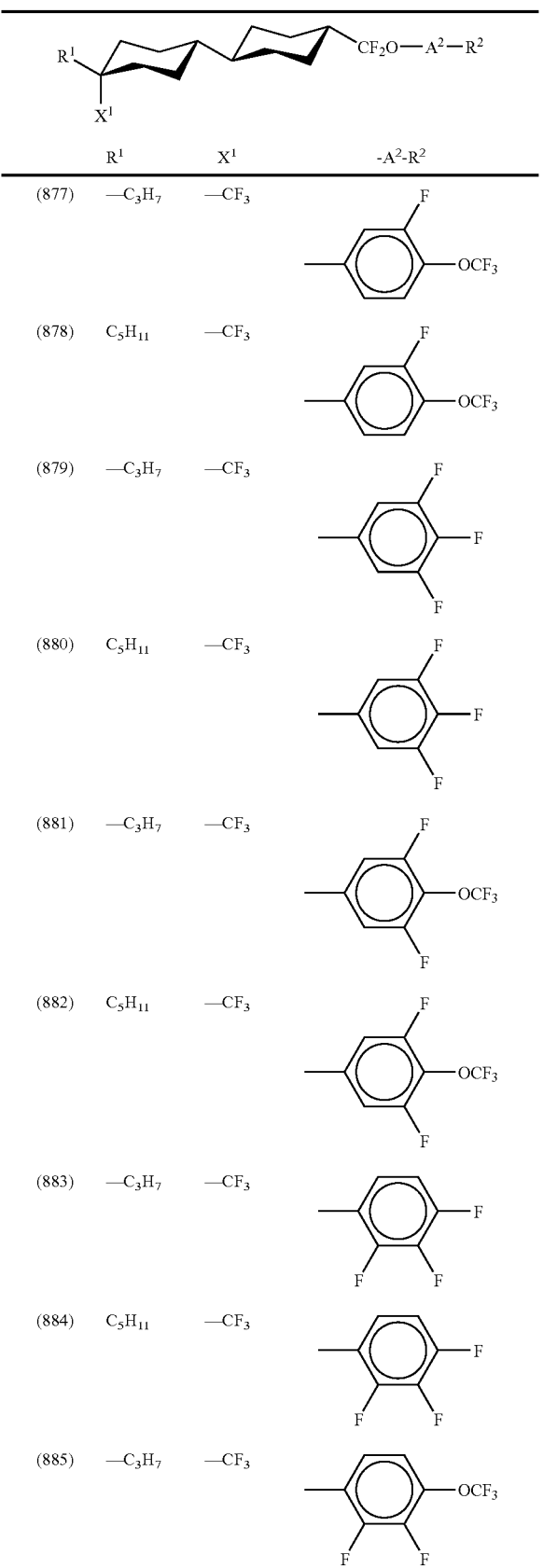
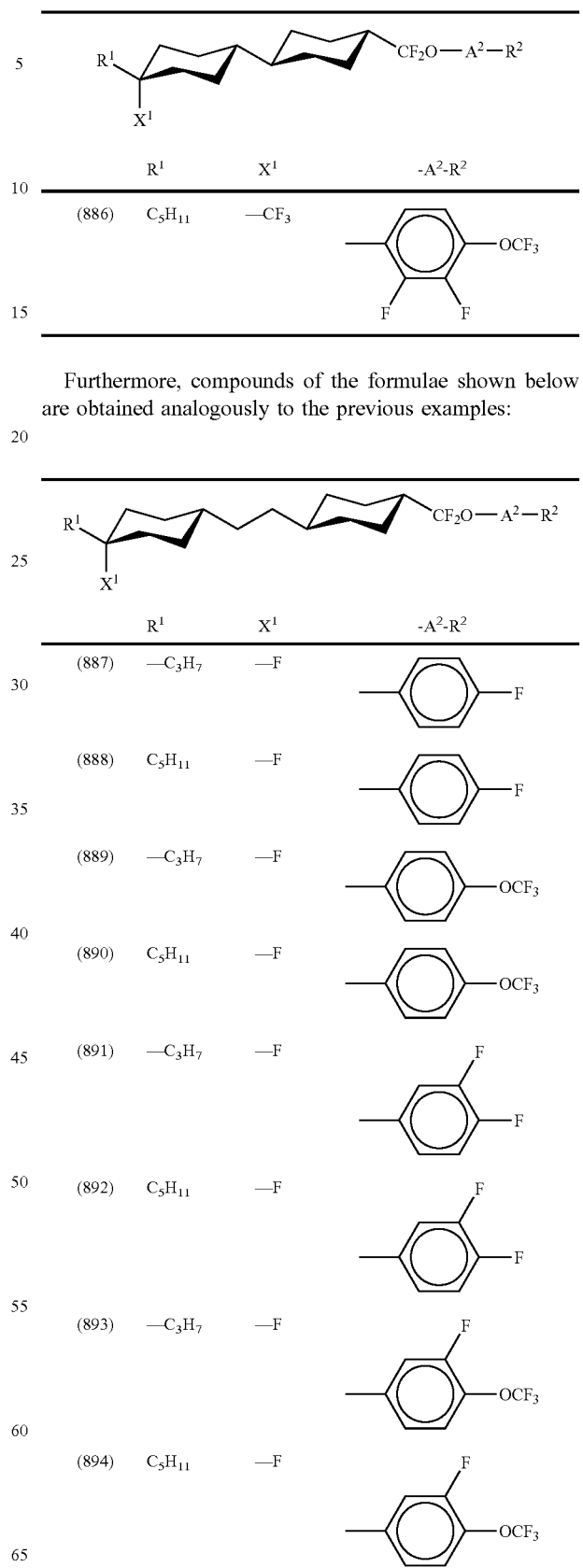
Furthermore, compounds of the formulae shown below are obtained analogously to the previous examples:

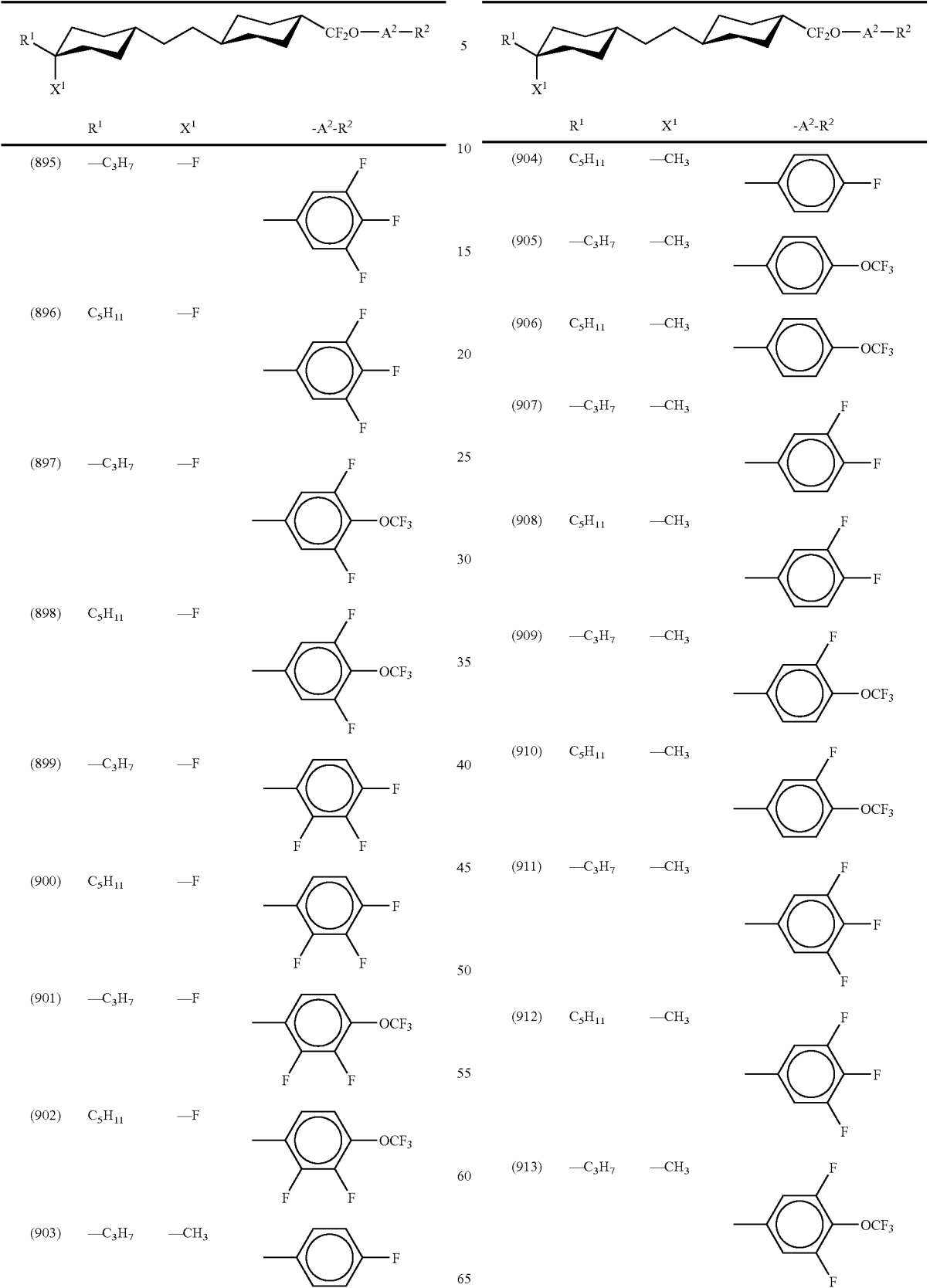

-continued

| | R¹ | X¹ | -A²-R² |
|---|---|---|---|
| (914) | $C_5H_{11}$ | —$CH_3$ | 2,6-difluoro-4-OCF₃ phenyl |
| (915) | —$C_3H_7$ | —$CH_3$ | 3,4,5-trifluorophenyl |
| (916) | $C_5H_{11}$ | —$CH_3$ | 3,4,5-trifluorophenyl |
| (917) | —$C_3H_7$ | —$CH_3$ | 3,4-difluoro-4-OCF₃ phenyl |
| (918) | $C_5H_{11}$ | —$CH_3$ | 3,4-difluoro-4-OCF₃ phenyl |
| (919) | —$C_3H_7$ | —$CF_3$ | 4-fluorophenyl |
| (920) | $C_5H_{11}$ | —$CF_3$ | 4-fluorophenyl |
| (921) | —$C_3H_7$ | —$CF_3$ | 4-OCF₃ phenyl |
| (922) | $C_5H_{11}$ | —$CF_3$ | 4-OCF₃ phenyl |
| (923) | —$C_3H_7$ | —$CF_3$ | 3,4-difluorophenyl |
| (924) | $C_5H_{11}$ | —$CF_3$ | 3,4-difluorophenyl |

| | R¹ | X¹ | -A²-R² |
|---|---|---|---|
| (925) | —$C_3H_7$ | —$CF_3$ | 3-fluoro-4-OCF₃ phenyl |
| (926) | $C_5H_{11}$ | —$CF_3$ | 3-fluoro-4-OCF₃ phenyl |
| (927) | —$C_3H_7$ | —$CF_3$ | 3,4,5-trifluorophenyl |
| (928) | $C_5H_{11}$ | —$CF_3$ | 3,4,5-trifluorophenyl |
| (929) | —$C_3H_7$ | —$CF_3$ | 3,5-difluoro-4-OCF₃ phenyl |
| (930) | $C_5H_{11}$ | —$CF_3$ | 3,5-difluoro-4-OCF₃ phenyl |
| (931) | —$C_3H_7$ | —$CF_3$ | 3,4,5-trifluorophenyl |
| (932) | $C_5H_{11}$ | —$CF_3$ | 3,4,5-trifluorophenyl |
| (933) | —$C_3H_7$ | —$CF_3$ | 3,4-difluoro-4-OCF₃ phenyl |

-continued
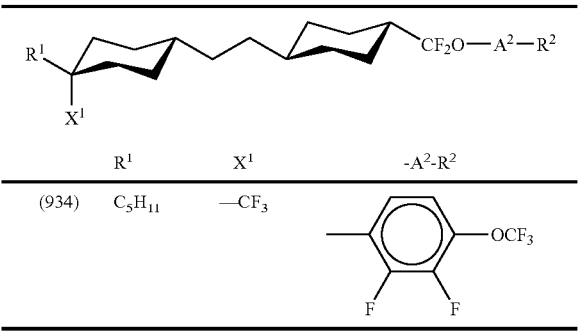
| | R¹ | X¹ | -A²-R² |
|---|---|---|---|
| (934) | C₅H₁₁ | —CF₃ |  |
Furthermore, compounds of the formulae shown below are obtained analogously to the previous examples:
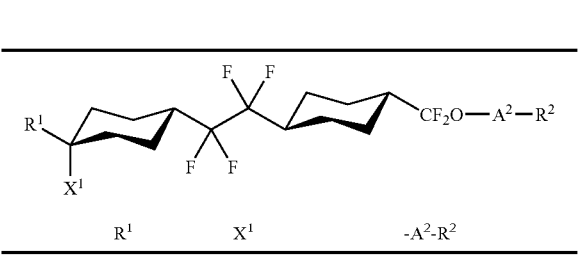
| | R¹ | X¹ | -A²-R² |
|---|---|---|---|
| (935) | —C₃H₇ | —F | 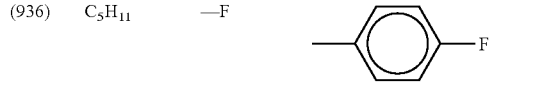 |
| (936) | C₅H₁₁ | —F | 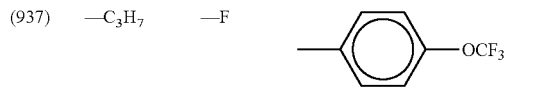 |
| (937) | —C₃H₇ | —F | 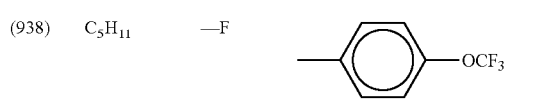 |
| (938) | C₅H₁₁ | —F |  |
| (939) | —C₃H₇ | —F |  |
| (940) | C₅H₁₁ | —F |  |
| (941) | —C₃H₇ | —F | 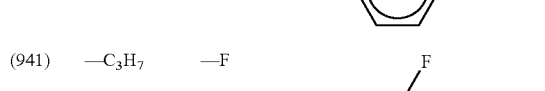 |
| (942) | C₅H₁₁ | —F | 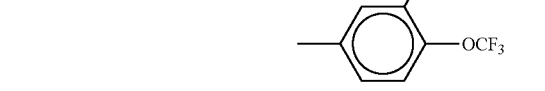 |
-continued
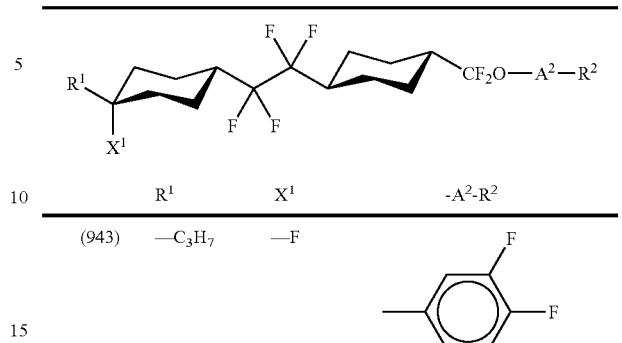
| | R¹ | X¹ | -A²-R² |
|---|---|---|---|
| (943) | —C₃H₇ | —F |  |
| (944) | C₅H₁₁ | —F | 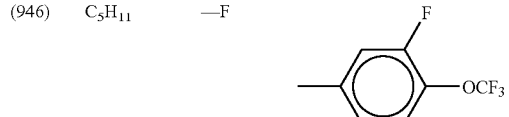 |
| (945) | —C₃H₇ | —F |  |
| (946) | C₅H₁₁ | —F | 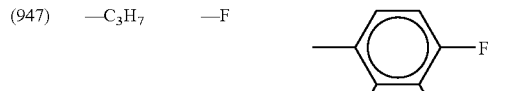 |
| (947) | —C₃H₇ | —F | 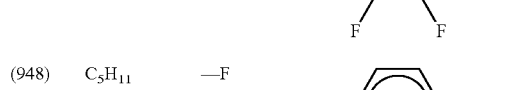 |
| (948) | C₅H₁₁ | —F |  |
| (949) | —C₃H₇ | —F | 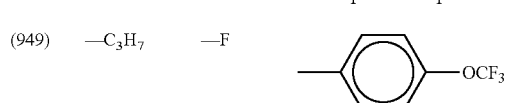 |
| (950) | C₅H₁₁ | —F |  |
| (951) | —C₃H₇ | —CH₃ | 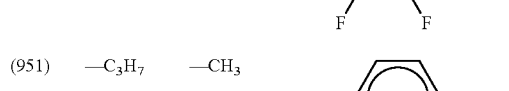 |

-continued $R^1$-[cyclohexyl]-$CF_2CF_2$-[cyclohexyl]-$CF_2O$-$A^2$-$R^2$, with $X^1$ on first ring

| | $R^1$ | $X^1$ | $-A^2-R^2$ |
|---|---|---|---|
| (952) | $C_5H_{11}$ | —$CH_3$ | 4-F-phenyl |
| (953) | —$C_3H_7$ | —$CH_3$ | 4-$OCF_3$-phenyl |
| (954) | $C_5H_{11}$ | —$CH_3$ | 4-$OCF_3$-phenyl |
| (955) | —$C_3H_7$ | —$CH_3$ | 3,4-diF-phenyl |
| (956) | $C_5H_{11}$ | —$CH_3$ | 3,4-diF-phenyl |
| (957) | —$C_3H_7$ | —$CH_3$ | 3-F-4-$OCF_3$-phenyl |
| (958) | $C_5H_{11}$ | —$CH_3$ | 3-F-4-$OCF_3$-phenyl |
| (959) | —$C_3H_7$ | —$CH_3$ | 3,4,5-triF-phenyl |
| (960) | $C_5H_{11}$ | —$CH_3$ | 3,4,5-triF-phenyl |
| (961) | —$C_3H_7$ | —$CH_3$ | 3,5-diF-4-$OCF_3$-phenyl |
| (962) | $C_5H_{11}$ | —$CH_3$ | 3,5-diF-4-$OCF_3$-phenyl |
| (963) | —$C_3H_7$ | —$CH_3$ | 3,4,5-triF-phenyl |
| (964) | $C_5H_{11}$ | —$CH_3$ | 3,4,5-triF-phenyl |
| (965) | —$C_3H_7$ | —$CH_3$ | 3,5-diF-4-$OCF_3$-phenyl |
| (966) | $C_5H_{11}$ | —$CH_3$ | 3,5-diF-4-$OCF_3$-phenyl |
| (967) | —$C_3H_7$ | —$CF_3$ | 4-F-phenyl |
| (968) | $C_5H_{11}$ | —$CF_3$ | 4-F-phenyl |
| (969) | —$C_3H_7$ | —$CF_3$ | 4-$OCF_3$-phenyl |
| (970) | $C_5H_{11}$ | —$CF_3$ | 4-$OCF_3$-phenyl |
| (971) | —$C_3H_7$ | —$CF_3$ | 3,4-diF-phenyl |
| (972) | $C_5H_{11}$ | —$CF_3$ | 3,4-diF-phenyl |

-continued
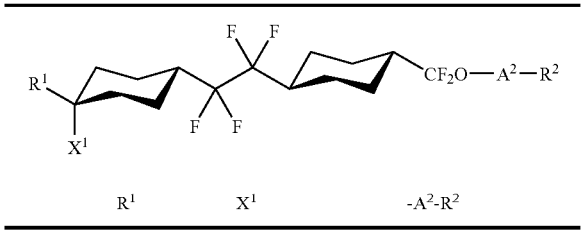
| | R¹ | X¹ | -A²-R² |
|---|---|---|---|
| (973) | —C₃H₇ | —CF₃ | 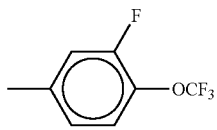 |
| (974) | C₅H₁₁ | —CF₃ | 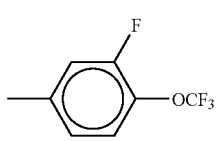 |
| (975) | —C₃H₇ | —CF₃ | 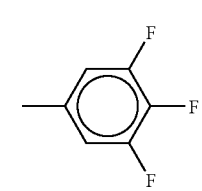 |
| (976) | C₅H₁₁ | —CF₃ | 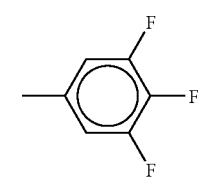 |
| (977) | —C₃H₇ | —CF₃ | 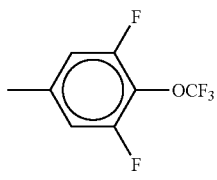 |
| (978) | C₅H₁₁ | —CF₃ | 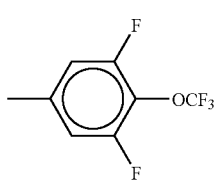 |
| (979) | —C₃H₇ | —CF₃ | 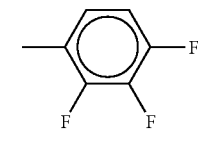 |
| (980) | C₅H₁₁ | —CF₃ | 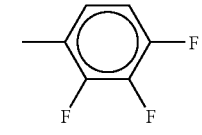 |
-continued
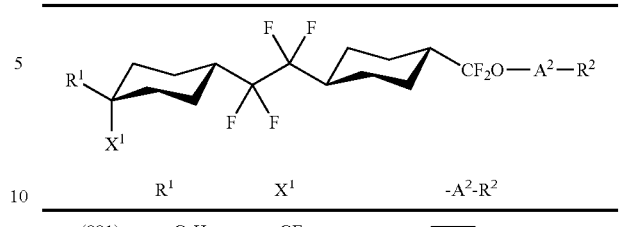
| | R¹ | X¹ | -A²-R² |
|---|---|---|---|
| (981) | —C₃H₇ | —CF₃ | 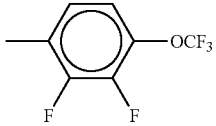 |
| (982) | C₅H₁₁ | —CF₃ | 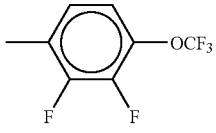 |
Furthermore, compounds of the formulae shown below are obtained analogously to the previous examples:
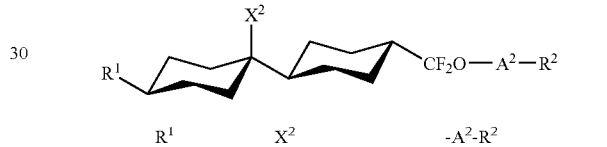
| | R¹ | X² | -A²-R² |
|---|---|---|---|
| (983) | —C₃H₇ | —F | 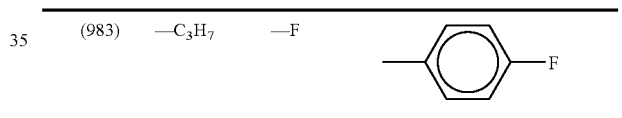 |
| (984) | C₅H₁₁ | —F | 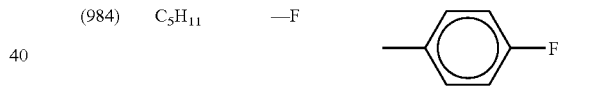 |
| (985) | —C₃H₇ | —F | 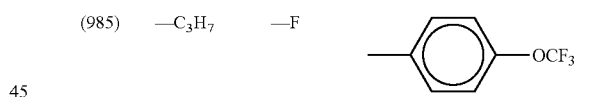 |
| (986) | C₅H₁₁ | —F | 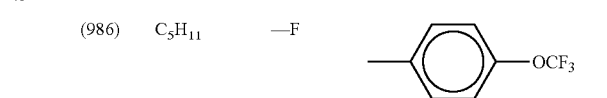 |
| (987) | —C₃H₇ | —F | 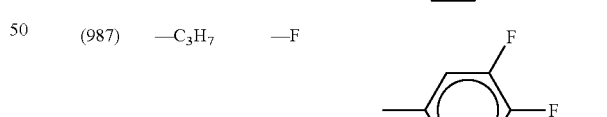 |
| (988) | C₅H₁₁ | —F | 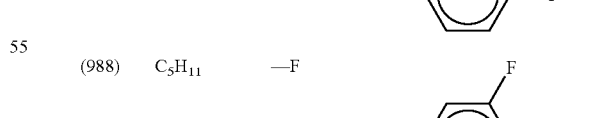 |
| (989) | —C₃H₇ | —F | 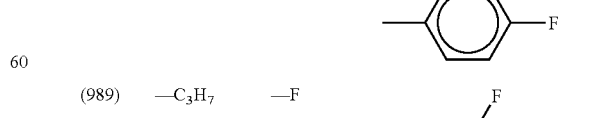 |

-continued
| | R¹ | X² | -A²-R² |
|---|---|---|---|
| (990) | C₅H₁₁ | —F | 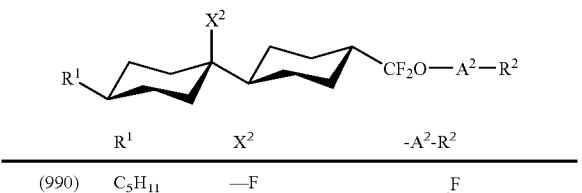 |
| (991) | —C₃H₇ | —F |  |
| (992) | C₅H₁₁ | —F | 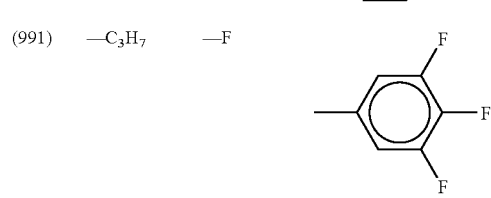 |
| (993) | —C₃H₇ | —F | 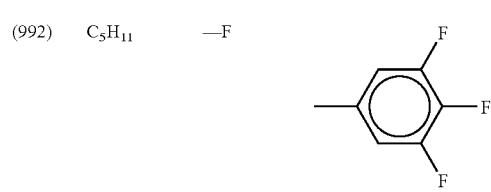 |
| (994) | C₅H₁₁ | —F | 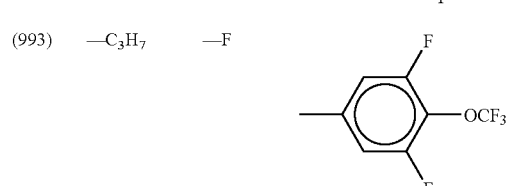 |
| (995) | —C₃H₇ | —F | 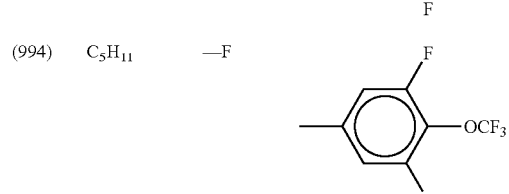 |
| (996) | C₅H₁₁ | —F | 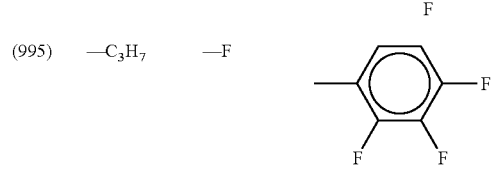 |
| (997) | —C₃H₇ | —F | 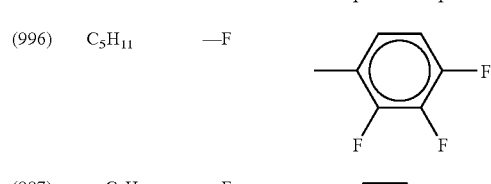 |
| (998) | C₅H₁₁ | —F | 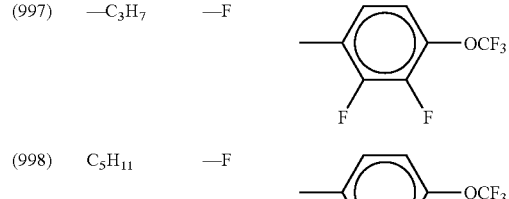 |
-continued
| | R¹ | X² | -A²-R² |
|---|---|---|---|
| (999) | —C₃H₇ | —CH₃ | 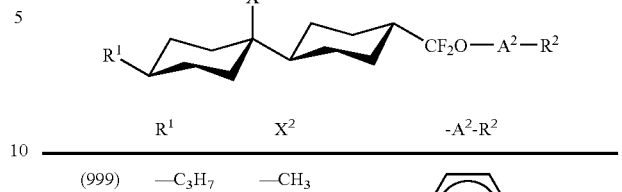 |
| (1000) | C₅H₁₁ | —CH₃ |  |
| (1001) | —C₃H₇ | —CH₃ | 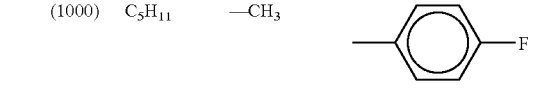 |
| (1002) | C₅H₁₁ | —CH₃ | 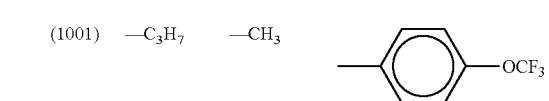 |
| (1003) | —C₃H₇ | —CH₃ | 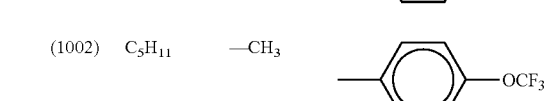 |
| (1004) | C₅H₁₁ | —CH₃ | 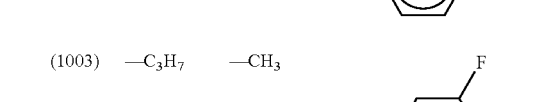 |
| (1005) | —C₃H₇ | —CH₃ |  |
| (1006) | C₅H₁₁ | —CH₃ | 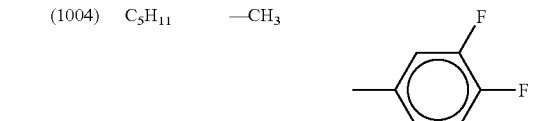 |
| (1007) | —C₃H₇ | —CH₃ | 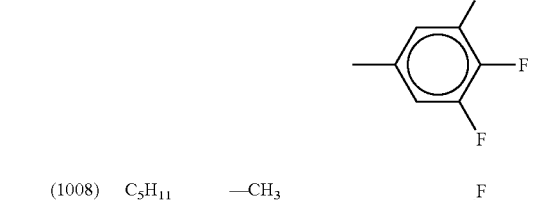 |
| (1008) | C₅H₁₁ | —CH₃ |  |

-continued
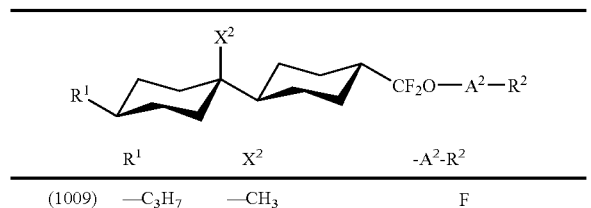
| | R¹ | X² | -A²-R² |
|---|---|---|---|
| (1009) | —C₃H₇ | —CH₃ | 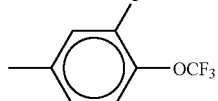 |
| (1010) | C₅H₁₁ | —CH₃ | 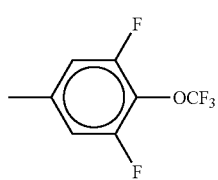 |
| (1011) | —C₃H₇ | —CH₃ | 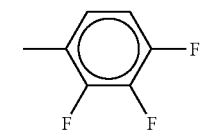 |
| (1012) | C₅H₁₁ | —CH₃ | 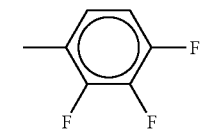 |
| (1013) | —C₃H₇ | —CH₃ | 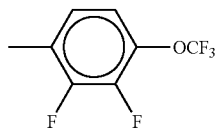 |
| (1014) | C₅H₁₁ | —CH₃ | 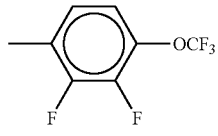 |
| (1015) | —C₃H₇ | —CF₃ | 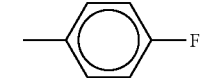 |
| (1016) | C₅H₁₁ | —CF₃ | 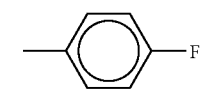 |
| (1017) | —C₃H₇ | —CF₃ | 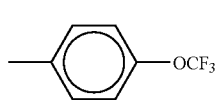 |
| (1018) | C₅H₁₁ | —CF₃ | 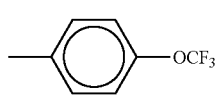 |
| (1019) | —C₃H₇ | —CF₃ | 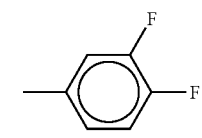 |
-continued
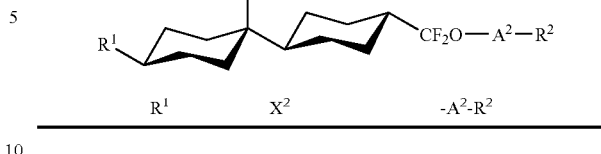
| | R¹ | X² | -A²-R² |
|---|---|---|---|
| (1020) | C₅H₁₁ | —CF₃ | 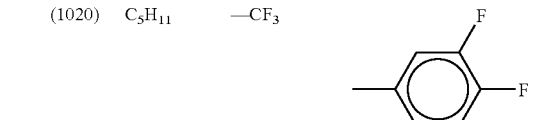 |
| (1021) | —C₃H₇ | —CF₃ |  |
| (1022) | C₅H₁₁ | —CF₃ |  |
| (1023) | —C₃H₇ | —CF₃ |  |
| (1024) | C₅H₁₁ | —CF₃ |  |
| (1025) | —C₃H₇ | —CF₃ | 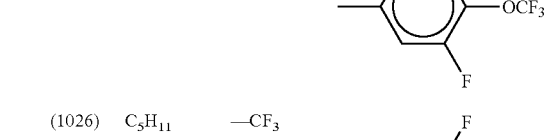 |
| (1026) | C₅H₁₁ | —CF₃ | 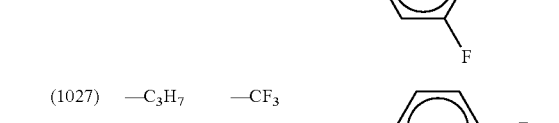 |
| (1027) | —C₃H₇ | —CF₃ | 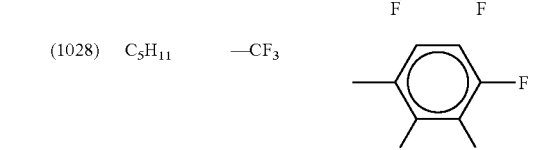 |
| (1028) | C₅H₁₁ | —CF₃ | |

-continued
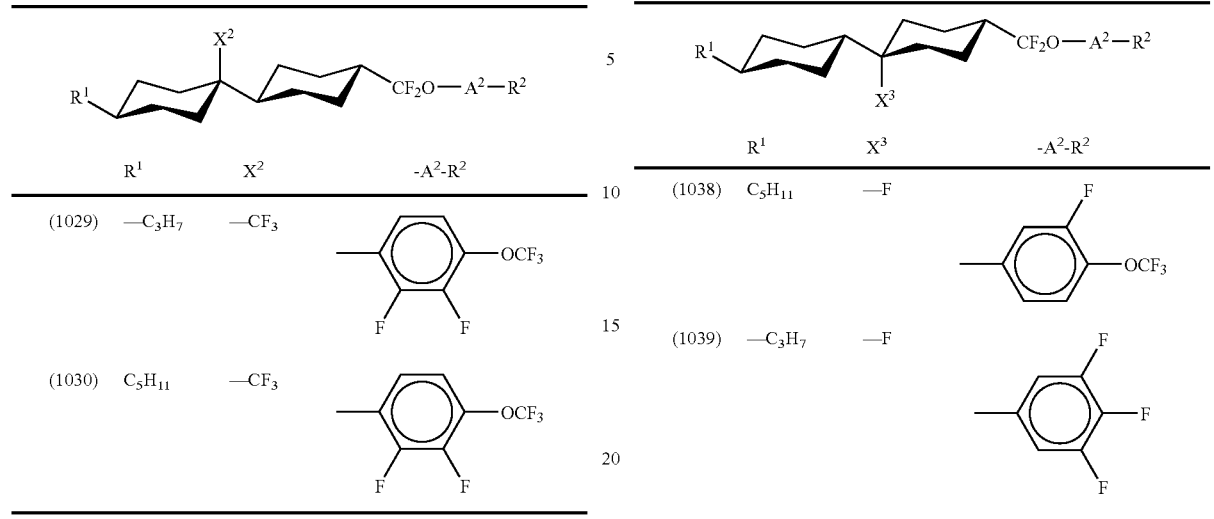
Furthermore, compounds of the formulae shown below are obtained analogously to the previous examples:
-continued
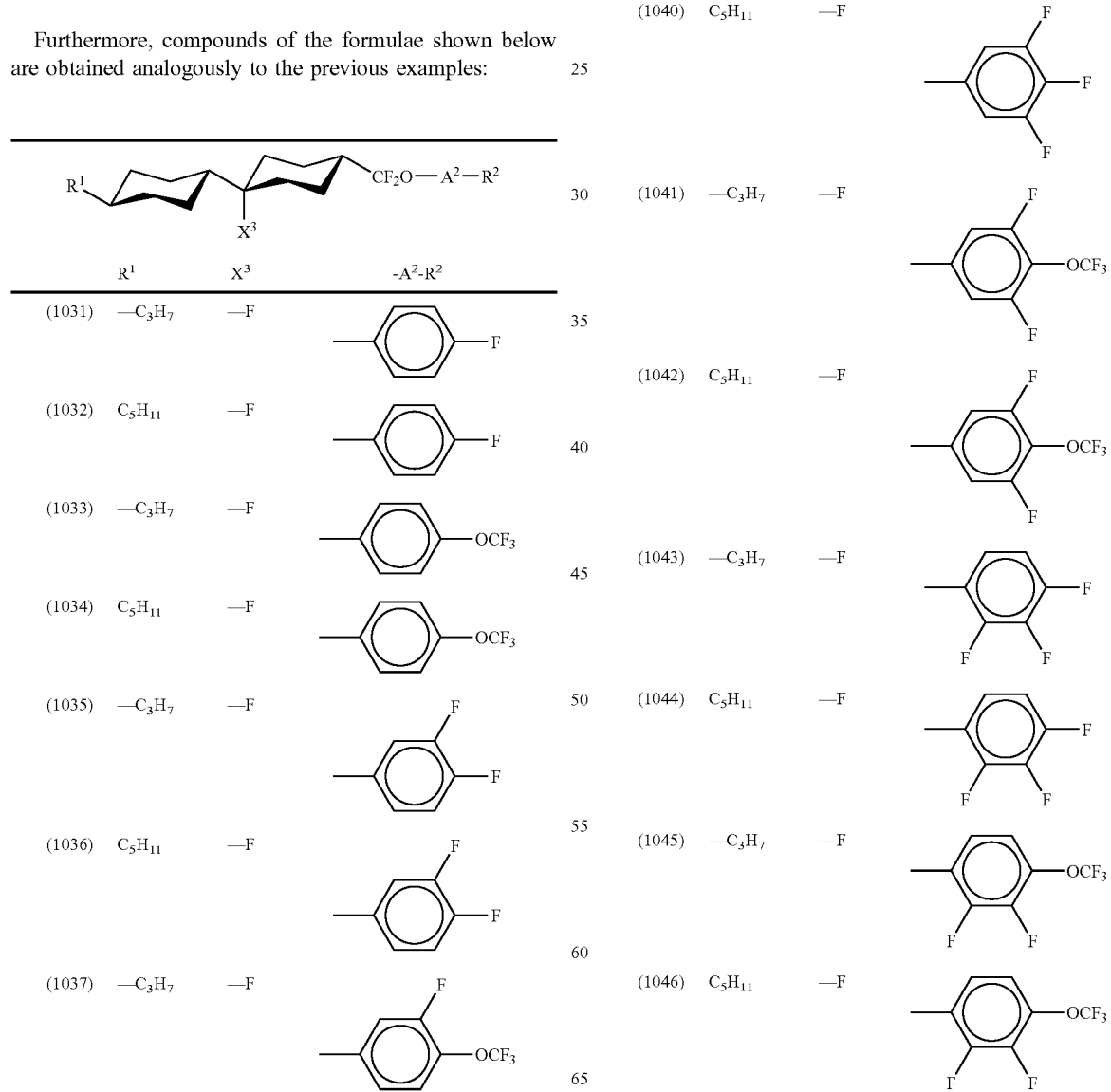

-continued

| | R¹ | X³ | -A²-R² |
|---|---|---|---|
| (1047) | —C₃H₇ | —CH₃ | 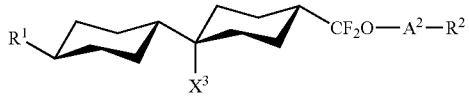 4-F-phenyl |
| (1048) | C₅H₁₁ | —CH₃ | 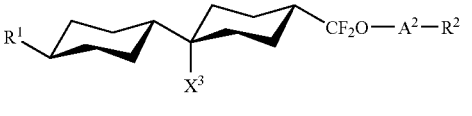 4-F-phenyl |
| (1049) | —C₃H₇ | —CH₃ |  4-OCF₃-phenyl |
| (1050) | C₅H₁₁ | —CH₃ | 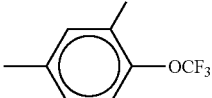 4-OCF₃-phenyl |
| (1051) | —C₃H₇ | —CH₃ |  3,4-diF-phenyl |
| (1052) | C₅H₁₁ | —CH₃ | 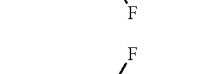 3,4-diF-phenyl |
| (1053) | —C₃H₇ | —CH₃ | 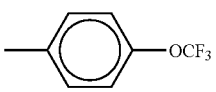 3-F-4-OCF₃-phenyl |
| (1054) | C₅H₁₁ | —CH₃ | 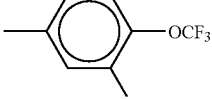 3-F-4-OCF₃-phenyl |
| (1055) | —C₃H₇ | —CH₃ | 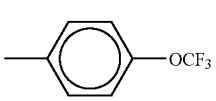 3,4,5-triF-phenyl |
| (1056) | C₅H₁₁ | —CH₃ |  3,4,5-triF-phenyl |

-continued

| | R¹ | X³ | -A²-R² |
|---|---|---|---|
| (1057) | —C₃H₇ | —CH₃ | 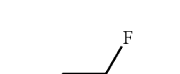 3,5-diF-4-OCF₃-phenyl |
| (1058) | C₅H₁₁ | —CH₃ |  3,5-diF-4-OCF₃-phenyl |
| (1059) | —C₃H₇ | —CH₃ |  3,4,5-triF-phenyl |
| (1060) | C₅H₁₁ | —CH₃ |  3,4,5-triF-phenyl |
| (1061) | —C₃H₇ | —CH₃ | 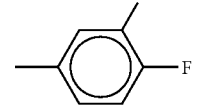 3,5-diF-4-OCF₃-phenyl |
| (1062) | C₅H₁₁ | —CH₃ | 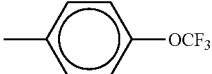 3,5-diF-4-OCF₃-phenyl |
| (1063) | —C₃H₇ | —CF₃ | 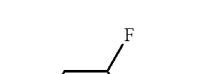 4-F-phenyl |
| (1064) | C₅H₁₁ | —CF₃ | 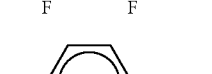 4-F-phenyl |
| (1065) | —C₃H₇ | —CF₃ |  4-OCF₃-phenyl |
| (1066) | C₅H₁₁ | —CF₃ | 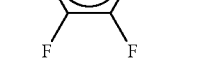 4-OCF₃-phenyl |
| (1067) | —C₃H₇ | —CF₃ | 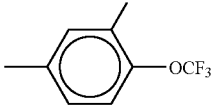 3,4-diF-phenyl |

-continued
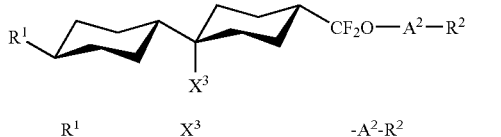
| | R¹ | X³ | -A²-R² |
|---|---|---|---|
| (1068) | C₅H₁₁ | —CF₃ | 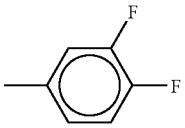 |
| (1069) | —C₃H₇ | —CF₃ | 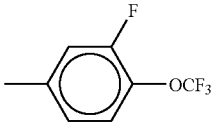 |
| (1070) | C₅H₁₁ | —CF₃ | 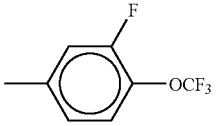 |
| (1071) | —C₃H₇ | —CF₃ | 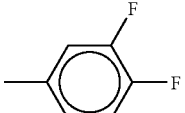 |
| (1072) | C₅H₁₁ | —CF₃ | 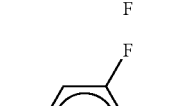 |
| (1073) | —C₃H₇ | —CF₃ | 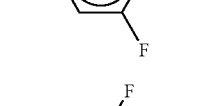 |
| (1074) | C₅H₁₁ | —CF₃ | 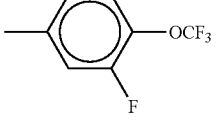 |
| (1075) | —C₃H₇ | —CF₃ | 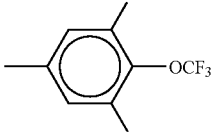 |
| (1076) | C₅H₁₁ | —CF₃ | 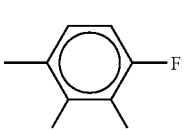 |
-continued
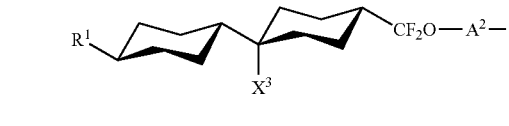
| | R¹ | X³ | -A²-R² |
|---|---|---|---|
| (1077) | —C₃H₇ | —CF₃ | 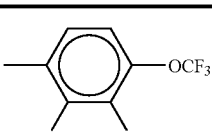 |
| (1078) | C₅H₁₁ | —CF₃ | 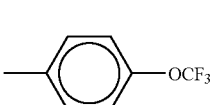 |
Furthermore, compounds of the formulae shown below are obtained analogously to the previous examples:
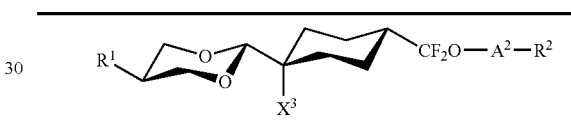
| | R¹ | X³ | -A²-R² |
|---|---|---|---|
| (1079) | —C₃H₇ | —F | 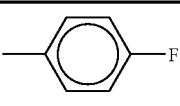 |
| (1080) | C₅H₁₁ | —F |  |
| (1081) | —C₃H₇ | —F | 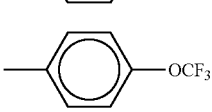 |
| (1082) | C₅H₁₁ | —F | 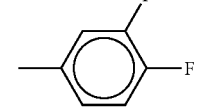 |
| (1083) | —C₃H₇ | —F | 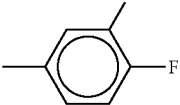 |
| (1084) | C₅H₁₁ | —F | 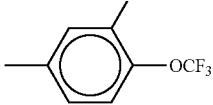 |
| (1085) | —C₃H₇ | —F |  |

-continued

| | R¹ | X³ | -A²-R² |
|---|---|---|---|
| (1086) | C₅H₁₁ | —F | 2-F, 4-OCF₃ phenyl |
| (1087) | —C₃H₇ | —F | 3,4,5-triF phenyl |
| (1088) | C₅H₁₁ | —F | 3,4,5-triF phenyl |
| (1089) | —C₃H₇ | —F | 3,5-diF, 4-OCF₃ phenyl |
| (1090) | C₅H₁₁ | —F | 3,5-diF, 4-OCF₃ phenyl |
| (1091) | —C₃H₇ | —F | 2,3,4-triF phenyl |
| (1092) | C₅H₁₁ | —F | 2,3,4-triF phenyl |
| (1093) | —C₃H₇ | —F | 2,3-diF, 4-OCF₃ phenyl |
| (1094) | C₅H₁₁ | —F | 2,3-diF, 4-OCF₃ phenyl |

-continued

| | R¹ | X³ | -A²-R² |
|---|---|---|---|
| (1095) | —C₃H₇ | —CH₃ | 4-F phenyl |
| (1096) | C₅H₁₁ | —CH₃ | 4-F phenyl |
| (1097) | —C₃H₇ | —CH₃ | 4-OCF₃ phenyl |
| (1098) | C₅H₁₁ | —CH₃ | 4-OCF₃ phenyl |
| (1099) | —C₃H₇ | —CH₃ | 3,4-diF phenyl |
| (1100) | C₅H₁₁ | —CH₃ | 3,4-diF phenyl |
| (1101) | —C₃H₇ | —CH₃ | 3-F, 4-OCF₃ phenyl |
| (1102) | C₅H₁₁ | —CH₃ | 3-F, 4-OCF₃ phenyl |
| (1103) | —C₃H₇ | —CH₃ | 3,4,5-triF phenyl |
| (1104) | C₅H₁₁ | —CH₃ | 3,4,5-triF phenyl |

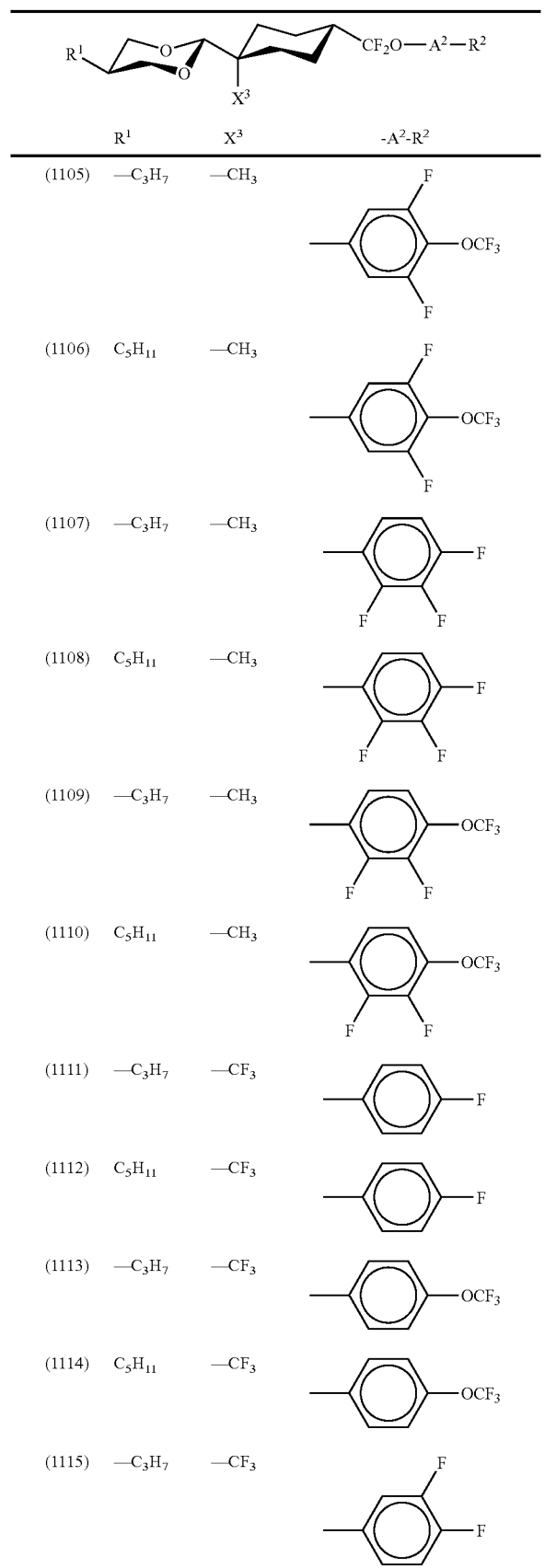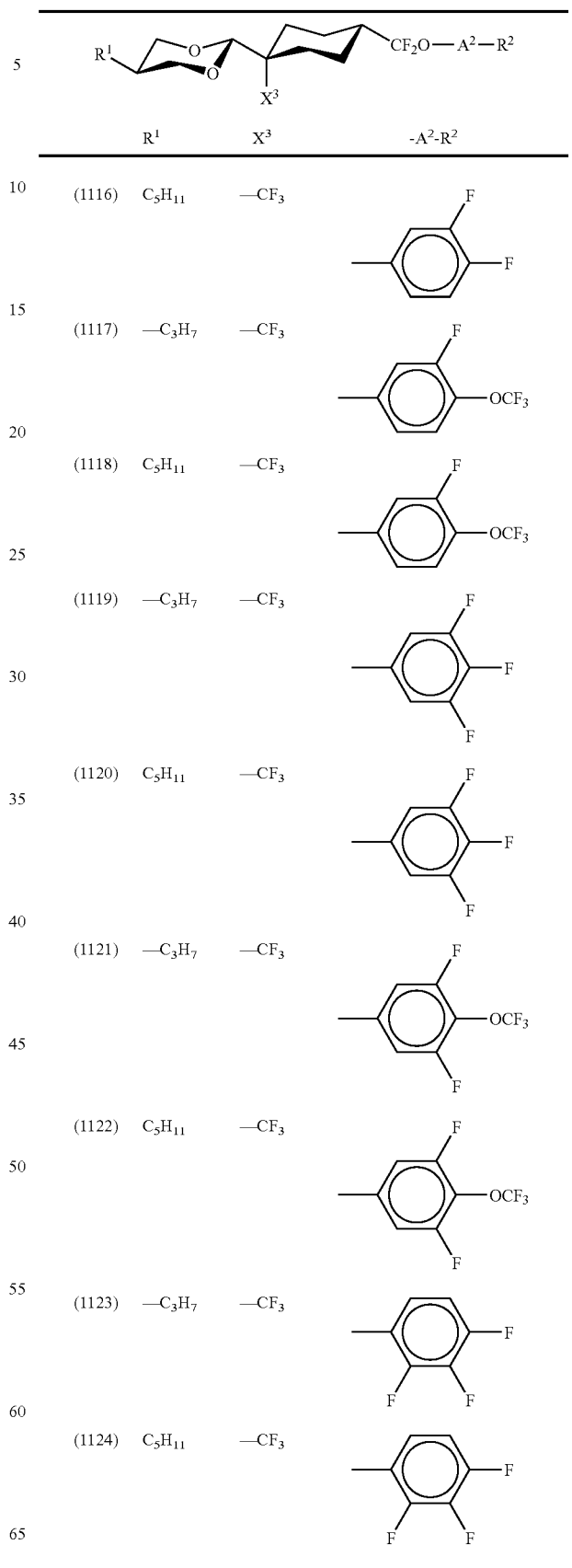

-continued

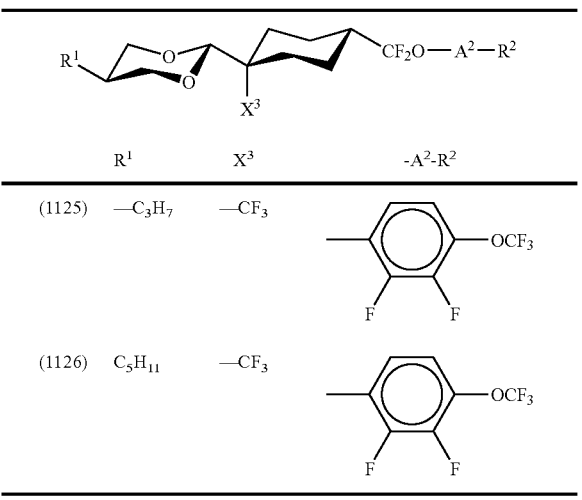

| | R¹ | X³ | -A²-R² |
|---|---|---|---|
| (1125) | —C₃H₇ | —CF₃ | (phenyl, 2,3-diF, 4-OCF₃) |
| (1126) | C₅H₁₁ | —CF₃ | (phenyl, 2,3-diF, 4-OCF₃) |

Furthermore, compounds of the formulae shown below are obtained analogously to the previous examples:

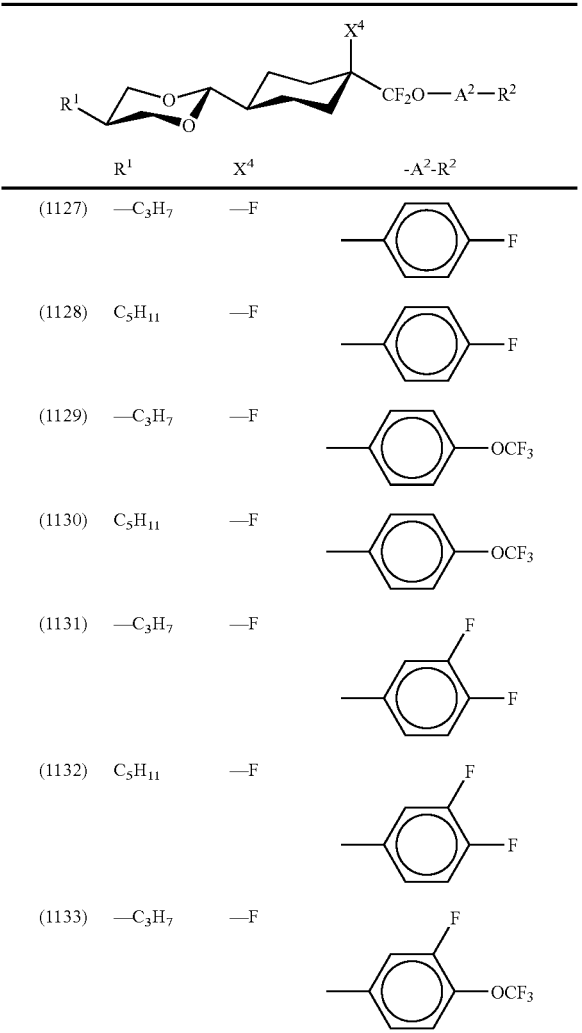

| | R¹ | X⁴ | -A²-R² |
|---|---|---|---|
| (1127) | —C₃H₇ | —F | (4-F-phenyl) |
| (1128) | C₅H₁₁ | —F | (4-F-phenyl) |
| (1129) | —C₃H₇ | —F | (4-OCF₃-phenyl) |
| (1130) | C₅H₁₁ | —F | (4-OCF₃-phenyl) |
| (1131) | —C₃H₇ | —F | (3,4-diF-phenyl) |
| (1132) | C₅H₁₁ | —F | (3,4-diF-phenyl) |
| (1133) | —C₃H₇ | —F | (3-F,4-OCF₃-phenyl) |

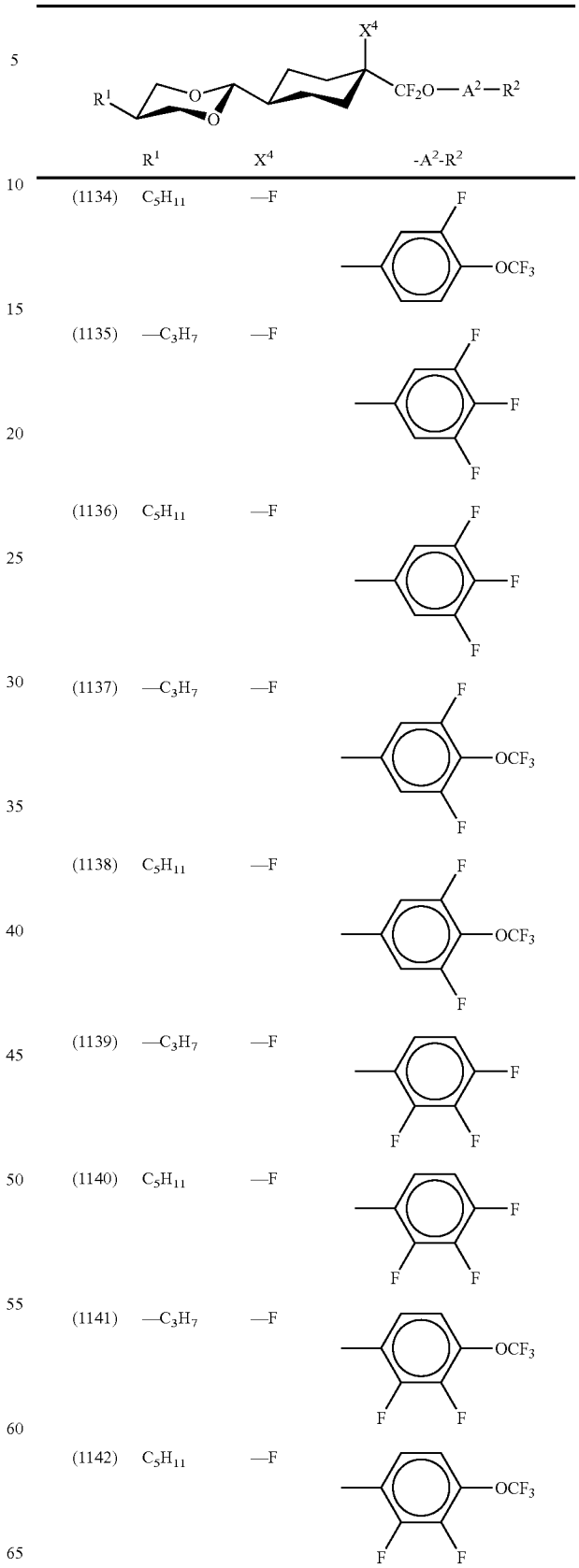

| | R¹ | X⁴ | -A²-R² |
|---|---|---|---|
| (1134) | C₅H₁₁ | —F | (3-F,4-OCF₃-phenyl) |
| (1135) | —C₃H₇ | —F | (3,4,5-triF-phenyl) |
| (1136) | C₅H₁₁ | —F | (3,4,5-triF-phenyl) |
| (1137) | —C₃H₇ | —F | (3,5-diF,4-OCF₃-phenyl) |
| (1138) | C₅H₁₁ | —F | (3,5-diF,4-OCF₃-phenyl) |
| (1139) | —C₃H₇ | —F | (2,3,4-triF-phenyl) |
| (1140) | C₅H₁₁ | —F | (2,3,4-triF-phenyl) |
| (1141) | —C₃H₇ | —F | (2,3-diF,4-OCF₃-phenyl) |
| (1142) | C₅H₁₁ | —F | (2,3-diF,4-OCF₃-phenyl) |

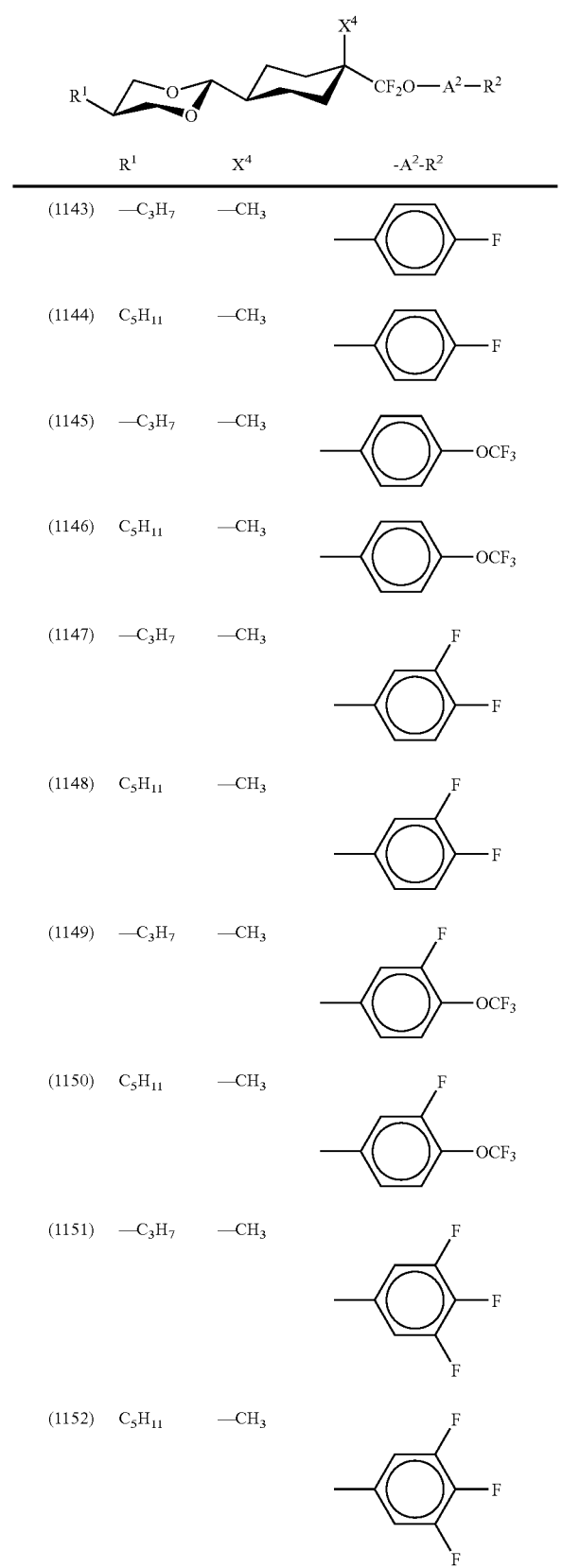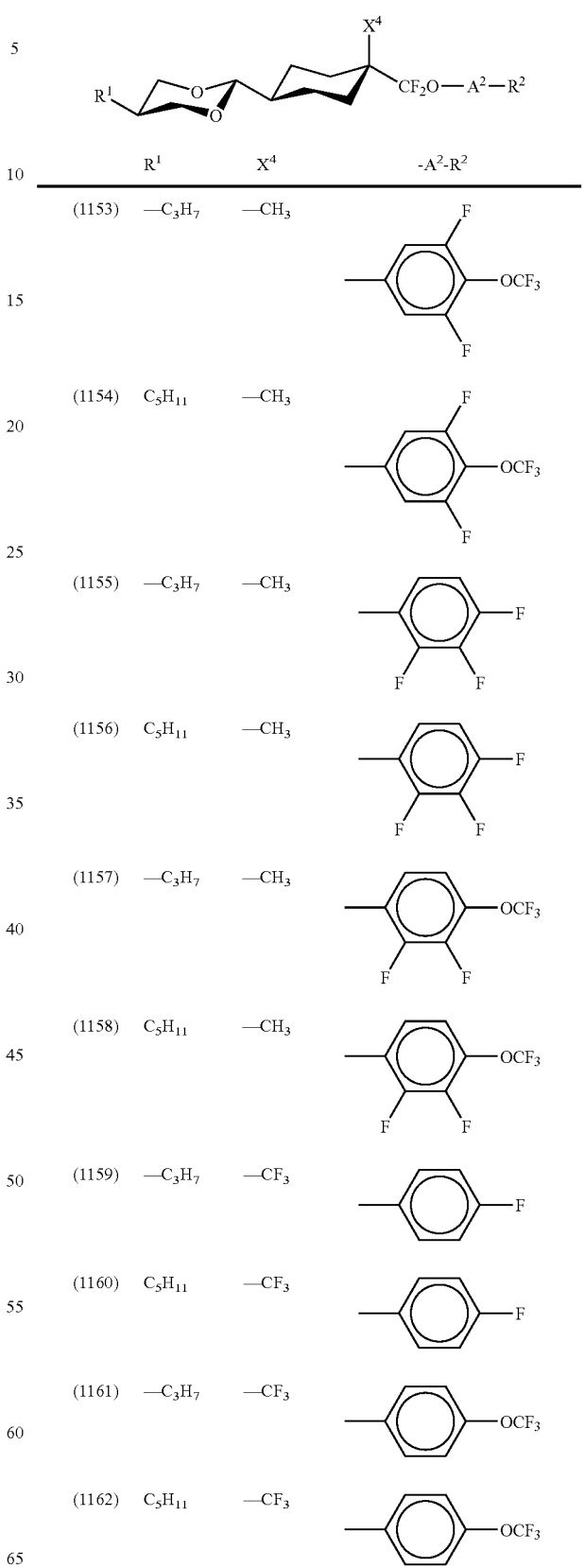

-continued

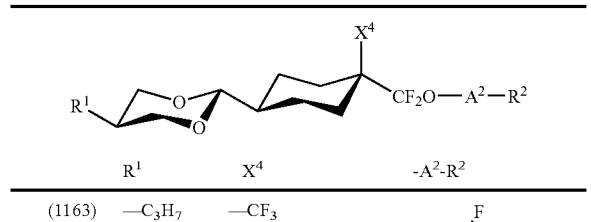

| | R¹ | X⁴ | -A²-R² |
|---|---|---|---|
| (1163) | —C₃H₇ | —CF₃ | 3,4-difluorophenyl |
| (1164) | C₅H₁₁ | —CF₃ | 3,4-difluorophenyl |
| (1165) | —C₃H₇ | —CF₃ | 3-fluoro-4-OCF₃-phenyl |
| (1166) | C₅H₁₁ | —CF₃ | 3-fluoro-4-OCF₃-phenyl |
| (1167) | —C₃H₇ | —CF₃ | 3,4,5-trifluorophenyl |
| (1168) | C₅H₁₁ | —CF₃ | 3,4,5-trifluorophenyl |
| (1169) | —C₃H₇ | —CF₃ | 3,5-difluoro-4-OCF₃-phenyl |
| (1170) | C₅H₁₁ | —CF₃ | 3,5-difluoro-4-OCF₃-phenyl |
| (1171) | —C₃H₇ | —CF₃ | 3,4,5-trifluorophenyl |

-continued

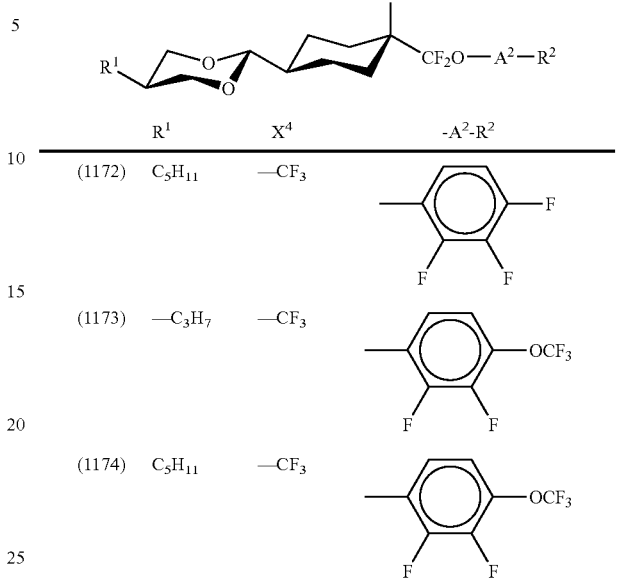

| | R¹ | X⁴ | -A²-R² |
|---|---|---|---|
| (1172) | C₅H₁₁ | —CF₃ | 3,4,5-trifluorophenyl |
| (1173) | —C₃H₇ | —CF₃ | 3,5-difluoro-4-OCF₃-phenyl |
| (1174) | C₅H₁₁ | —CF₃ | 3,5-difluoro-4-OCF₃-phenyl |

The invention claimed is:

1. A compound of the formula I $$R^1\text{-}(\text{-}A^1\text{-}Z^1\text{-})_{k1}\text{-}Q\text{-}CF_2O\text{-}A^2\text{-}(\text{-}Z^3\text{-}A^3\text{-})_{k3}\text{-}R^2 \qquad I$$

in which
Q is the

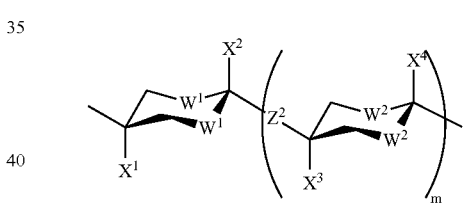

group, $W^1$ and $W^2$, independently of one another, are —CH₂— and/or —O—, $X^1$, $X^2$, $X^3$ and $X^4$, independently of one another, are H, F, —CH₃, —CH₂F, —CHF₂ and/or —CF₃, with the proviso that at least one substituent $X^1$, $X^2$, $X^3$ and/or $X^4$ is not H, $Z^2$ is a single bond, —CH₂—CH₂— or —CF₂—CF₂—, m is 0 or 1, $A^1$, $A^2$ and $A^3$, independently of one another, are
  a) a trans-1,4-cyclohexylene radical, in which one or more non-adjacent CH₂ groups are optionally replaced by —O— and/or —S—,
  b) a 1,4-phenylene radical, in which one or two CH groups are optionally replaced by N,
  c) a radical selected from the group consisting of 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl,
  d) 1,4-cyclohexenylene,
  where the radicals a), b) and d) are optionally substituted by CN, Cl or F, $Z^1$ and $Z^3$ are each, independently of one another, —CO—O—, —O—CO—, —O—, —CH₂—O—, —CF₂—

—O—, —O—CH$_2$—, —O—CF$_2$—, —C$_2$H$_4$—, —CH$_2$—CF$_2$—, —CF$_2$—CH$_2$—, —CF$_2$—CF$_2$—, —CH=CH—, —CF=CH—, —CH=CF—, —CF=CF—, —C≡C— or a single bond, R$^1$ and R$^2$, independently of one another, are H, halogen, —CN, —NCS, —SF$_5$ or alkyl having from 1 to 12 carbon atoms, in which one or two non-adjacent —CH$_2$— groups are optionally replaced by —O—, —S—, —CO—, —O—CO—, —CO—O—, —E— and/or —C≡C— and/or in which, one or more H atoms are optionally replaced by halogen and/or —CN, E is CR$^4$=CR$^5$ or CHR$^4$—CHR$^5$, R$^4$ and R$^5$ are each, independently of one another, H, alkyl having 1–6 carbon atoms, F, Cl, CF$_3$ or CN, k1 and k3, independently of one another, are 0, 1 or 2.

2. A compound according to claim 1, wherein Q is a sub-formula selected from the group consisting of the following sub-formulae:

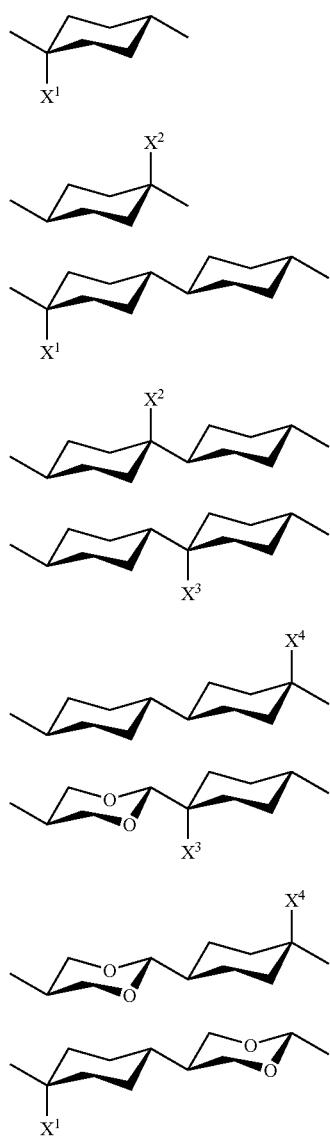

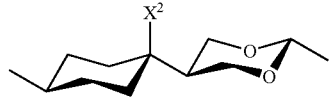

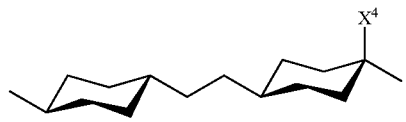

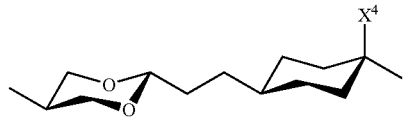

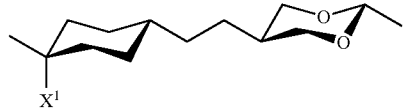

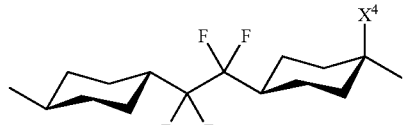

3. A compound according to claim 1, wherein k1=0 and k3=0 or 1.

4. A compound according to claim 1, wherein A$^2$ is a sub-formula selected from the group consisting of the sub-formulae

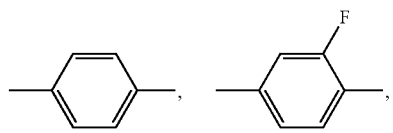

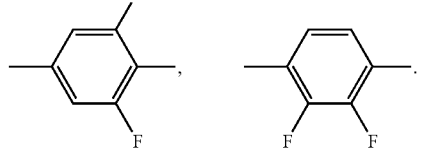

5. Liquid-crystalline medium having two or more liquid-crystalline components, which comprises at least one compound of the formula I according to claim 1.

6. Optical display element, which contains a liquid-crystalline medium according to claim 5.

7. Electro-optical display element, which contains, as dielectric, a liquid-crystalline medium according to claim 5.

8. A compound according to claim 1, wherein only one of X$^1$, X$^2$, X$^3$ or X$^4$ is —F, —CH$_3$, —CH$_2$F, —CHF$_2$ or —CF$_3$, while the other substituents X$^1$, X$^2$, X$^3$ and X$^4$, if present, are H.

9. A compound according to claim 1, wherein at least one of X$^1$, X$^2$, X$^3$ or X$^4$ is —F or —CF$_3$.

10. A compound according to claim 1, which is of one of the formulae Ia to If:

 Ia

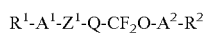 Ib

 Ic

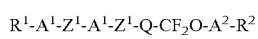 Id

 Ie

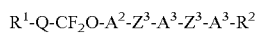 If wherein $A^1$, $A^2$ and $A^3$ are, independently of one another: 1,4-phenylene, which is optionally monosubstituted, disubstituted or trisubstituted by F, Cl and/or —CN; trans-1,4-cyclohexylene; 1,4-cyclohexenylene; or 1,3-dioxane-2,5-diyl.

11. A compound according to claim 1, which is of one of the formulae I1 to I14:

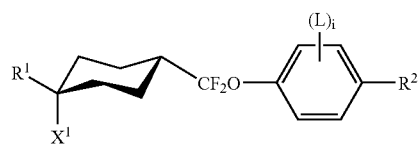 I1

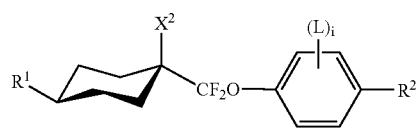 I2

 I3

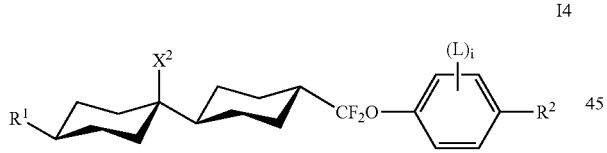 I4

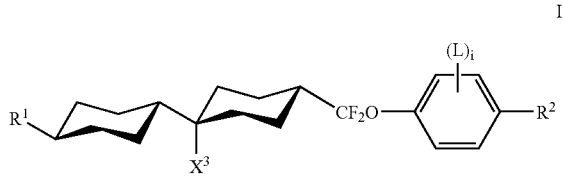 I5

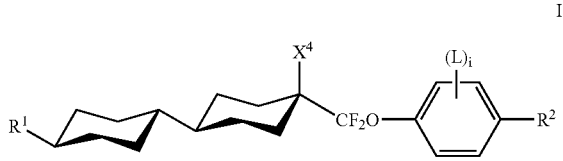 I6

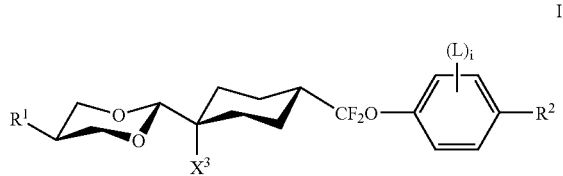 I7

-continued

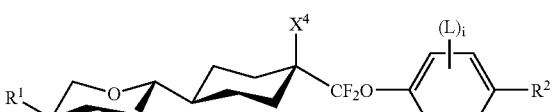 I8

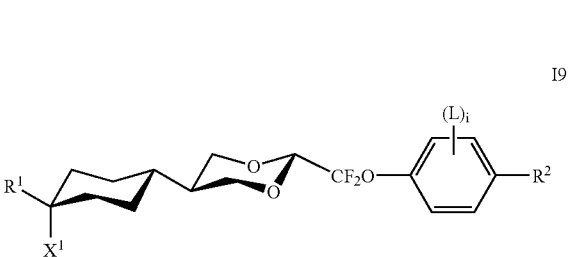 I9

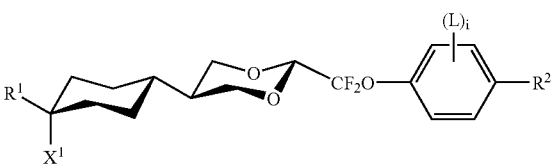 I10

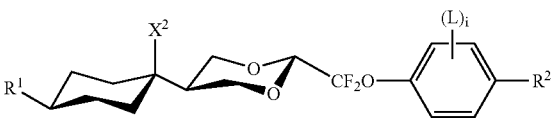 I11

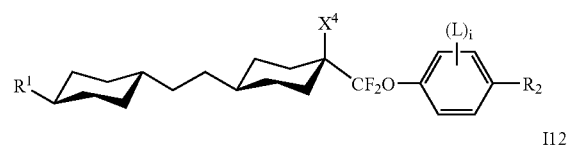 I12

 I13

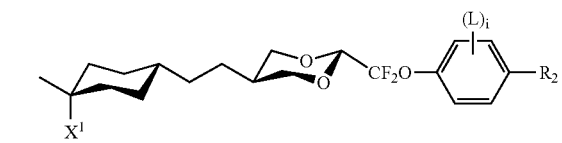 I14

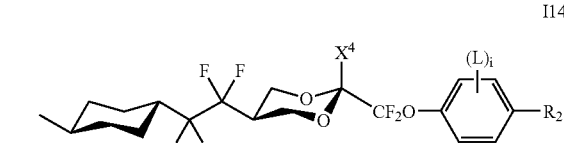

wherein, L is F, Cl and/or —CN, and i is 0, 1, 2, 3 or 4.

12. A liquid-crystalline medium of claim 5, which contains from 1 to 40%, of the compounds of the formula I.

13. A liquid-crystalline medium of claim 5, which contains from 5 to 30% of the compounds of the formula I.

14. A liquid-crystalline medium of claim 5, which contains from 45 to 90%, of the compounds of the formula I.

15. A liquid-crystalline medium of claim 5, which contains three, four or five compounds of the formula I.

16. A compound according to claim 1, wherein m=0.

* * * * *

UNITED STATES PATENT AND TRADEMARK OFFICE
CERTIFICATE OF CORRECTION

PATENT NO. : 7,029,730 B2
APPLICATION NO. : 10/479621
DATED : April 18, 2006
INVENTOR(S) : Peer Kirsch It is certified that error appears in the above-identified patent and that said Letters Patent is hereby corrected as shown below:

Column 142, line 50 reads

"
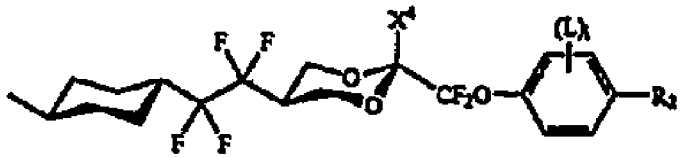
"

should read
--
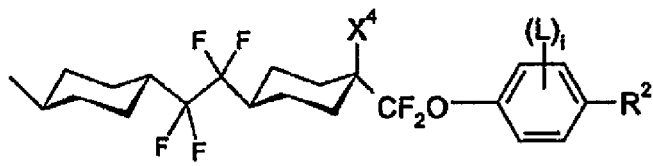
--

Signed and Sealed this

Twenty-seventh Day of February, 2007

JON W. DUDAS
*Director of the United States Patent and Trademark Office*